(12) United States Patent
Giuffrida et al.

(10) Patent No.: US 11,559,250 B1
(45) Date of Patent: *Jan. 24, 2023

(54) HIGH SENSITIVITY MOVEMENT DISORDER TREATMENT DEVICE OR SYSTEM

(71) Applicant: Great Lakes NeuroTechnologies Inc., Cleveland, OH (US)

(72) Inventors: Joseph P. Giuffrida, Hinckley, OH (US); Dustin A. Heldman, Shaker Heights, OH (US)

(73) Assignee: Great Lakes NeuroTechnologies Inc., Cleveland, OH (US)

( * ) Notice: Subject to any disclaimer, the term of this patent is extended or adjusted under 35 U.S.C. 154(b) by 241 days.

This patent is subject to a terminal disclaimer.

(21) Appl. No.: 17/001,796

(22) Filed: Aug. 25, 2020

Related U.S. Application Data

(63) Continuation of application No. 14/193,286, filed on Feb. 28, 2014, now Pat. No. 10,786,625, which is a
(Continued)

(51) Int. Cl.
*A61B 5/11* (2006.01)
*G16H 40/67* (2018.01)
(Continued)

(52) U.S. Cl.
CPC .......... *A61B 5/4839* (2013.01); *A61B 5/0022* (2013.01); *A61B 5/1101* (2013.01); *A61B 5/1123* (2013.01); *A61B 5/389* (2021.01); *A61B 5/4082* (2013.01); *A61B 5/6826* (2013.01); *A61B 5/742* (2013.01); *A61M 5/14244* (2013.01); *A61M 5/1723* (2013.01); *G16H 40/67* (2018.01); *A61B 5/316* (2021.01);
(Continued)

(58) Field of Classification Search
CPC ... A61B 5/4839; A61B 5/0022; A61B 5/1101; A61B 5/1123; A61B 5/389; A61B 5/4082; A61B 5/6826; A61B 5/742; A61B 5/316; A61B 5/6824; A61B 5/6825; A61B 5/7239; A61B 5/7242; A61B 2562/0219; A61M 5/14244; A61M 5/1723; G16H 40/67
See application file for complete search history.

(56) References Cited

U.S. PATENT DOCUMENTS

2006/0106431 A1* 5/2006 Wyler ................ A61N 1/36067
607/48

* cited by examiner

*Primary Examiner* — Rene T Towa
(74) *Attorney, Agent, or Firm* — Brian Kolkowski

(57) ABSTRACT

The present invention relates to a movement disorder monitor with high sensitivity, and a method of measuring the severity of a subject's movement disorder. The present invention additionally relates to a drug delivery system for dosing a subject in response to the increased severity of a subject's symptoms. The present invention provides for a system and method, which can accurately and repeatably quantify symptoms of movements disorders, accurately quantifies symptoms utilizing both kinetic information and/or electromyography (EMG) data, that can be worn continuously to provide continuous information to be analyzed as needed by the clinician, that can provide analysis in real-time, that allows for home monitoring of symptoms in subject's with these movement disorders to capture the complex fluctuation patterns of the disease over the course of days, weeks or months, that maximizes subject safety, and that provides substantially real-time remote access to data by the clinician or physician.

20 Claims, 36 Drawing Sheets

Related U.S. Application Data continuation of application No. 13/784,939, filed on Mar. 5, 2013, now Pat. No. 8,845,557, which is a continuation-in-part of application No. 13/455,423, filed on Apr. 25, 2012, now Pat. No. 8,679,038, which is a continuation of application No. 11/082,668, filed on Mar. 17, 2005, now Pat. No. 8,187,209.

(51) Int. Cl.
| | | |
|---|---|---|
| *A61M 5/142* | (2006.01) | |
| *A61M 5/172* | (2006.01) | |
| *A61B 5/389* | (2021.01) | |
| *A61B 5/00* | (2006.01) | |
| *A61B 5/316* | (2021.01) | |

(52) U.S. Cl.
CPC .......... *A61B 5/6824* (2013.01); *A61B 5/6825* (2013.01); *A61B 5/7239* (2013.01); *A61B 5/7242* (2013.01); *A61B 2562/0219* (2013.01)

HIGH SENSITIVITY MOVEMENT DISORDER TREATMENT DEVICE OR SYSTEM

CROSS-REFERENCE TO RELATED APPLICATIONS

This application is a continuation of U.S. patent application Ser. No. 14/193,286, filed on Feb. 28, 2014, which was a continuation of U.S. patent application Ser. No. 13/784,939, filed on Mar. 5, 2013 and issued as U.S. Pat. No. 8,845,557 on Sep. 30, 2014, which was a continuation-n-part of U.S. patent application Ser. No. 13/455,423, which was filed on Apr. 25, 2012 and issued as U.S. Pat. No. 8,679,038 on Mar. 25, 2014, and which was a continuation of U.S. patent application Ser. No. 11/082,668 which was filed on Mar. 17, 2005, and which issued as U.S. Pat. No. 8,187,209 on May 29, 2012. The disclosure and drawings of each of the above patents and applications are hereby incorporated by reference in their entirety.

The U.S. Government has a paid-up license in this invention and the right in limited circumstances to require the patent owner to license others on reasonable terms provided for by the terms of grant numbers 1R43NS043816-01A1, 2R44N5043816-02/03 1R43NS074627, 7R43NS065554, and 2R44MD004049, awarded by the National Institutes of Health.

BACKGROUND OF THE INVENTION

1. Field of the Invention

The present invention relates to a movement disorder monitor, and a method of measuring and quantifying the severity of a subject's movement disorder and symptoms thereof. The present invention additionally relates to a development system, and a treatment and drug delivery system for dosing a subject in response to changes in severity of a subject's symptoms.

2. Technical Background

Movement disorders include, but are not limited to, Parkinson's disease (PD), essential tremor, dystonia, and Tourette's syndrome. Such disorders present a multitude of symptoms affecting a person's daily life, those symptoms include tremor, bradykinesia, rigidity, gait/balance disturbances, dyskinesias, and the like. The treatments can involve pharmaceutical interventions, fetal cell transplants, surgery, or deep brain stimulation in some of these disorders. The efficacy of these interventions is often judged by the intervention's ability to alleviate subject symptoms and improve their quality of life. With Parkinson's disease for example, the major symptoms that affect quality of life are tremor, bradykinesia, rigidity, and dyskinesia. These symptoms are partly responsible for the subject's functional disability and social embarrassment.

Tremors are involuntary muscle contractions characterized by oscillations of a body part. Tremor of the hands can be cosmetically upsetting and affect functional tasks such as grasping of objects. Resting tremors usually occur at frequencies of approximately 4-7 Hz while the frequency of action of postural tremor is higher, usually between 9-11 Hz. Tremor is a symptom often targeted by treatment. The standard clinical method for analyzing rest and postural or action tremor is qualitative assessment by a clinician and assignment of a score.

Bradykinesia refers to delays or hesitations in initiating movements and slowness in executing movements. The standard clinical method for analyzing bradykinesia is qualitative assessment by a clinician and assignment of a score. This score is assigned while the subject completes a repetitive finger-tapping task, a repetitive hand opening-closing task, and a pronation-supination task. Objective assessment by this means is difficult and variable. It has been found that movement rate and time are useful in better characterizing bradykinesia.

Rigidity occurs because muscles of the body are overly excited. The neurons involved in inhibition circuitry have died due to Parkinson's disease and muscles may receive continuous excitation. Rigidity causes the joints of the subject to become stiff and decreases range of motion. During normal movement, an agonist muscle contracts while the antagonist muscles relax. However, due to the constant motor unit input, the antagonist is unable to relax. Again, the standard clinical method for analyzing rigidity is qualitative assessment by a clinician and assignment of a score. To do so a clinician passively moves the subject's joints through a range of motion while the subject relaxes.

Dyskinesia is one of the most common and disabling complications of chronic drug therapy. Dyskinesias are wild involuntary movements that typically occur when the benefit from the drug therapy is at its maximum. Clinical assessment of dyskinesias typically relies on self-reporting by the subject. There is a great need to objectively quantify these involuntary movements in view of the growing number of pharmacologic agents and surgical procedures to improve dyskinesia.

While standard clinical evaluation involves qualitative assessment of these symptoms, recently some efforts have been made to quantify symptoms of movement disorders. Accelerometers and gyroscopes have been used individually to quantify some of these movement disorder symptoms, however, alone each sensor has limitations. Accelerometers operate in response to the local gravitational field; therefore they often have problems in separating changes in linear acceleration from rotation. Further, results of a second integration required to obtain linear position are often contaminated with noise, making measurement difficult at best. Gyroscopes measure angular velocity independent of gravity with a good frequency response; however, static angular position cannot be measured accurately due to DC drift characteristic with these devices. Combining the information from both accelerometers and gyroscopes can provide a more accurate method of quantifying motion.

With the tremendous amount of research into neuroprotective treatments designed to slow the progression of movement disorders, and particularly Parkinson's disease, the need for standardized, highly sensitive assessments of movement disorder treatments cannot be understated. Large-scale clinical drug trials for medication and drug treatment methods often involve dozens of sites and thousands of subjects located all over the world. Outcome measures are typically in the form of a single clinical assessment completed at weekly or monthly intervals. These clinical assessments can suffer from bias, placebo effects, limited resolution, and poor intra- and inter-rater reliability.

Currently, no commercially available system provides a means to objectively quantify the severity of movement disorder symptoms in real-time. Furthermore, many of these systems are bulky and cannot easily be worn by a subject during normal daily activities so as a result can only be used to monitor the subject in an intermittent fashion. In addition, some of these systems are tethered, which reduces subject safety, limits home monitoring capabilities, and does not allow for recording of some movement disorder symptoms. Finally, none of the current systems have clinician interface software, which quantifies symptoms such as tremor, bradykinesia, rigidity, and dyskinesias and relates them to standard rating scales such as the Unified Parkinson's Disease Rating Scale (UPDRS). Additionally, none of these systems have clinical video instruction and real-time clinical video feedback.

Even further, the currently available systems are typically hindered by a large degree of variability in the quantification of symptom severity. This is due in large part to the subjective nature of scoring systems, such as the UPDRS, which require clinician observation of the subject and/or movement data, and/or subject feedback regarding their subjective evaluation of the severity of symptoms. Systems requiring subject feedback, for example by use of a journal for recording the subject's perception of symptoms throughout the day, suffer from a lack of subject compliance. Many subjects provide skewed information, or more often fail to comply with the reporting standards completely and then fill in the journal near to the time of an appointment with the clinician, rather than on a daily basis as the symptoms occur (or do not occur). Even systems which rely in part or completely on scoring of clinicians or other trained personnel offer a high degree of variability due to the need for subjective observation or reporting of the severity of symptoms. Different clinicians might score a given observation differently, and the same clinician might score the same observation differently if presented with the data at different times. This variability and subjectivity can prevent an accurate quantification of symptom severity which may lead to inappropriate treatment of the subject including under or over medication. This variability and subjectivity further hinders the research and development process requiring long periods of time and large numbers of subjects in order to verify and qualify new treatment methods for clinical use.

Measurement errors can take the form of inconsistencies caused by the participant's physical or mental condition, variations in the testing procedure, or tester error. Additionally, subjects may perform better or more consistent on a task due to learning effects rather than as a result of the therapy being studied. Various methods to improve consistency such as using the same rater or testing on the same time of day can improve reliability; however, most of these techniques are not practical for large, multi-center clinical trials.

As an example, the most common outcome measure in Parkinson's Disease drug trials, the motor section of the Unified Parkinson's Disease Rating Scale (UPDRS Section III), requires a clinician to qualitatively rate various motor symptoms on a 0-4 integer scale while viewing the subject performing tasks. While studies have shown relative high test-retest reliability for the UPDRS-III as a whole (see e.g., Teresa Steffen et al, Test-Retest Reliability and Minimal Detectable Change on Balance and Ambulation Tests, the 36-Item Short-Form Health Survey, and the Unified Parkinson Disease Rating Scale in People with Parkinsonism, 88 PHYSICAL THERAPY 733 (Jun. 1, 2008)), this traditional method of subject evaluation presents several problems for large scale pharmaceutical studies. The required presence of a trained clinician to rate symptoms creates costs associated with subject travel and clinician time. In addition, the use of medications for treatment of Parkinson's Disease often causes symptom fluctuations during the day, which cannot be monitored during a single visit with the trained clinician. To compensate for this lack of temporal resolution, subjects are often asked to complete daily diaries; however, in clinical trials, these diaries are notoriously poor in quality as subjects may have a tendency to wait and fill out the diaries in retrospect rather than throughout the day on a daily basis. Also, clinical trials typically employ several clinicians at different sites, which may lead to symptom scoring variability and in turn decreased sensitivity due to the subjective observations of each clinician. Finally, the discrete nature of the integer scores (0, 1, 2, 3, or 4) under the UPDRS does not allow for the high sensitivity measurements that would be necessary to capture the very subtle changes that might occur during a neuroprotective drug trial. Neuroprotective drugs target subjects with early Parkinson's Disease when symptoms are still very mild (correlating to a 0 or 1 score on the UPDRS). Evaluation of neuroprotective therapies can take years or even decades due to the long period before a UPDRS measurable response is seen.

Many researchers have cited the inability to measure slight changes in motor symptom severity using the UPDRS as a hurdle in evaluating potential neuroprotective agents. And while reliability of the UPDRS-III (the motor section) as a whole may be high, specific symptoms or items, such as those related to bradykinesia for example, lack specificity and suffer from poor intra- and inter-rater reliability. For rating tremor, the Movement Disorders Society (MDS) revision of the UPDRS tremor scoring guidelines specify amplitude ranges in centimeters that correspond to a 0-4 score (see C. G. Goetz et al., Movement Disorder Society-sponsored revision of the Unified Parkinson's Disease Rating Scale (MDS-UPDRS): scale presentation and clinimetric testing results, 23 Mov. Disord. 2129 (Nov. 15, 2008)); however, it is difficult, if not impossible, to judge tremor amplitude precisely by visual observation alone. Even if precise visual observations were possible, converting a wide range of amplitudes to an integer score greatly reduces resolution. For evaluating finger tapping, hand movements, and pronation-supination, evaluations are even less reliable since raters must account for speed, amplitude, rhythm, hesitations, freezing, and fatigue, all with a single score. In a study designed to test inter-rater reliability, the UPDRS finger tapping task, the most widely used measure of bradykinesia, was misclassified by 70.6% of the 54.6% of clinicians who failed their first rating (see C. G. Goetz and G. T. Stebbins, Assuring interrater reliability for the UPDRS motor section: utility of the UPDRS teaching tape. 19 Mov. Disord. 1453 (2004)). As for intra-rater reliability, two studies showed only poor to fair agreement in bradykinesia ratings (see D. A. Bennett et al., Metric properties of nurses' ratings of parkinsonian signs with a modified Unified Parkinson's Disease Rating Scale, 49 Neurology 1580 (1997); see also R. Camicioli R et al., Discriminating mild parkinsonism: Methods for epidemiological research. 16 Mov. Disord. 33 (2001)). A third study showed fair to good agreement; however, raters were not blinded and the subjects had early, untreated PD, which restricts the range of test-retest reliability (see A. Siderowf et al., Test-retest reliability of the unified Parkinson's disease rating scale in patients with early Parkinson's disease: results from a multicenter clinical trial. 17 Mov. Disord. 758 (2002)). Recently, the modified bradykinesia rating scale (MBRS) was introduced for independently rating the bradykinesia manifestations of speed, amplitude, and rhythm. Each manifestation is given an integer score from 0-4 during finger-tapping, hand movements, and pronation-supination tasks. The MBRS has similar inter- and intra-rater reliability to that of the UPDRS and was found to be more sensitive than the UPDRS in identifying how different aspects of bradykinesia respond to medication, highlighting the need for more sensitive assessment of bradykinesia. While an improvement, the MBRS is still a subjective scale with limited (whole number: 0, 1, 2, 3, or 4) resolution, cannot be captured without a clinician present, and has inter- and intra-rater reliability issues similar to the UPDRS (see D. A. Heldman D A et al, The modified bradykinesia rating scale for Parkinson's disease: Reliability and comparison with kinematic measures, 26 Mov. Disord. 1859 (2011).

It is therefore an object of the present invention to provide a system for accurately quantifying symptoms of movement disorders. It is still another object of the present invention to provide a system that accurately quantifies symptoms utilizing both kinetic information, and in some embodiments electromyography (EMG) data. It is further an object of the present invention to provide accurate, reliable, repeatable quantification of movement disorder symptoms allowing for reduced time and cost in development, and more rapid and accurate treatment of subjects. It is still another object of the present invention to provide a wireless movement disorder system that can be worn continuously to provide continuous information to be analyzed as needed by the clinician, though need not be, and may preferably not be worn continuously. It is still further another object of the present invention to provide a movement disorder system that can provide analysis in real-time. It is a further object of the present invention to provide a movement disorder symptom quantification system that can automatically and immediately make data and the provided analytical information available for further analysis and review in real-time. It is still further another object of the present invention to provide a movement disorder system to allow for home monitoring of symptoms in subject's with these movement disorders to capture the complex fluctuation patterns of the disease over the course of days, weeks or months. It is still further an object of the present invention to maximize subject safety. It is still further an object of the present invention to provide a system with clinical video instruction and real-time clinical video feedback. It is still further an object of the present invention to provide a treatment delivery system that can monitor symptoms in subject's and deliver treatment in response to those symptoms. Finally it is the object of the present invention to provide remote access to the clinician or physician.

SUMMARY OF THE INVENTION

The present invention relates to a movement disorder monitor, and a method of measuring the severity of a subject's movement disorder. The present invention additionally relates to a treatment delivery system including drugs for treating or dosing a subject in response to changes in the severity of a subject's symptoms.

The present invention provides for a system and method, which can accurately quantify symptoms of movements disorders, accurately quantifies symptoms utilizing both kinetic information and in some embodiments electromyography (EMG) data, that can be worn continuously to provide continuous information to be analyzed as needed by the clinician, that can provide analysis in real-time, that allows for home monitoring of symptoms in subject's with these movement disorders to capture the complex fluctuation patterns of the disease over the course of days, weeks or months, that maximizes subject safety, and that provides remote access to the clinician or physician. One such system is described in U.S. patent application Ser. No. 12/818,819, which is herein incorporated by reference.

In one embodiment, the present invention includes a portable movement disorder device for measuring severity of a subject's movement disorder comprising a first sensor for measuring a subject's external body motion having a signal related to the external body motion; and a second sensor for measuring a subject's electrical muscle activity wherein the severity of the subject's movement disorder is calculated based in part on the signals of the first and second sensors.

In another embodiment, the present invention includes a method of measuring severity of a subject's movement disorder comprising the steps of measuring a subject's external body motion; transmitting wirelessly a signal based in part on the subject's measured external body motion; receiving the wirelessly transmitted signal; and scoring the severity of a subject's movement disorder based in part on the wirelessly transmitted signal.

In still another embodiment, the present invention includes a portable movement disorder device or system for measuring severity of a subject's movement disorder comprising at least one sensor having a signal for measuring a subject's external body motion or physiological signal associated with a movement disorder; at least one processor for receiving the signal, and calculating the severity of the subject's movement disorder in real time.

In still another embodiment, the present invention includes a portable movement disorder device or system for measuring severity of a subject's movement disorder comprising at least one sensor having a signal for measuring a subject's external body motion or physiological signal associated with a movement disorder; recording that data to memory on the device, downloading that data to a computer at a later time and calculating the severity of the subject's movement disorder.

In still another embodiment, the present invention includes a drug delivery system comprising at least one sensor having a signal for measuring a subject's external body motion or physiological signal associated with a movement disorder; an actuator which allows a medication to be delivered from a reservoir external to the subject to a point internal to the subject; and a closed-loop control system for activating and deactivating the actuator based in part on the signal from the at least one sensor.

In yet another embodiment, the present invention includes a method of quantifying severity of a subject's movement disorder comprising the steps of providing a device to a subject, the device comprising at least one sensor having a signal corresponding to a subject's external body motion associated with a movement disorder, measuring the subject's external body motion with the at least one sensor while the subject performs at least one movement disorder test corresponding to at least one movement disorder symptom, transmitting a signal from the at least one sensor to a processor, and calculating substantially in real time with the processor a symptom quantification measure based at least in part on the signal from the at least one sensor, wherein the device has a real-time average intraclass correlation (ICC) of at least about 0.60.

In still another embodiment, the present invention includes a method of quantifying severity of a subject's movement disorder comprising the steps of providing a device to a subject, the device comprising at least one sensor having a signal corresponding to a subject's external body motion associated with a movement disorder, measuring the subject's external body motion with the at least one sensor while the subject performs at least one movement disorder test corresponding to at least one movement disorder symptom, transmitting a signal from the at least one sensor to a processor, and calculating substantially in real time with the processor a symptom quantification measure based at least in part on the signal from the at least one sensor, wherein the device has a real-time average minimum detectable change (MDC) that represents a change of about 25% or less of the total scale of the particular test.

In yet another embodiment, the present invention includes a method of quantifying severity of a subject's movement disorder comprising the steps of providing a device to a subject, the device comprising at least one sensor having a signal corresponding to a subject's external body motion associated with a movement disorder, measuring the subject's external body motion with the at least one sensor while the subject performs at least one first movement disorder test corresponding to at least one movement disorder symptom, transmitting a first signal from the at least one sensor to a processor, calculating substantially in real time with the processor a first symptom quantification measure based at least in part on the first signal from the at least one sensor, measuring the subject's external body motion with the at least one sensor while the subject performs at least one second movement disorder test corresponding to at least one movement disorder symptom, the at least one second movement disorder test being the same as the at least one first movement disorder test, transmitting a second signal from the at least one sensor to a processor, and calculating substantially in real time with the processor a second symptom quantification measure based at least in part on the second signal from the at least one sensor, wherein the first and second symptom quantification measures have an average intraclass correlation (ICC) of at least about 0.60.

In still another embodiment, the present invention includes a method of quantifying severity of a subject's movement disorder comprising the steps of providing a device to a subject, the device comprising at least one sensor having a signal corresponding to a subject's external body motion associated with a movement disorder, measuring the subject's external body motion with the at least one sensor while the subject performs at least one first movement disorder test corresponding to at least one movement disorder symptom, transmitting a first signal from the at least one sensor to a processor, calculating substantially in real time with the processor a first symptom quantification measure based at least in part on the signal from the at least one sensor, measuring the subject's external body motion with the at least one sensor while the subject performs at least one second movement disorder test corresponding to at least one movement disorder symptom, the at least one second movement disorder test being the same as the at least one first movement disorder test, transmitting a second signal from the at least one sensor to a processor, and calculating substantially in real time with the processor a second symptom quantification measure based at least in part on the second signal from the at least one sensor, wherein the first and second symptom quantification measures have an average minimal detectable change (MDC) that represents a change of about 25% or less of the total scale of the particular test.

In yet another embodiment, the present invention includes a method of quantifying severity of a subject's movement disorder comprising the steps of providing a device to a subject, the device comprising at least three sensors, each having a signal corresponding to a subject's external body motion associated with a movement disorder, measuring the subject's external body motion with the at least three sensors while the subject performs at least one first movement disorder test corresponding to at least one movement disorder symptom, transmitting first signals from each of the at least three sensors to a processor, calculating substantially in real time with the processor a first symptom quantification measure based at least in part on the first signals from the at least three sensors, measuring the subject's external body motion with the at least three sensors while the subject performs at least one second movement disorder test corresponding to at least one movement disorder symptom, the at least one second movement disorder test being the same as the at least one first movement disorder test, transmitting second signals from each of the at least three sensors to a processor, and calculating substantially in real time with the processor a second symptom quantification measure based at least in part on the second signals from the at least three sensors, wherein the first and second symptom quantification measures have an average intraclass correlation (ICC) of at least about 0.60.

In yet another embodiment, the present invention includes a method of quantifying severity of a subject's movement disorder comprising the steps of providing a device to a subject, the device comprising at least one sensor having a signal corresponding to a subject's external body motion associated with a movement disorder, measuring the subject's external body motion with the at least one sensor while the subject performs at least two first movement disorder tests, the at least two tests belonging to a symptom group corresponding to the subject's motor examination, transmitting a first signal from the at least one sensor to a processor, calculating substantially in real time with the processor a first motor examination symptom quantification measure based at least in part on the first signal from the at least one sensor, measuring the subject's external body motion with the at least one sensor while the subject performs at least two second movement disorder tests, the at least two tests belonging to a symptom group corresponding to the subject's motor examination, the at least two second movement disorder tests being the same as the at least two first movement disorder tests, transmitting a second signal from the at least one sensor to a processor, and calculating substantially in real time with the processor a second motor examination symptom quantification measure based at least in part on the second signal from the at least one sensor, wherein the first and second motor examination symptom quantification measures have an average intraclass correlation (ICC) of at least about 0.60.

In yet another embodiment, the present invention includes a method of quantifying severity of a subject's movement disorder comprising the steps of providing a device to a subject, the device comprising at least one sensor having a signal corresponding to a subject's external body motion associated with a movement disorder, measuring the subject's external body motion with the at least one sensor while the subject performs at least two first movement disorder tests, the at least two tests belonging to a symptom group corresponding to the subject's motor examination, transmitting a first signal from the at least one sensor to a processor, calculating substantially in real time with the processor a first motor examination symptom quantification measure based at least in part on the first signal from the at least one sensor, measuring the subject's external body motion with the at least one sensor while the subject performs at least two second movement disorder tests, the at least two tests belonging to a symptom group corresponding to the subject's motor examination, the at least two second movement disorder tests being the same as the at least two first movement disorder tests, transmitting a second signal from the at least one sensor to a processor, and calculating substantially in real time with the processor a second motor examination symptom quantification measure based at least in part on the second signal from the at least one sensor, wherein the first and second motor examination symptom quantification measures have an average minimum detectable change (MDC) that represents a change of about 25% or less of the total scale of the particular test.

In still another embodiment, the present invention includes a method of quantifying severity of a subject's movement disorder comprising the steps of providing a device to a subject, the device comprising at least one sensor having a signal corresponding to a subject's external body motion associated with a movement disorder, measuring the subject's external body motion with the at least one sensor while the subject performs at least three first movement disorder tests, the at least three first tests belonging to a symptom group corresponding to the subject's motor examination, transmitting a first signal from the at least one sensor to a processor, calculating substantially in real time with the processor a first motor examination symptom quantification measure for each of the at least three first tests, each measure based at least in part on the first signal from the at least one sensor, creating a first total symptom quantification measure by combining the three first symptom quantification measures, measuring the subject's external body motion with the at least one sensor while the subject performs at least three second movement disorder tests, the at least three second tests belonging to a symptom group corresponding to the subject's motor examination, the at least three second movement disorder tests being the same as the at least three first movement disorder tests, transmitting a second signal from the at least one sensor to a processor, calculating substantially in real time with the processor a second motor examination symptom quantification measure for each of the at least three second tests, each measure based at least in part on the second signal from the at least one sensor, creating a second total symptom quantification measure by combining the three second symptom quantification measures, wherein the first and second total symptom quantification measures have an average minimum detectable change (MDC) that represents a change of about 25% or less of the total scale of the particular test.

In still yet another embodiment, the present invention includes a method of quantifying severity of a subject's movement disorder comprising the steps of providing a device to a subject, the device comprising at least three sensors, each having a signal corresponding to a subject's external body motion associated with a movement disorder, measuring the subject's external body motion with the at least three sensors while the subject performs at least one first movement disorder test corresponding to at least one movement disorder symptom, transmitting first signals from each of the at least three sensors to a processor, calculating substantially in real time with the processor a first symptom quantification measure based at least in part on the first signals from the at least three sensors, measuring the subject's external body motion with the at least three sensors while the subject performs at least one second movement disorder test corresponding to at least one movement disorder symptom, the at least one second movement disorder test being the same as the at least one first movement disorder test, transmitting second signals from each of the at least three sensors to a processor, and calculating substantially in real time with the processor a second symptom quantification measure based at least in part on the second signals from the at least three sensors, wherein the first and second symptom quantification measures have an average minimal detectable change (MDC) that represents a change of about 25% or less of the total scale of the particular test.

In still yet another embodiment, the present invention includes a portable device for quantifying severity of a subject's movement disorder comprising at least one sensor having a signal for measuring a subject's external body motion or physiological signal associated with a movement disorder, and at least one processor for receiving the sensor signal and calculating the severity of the subject's movement disorder symptom(s) in real time, wherein the device has a real-time average intraclass correlation (ICC) of at least about 0.60.

In yet still another embodiment, the present invention includes a portable device for quantifying severity of a subject's movement disorder comprising at least one sensor having a signal for measuring a subject's external body motion or physiological signal associated with a movement disorder, and at least one processor for receiving the sensor signal and calculating the severity of the subject's movement disorder symptom(s) in real time, wherein the device has a real-time average minimum detectable change (MDC) that represents a change of about 25% or less of the total scale of a particular test.

In yet another embodiment, the present invention includes a portable device for quantifying severity of a subject's movement disorder comprising a first sensor for measuring a subject's external body motion having a signal related to the subject's external body motion, and a second sensor for measuring a subject's electrical muscle activity having a signal related to the subject's electrical muscle activity, wherein the severity of the subject's movement disorder is calculated based in part on the signals of the first and second sensors, and wherein subsequent measurements of movement disorder severity result in an intraclass correlation of at least about 0.60.

In still another embodiment, the present invention includes a portable device for quantifying severity of a subject's movement disorder comprising a first sensor for measuring a subject's external body motion having a signal related to the subject's external body motion, and a second sensor for measuring a subject's electrical muscle activity having a signal related to the subject's electrical muscle activity, wherein the severity of the subject's movement disorder is calculated based in part on the signals of the first and second sensors, and wherein subsequent measurements of movement disorder severity result in a minimum detectable change (MDC) that represents a change of about 25% or less of the total scale of a particular test.

In still yet another embodiment, the present invention includes a portable device for quantifying severity of a subject's movement disorder comprising at least one external sensor having a signal for measuring a subject's external body motion or physiological signal associated with a movement disorder, and at least one processor for receiving the signal, and calculating the severity of the subject's movement disorder in real time, wherein subsequent measurements of movement disorder severity result in an intraclass correlation of at least about 0.60.

In yet still another embodiment, the present invention includes a portable device for quantifying severity of a subject's movement disorder comprising at least one external sensor having a signal for measuring a subject's external body motion or physiological signal associated with a movement disorder, and at least one processor for receiving the signal, and calculating the severity of the subject's movement disorder in real time, wherein subsequent measurements of movement disorder severity result in a minimum detectable change (MDC) that represents a change of about 25% or less of the total scale of a particular test.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention; and together with the description serve to explain the principles and operation of the invention.

DESCRIPTION OF THE PREFERRED EMBODIMENT

Figure 1:
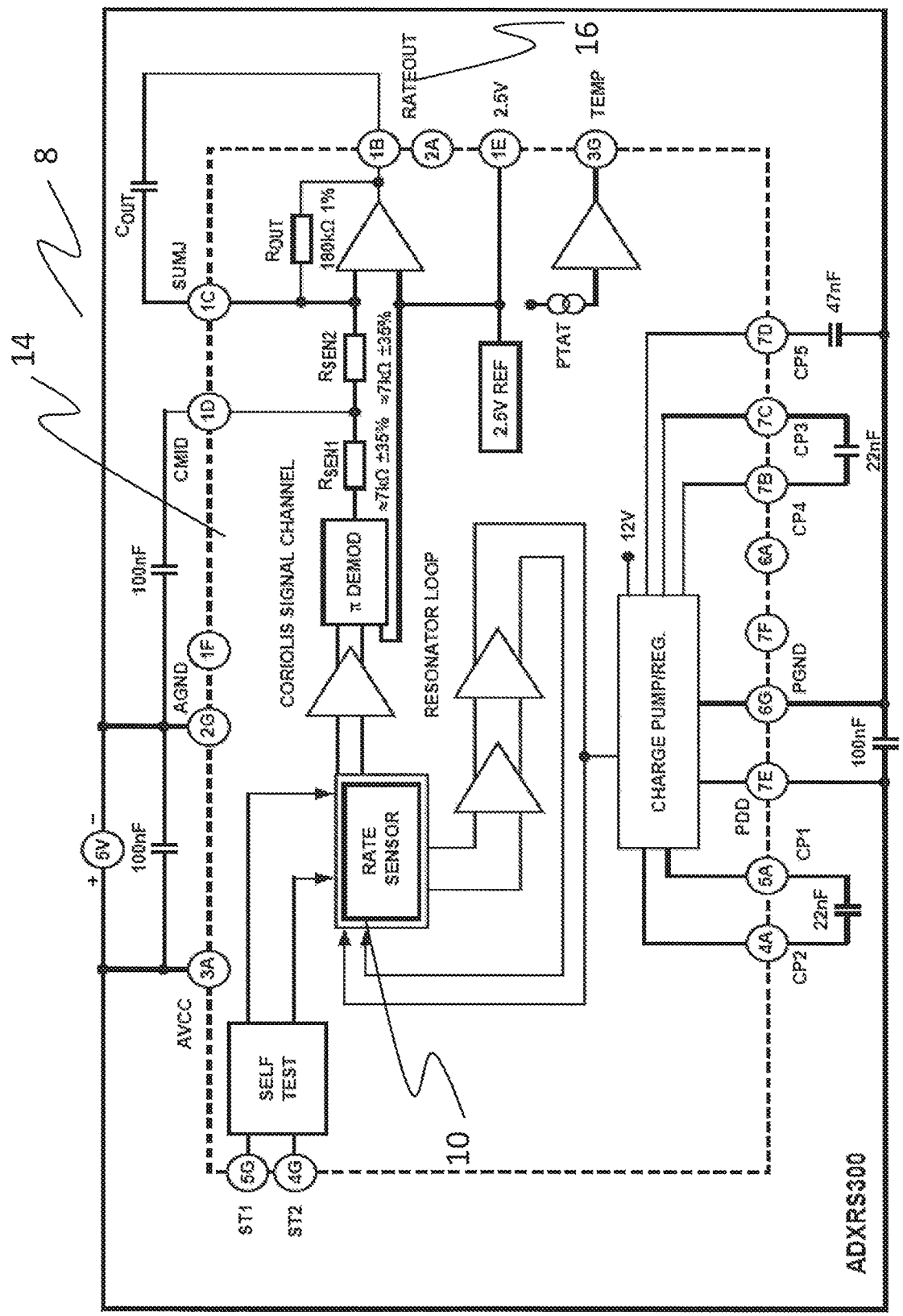
FIG. 1. Electrical schematic of a gyroscope useful in the present invention.

The present invention relates to a movement disorder monitor, and a method of measuring the severity of a subject's movement disorder. The present invention additionally relates to a drug delivery system for dosing a subject in response to the increased severity of a subject's symptoms.

The devices, systems and methods of the various embodiments of the present invention are used to analyze, score, and treat various movement disorders. Movement disorders for purposes of this application include but are not limited to Parkinson's disease (PD) and essential tremor. Some of the treatments used for these disorders involve pharmaceutical interventions, fetal cell transplants, surgery, or deep brain stimulation. The efficacy of these interventions is often judged by the interventions ability to alleviate subject symptoms and improve their quality of life. The subject on which the devices, system or method is used is a human or other form of animal.

The devices of the various embodiments of the present invention are preferably portable. By portable it is meant among other things that the device is capable of being transported relatively easily. Relative easy in transport means that the device can be carried by a single person, generally in a carrying case to the point of use or application. Furthermore the device preferably should be relatively lightweight. By relatively light-weight, preferably the device weighs less than about 3 lbs., more preferably less than about 2 lbs., even more preferably less than about 1 lb., and most preferably less than about 0.5 lbs. By being lightweight and further compact, the device should gain greater acceptance for use by the subject. The system for measuring and calculating the severity of the symptoms including external computers preferably weighs less than about 15 lbs., more preferably less than about 10 lbs., and most preferably less than about 5 lbs. This system more preferably can fit in a reasonably sized carrying case so the subject or their caregiver can easily transport the system.

Another advantage of the systems and methods of the present invention is the ability to determine or calculate the severity of a subject's symptoms in real time, which may be measured or quantified by providing a symptom quantification measure or score. By real time it is meant that within 30 minutes the severity of a subject's symptoms can be calculated or determined. Preferably, the subject's symptoms can be calculated or determined in less than about 1 minute, more preferably in less than about 30 seconds, still more preferably in less than about 15 seconds, yet more preferably in less than about 10 seconds, even more preferably in less than about 5 seconds, yet still more preferably in less than about 1 second, even still more preferably in less than about 0.1 seconds, and most preferably in less than about 0.01 seconds.

The devices of the various embodiments of the present invention can form part of a system for use by a physician, veterinarian, technician or clinician for analysis or evaluation of a subject's movement disorder; for pharmaceutical research; or for delivery of pharmaceutical compounds. Other elements of this system may include but are not limited to receivers, routers, communication devices, processors, displays, drug delivery devices and the like, some of which are described further in various embodiments described in more detail below.

Various embodiments of the present invention may include a sensor for measuring a subject's external body motion. Many types of sensors are known by those skilled in the art for measuring external body motion. These sensors include but are not limited to accelerometers, gyroscopes, magnetometers, resistive bend sensors, force sensors, combinations thereof, and the like. Preferably, a combination using at least an accelerometer and gyroscope is used. FIG. 1 is an electrical schematic diagram for one embodiment of a gyroscope 8 used as a sensor or in a sensor of the present invention. The sensor element 10 functions on the principle of the Coriolis Effect and a capacitive-based sensing system. Rotation of the sensor 10 causes a shift in response of an oscillating silicon structure resulting in a change in capacitance. An application specific integrated circuit (ASIC) 14, using a standard complementary metal oxide semiconductor (CMOS) manufacturing process, detects and transforms changes in capacitance into an analog output voltage 16, which is proportional to angular rate. The sensor element design utilizes differential capacitors and symmetry to significantly reduce errors from acceleration and off-axis rotations.

Figure 2:
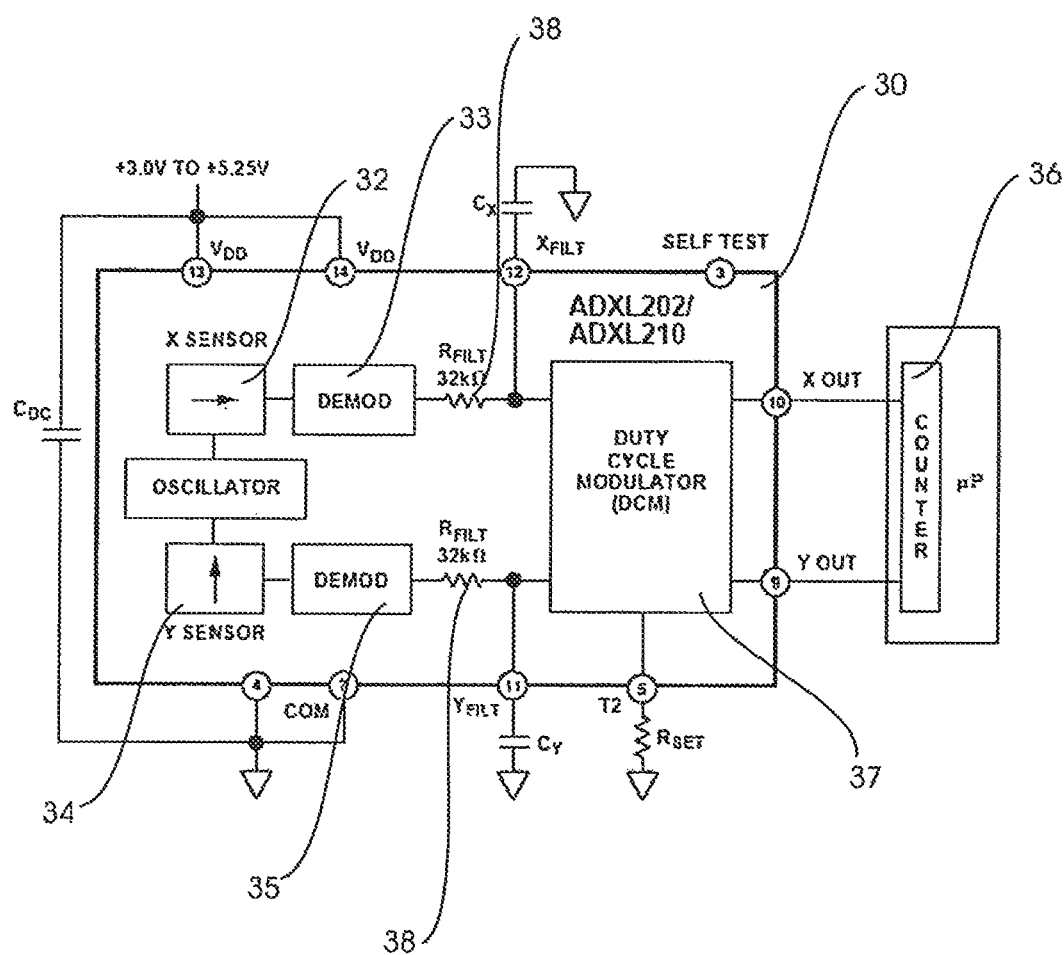
FIG. 2. Electrical schematic of a dual axis accelerometer useful in the present invention.

FIG. 2 is an electrical schematic diagram for one embodiment of a dual axis accelerometer of the present invention. The dual axis acceleration measurement system 30 is on a single monolithic IC. They contain a polysilicon surface-micromachined sensor and signal conditioning circuitry to implement an open-loop acceleration measurement architecture. For each axis 32, 34 an output circuit converts the analog signal to a duty cycle modulated (DCM) digital signal that can be decoded with a counter/timer port 36 on a microprocessor. The dual axis accelerometer is capable of measuring both positive and negative accelerations. The sensor 30 is a surface micromachined polysilicon structure built on top of the silicon wafer. Polysilicon springs suspend the structure over the surface of the wafer and provide a resistance against acceleration forces. Deflection of the structure is measured using a differential capacitor that consists of independent fixed plates and central plates attached to the moving mass. The fixed plates are driven by 180-degree out of phase square waves. Acceleration will deflect the beam and unbalance the differential capacitor, resulting in an output square wave whose amplitude is proportional to acceleration. Phase sensitive demodulation techniques are then used to rectify the signal and determine the direction of the acceleration. The output of the demodulator 33, 35 drives a duty cycle modulator (DCM) 37 stage through a 32 kOhm resistor 38. At this point a pin is available on each channel to allow the user to set the signal bandwidth of the device by adding a capacitor. This filtering improves measurement resolution and helps prevent aliasing. After being low-pass filtered, the analog signal is converted to a duty cycle modulated signal by the DCM stage 37. A single resistor sets the period for a complete cycle (T2). A 0 g acceleration produces a nominally 50% duty cycle. The acceleration signal can be determined by measuring the length of the T1 and T2 pulses with a counter/timer or with a polling loop using a low cost microcontroller.

Figure 3:
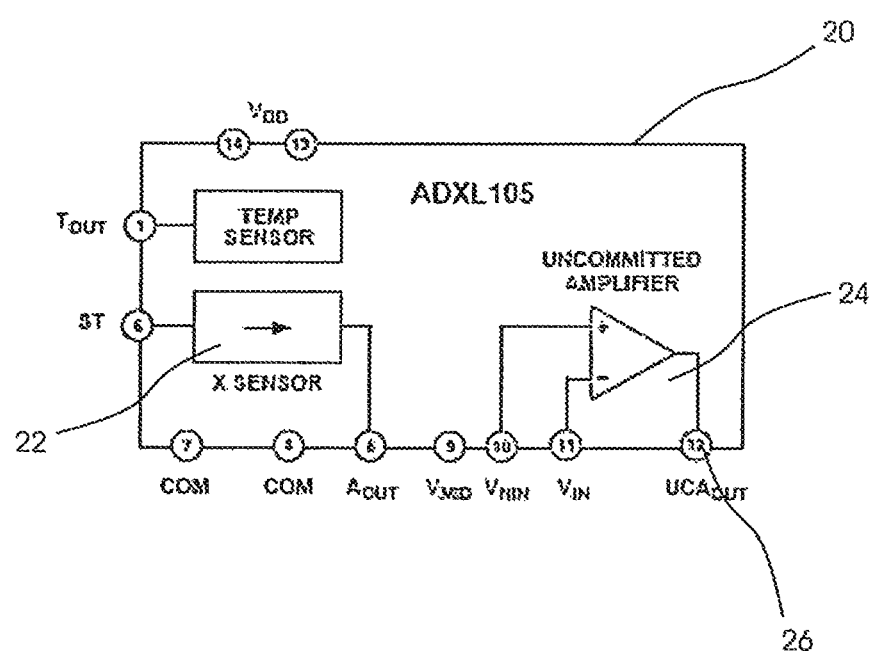
FIG. 3. Electrical schematic of a single axis accelerometer useful in the present invention.

FIG. 3 is an electrical schematic diagram for one embodiment of a single axis accelerometer of the present invention. The accelerometer 20 is fabricated using a surface micromachining process. The fabrication technique uses standard integrated circuit manufacturing methods enabling all signal processing circuitry to be combined on the same chip with the sensor 22. The surface micro-machined sensor element 22 is made by depositing polysilicon on a sacrificial oxide layer that is then etched away leaving a suspended sensor element. A differential capacitor sensor is composed of fixed plates and moving plates attached to the beam that moves in response to acceleration. Movement of the beam changes the differential capacitance, which is measured by the on chip circuitry. All the circuitry 24 needed to drive the sensor and convert the capacitance change to voltage is incorporated on the chip requiring no external components except for standard power supply decoupling. Both sensitivity and the zero-g value are ratiometric to the supply voltage, so that ratiometeric devices following the accelerometer (such as an analog to digital converter (ADC), etc.) will track the accelerometer if the supply voltage changes. The output voltage (VOUT) 26 is a function of both the acceleration input and the power supply voltage (VS).

Figure 4A:
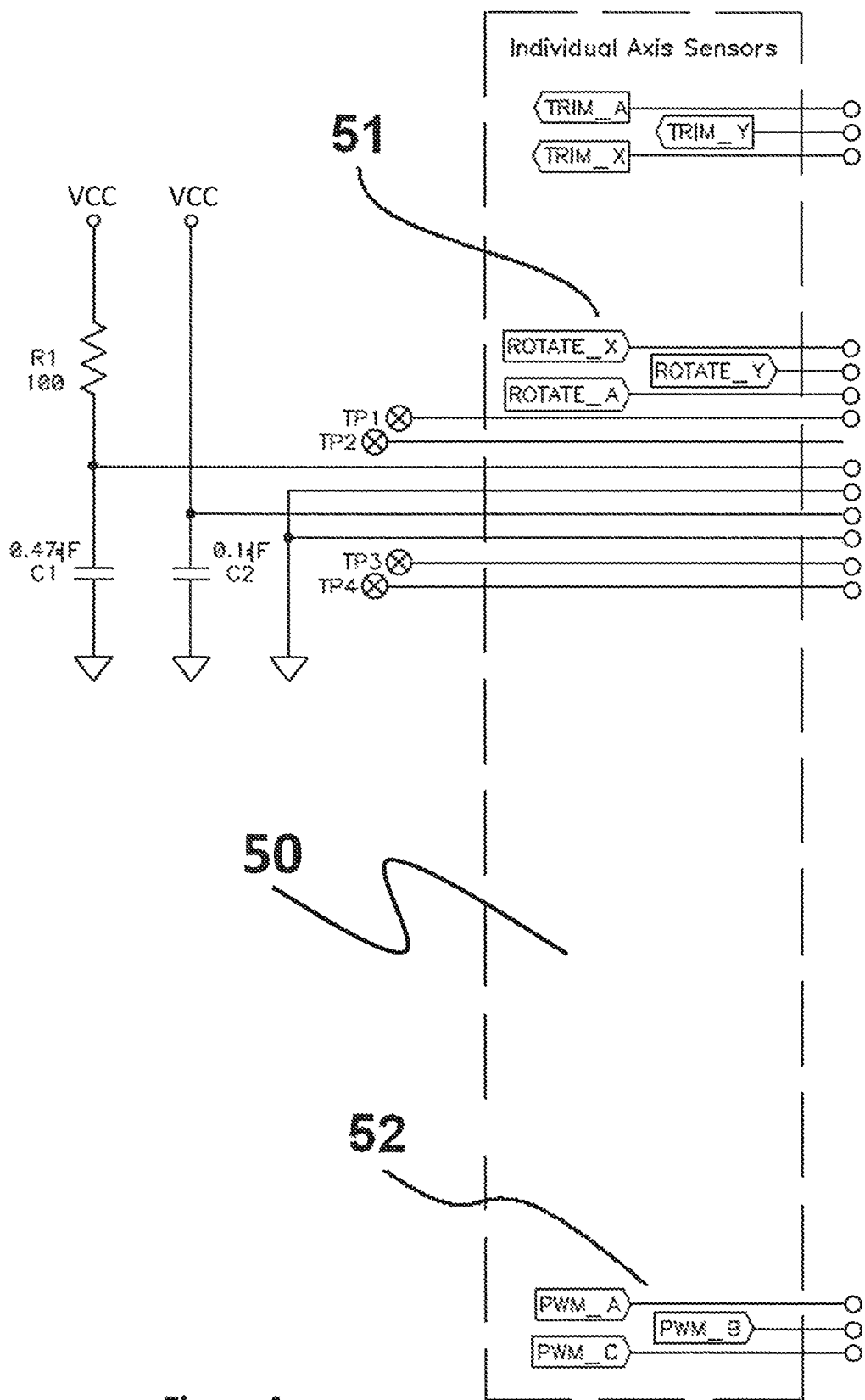
FIGS. 4a-4c. Electronic Schematic of the Subject Worn sensor board unit.
Figure 4B:
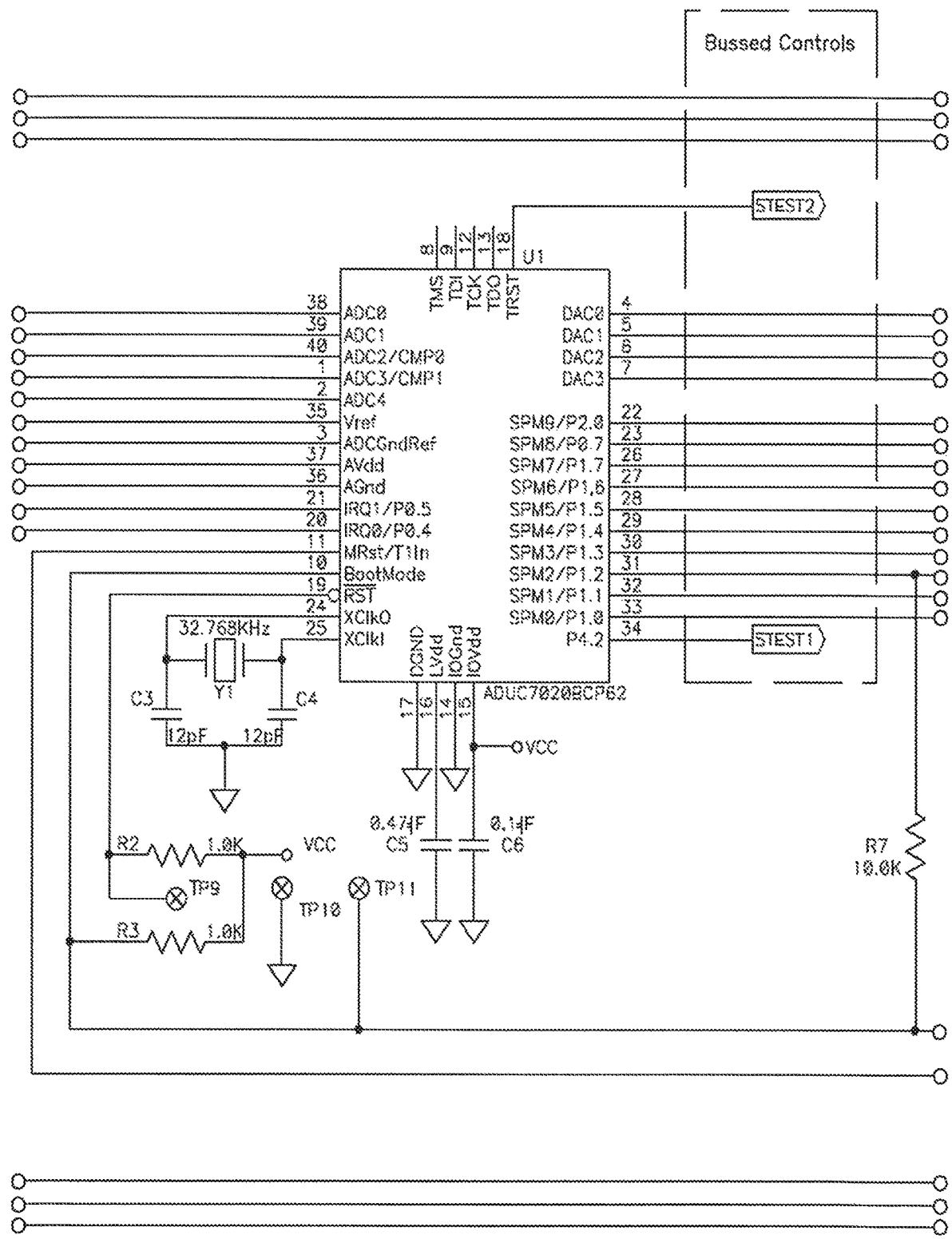
Figure 4C:
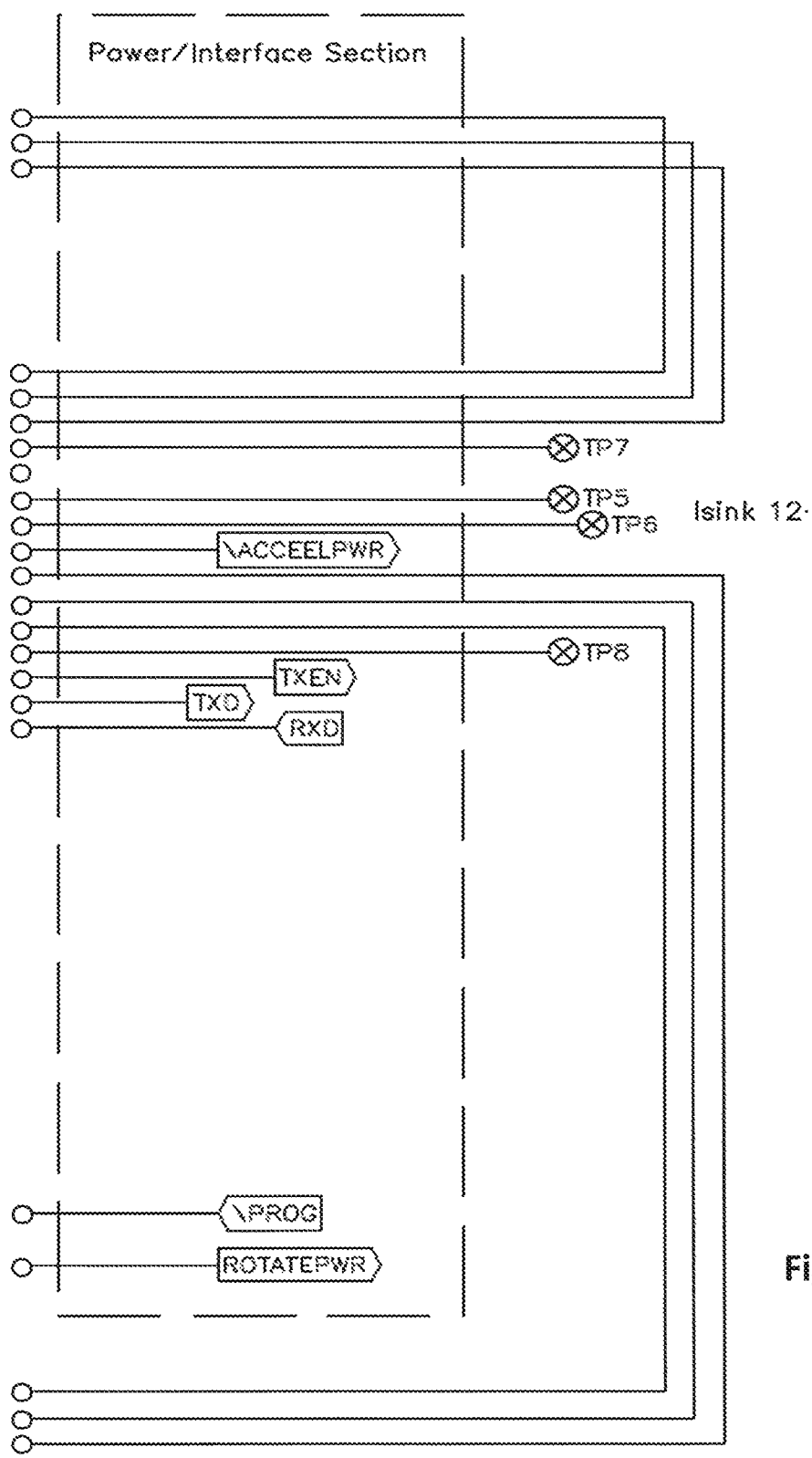

FIGS. 4a-4c illustrate an electrical schematic diagram for one embodiment of the subject worn sensor unit. FIG. 4a. shows a kinetic sensor board 50 (or subject worn external sensor) of the present invention. The kinetic sensor board 50 is preferably configured with both an accelerometer and a gyroscope for quantifying the subject's motion. In this particular embodiment, the kinetic sensor board 50 consists of three gyroscopes 51 and three orthogonal accelerometers 52. The kinetic sensor board also includes a microprocessor (Texas Instruments mSP430-169) and a power interface section.

Figure 5:
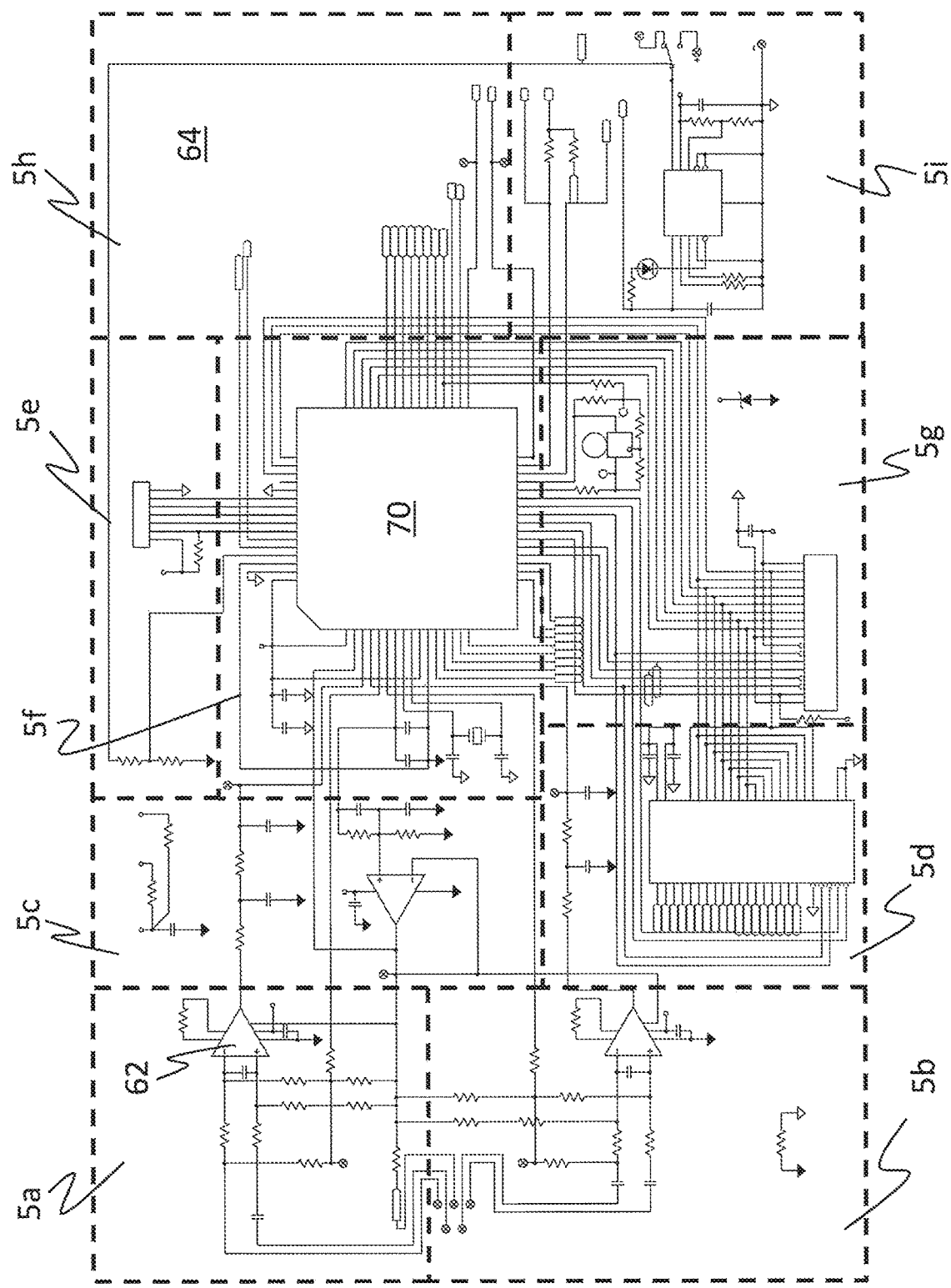
FIG. 5. Electronic Schematic of the Subject Worn transceiver module unit.
Figure 5A:
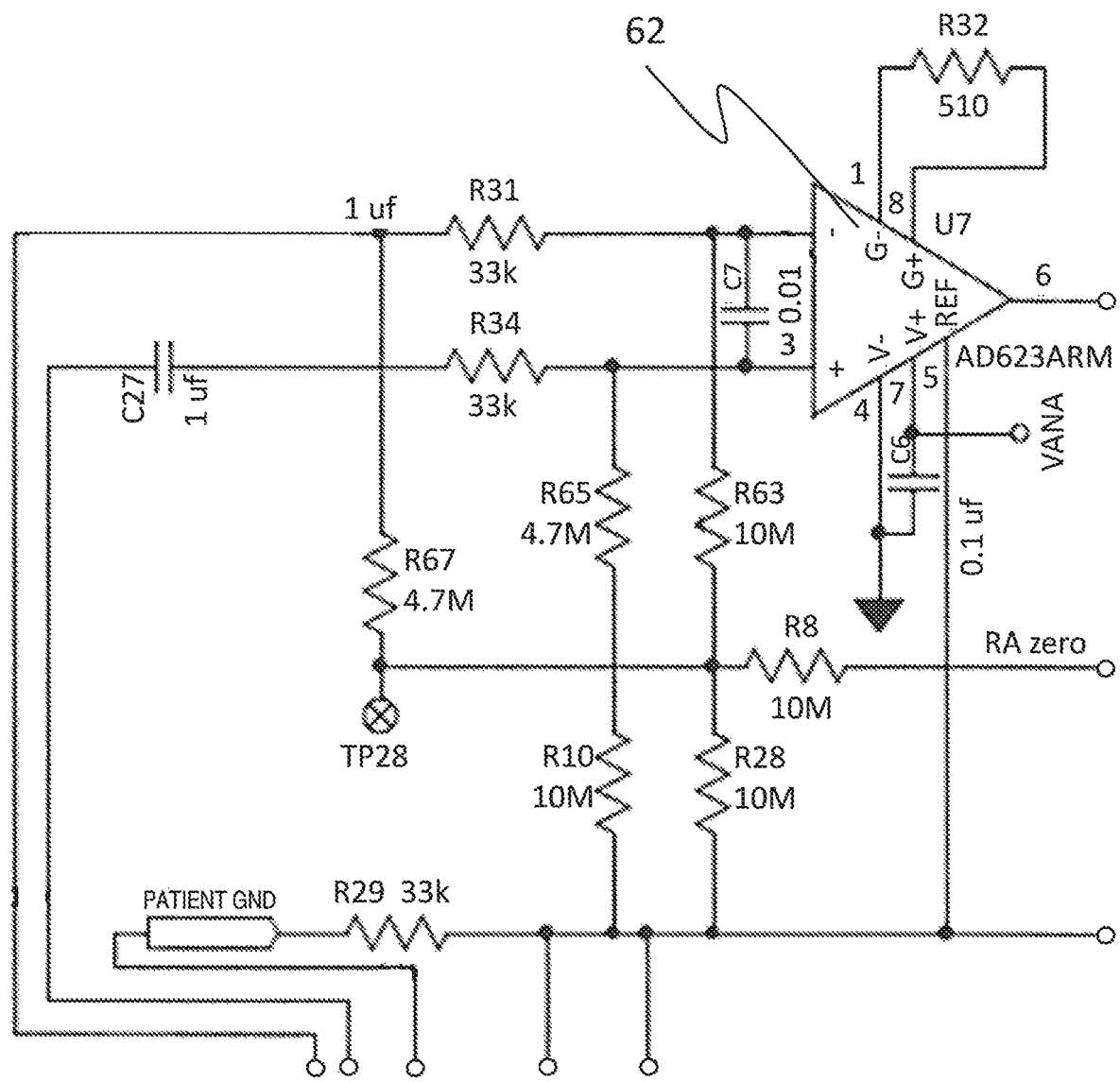
FIGS. 5a-5i. Exploded views of various sections of the Electronic Schematic of the Subject Worn transceiver module unit.
Figure 5B:
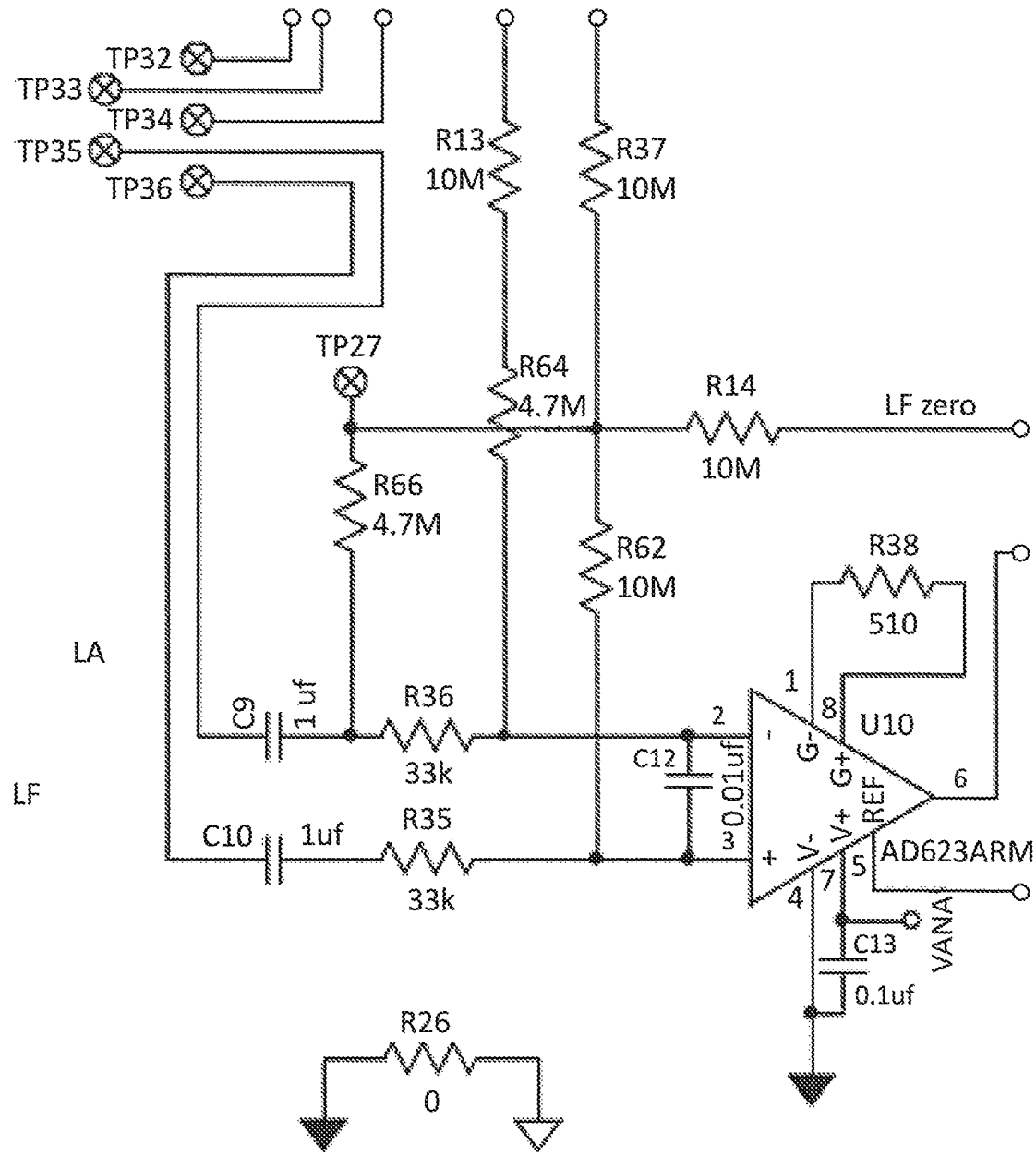
Figure 5C:
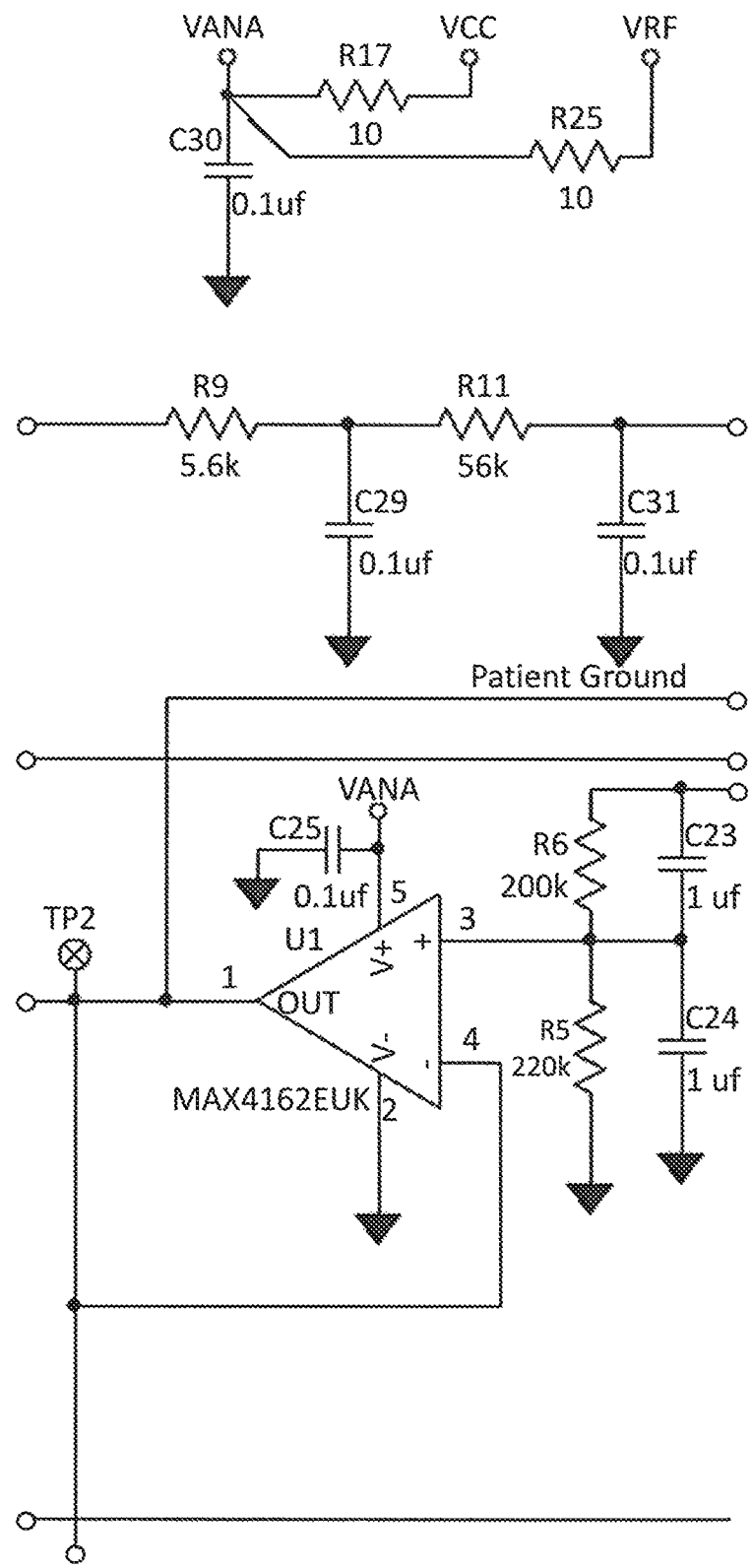
Figure 5D:
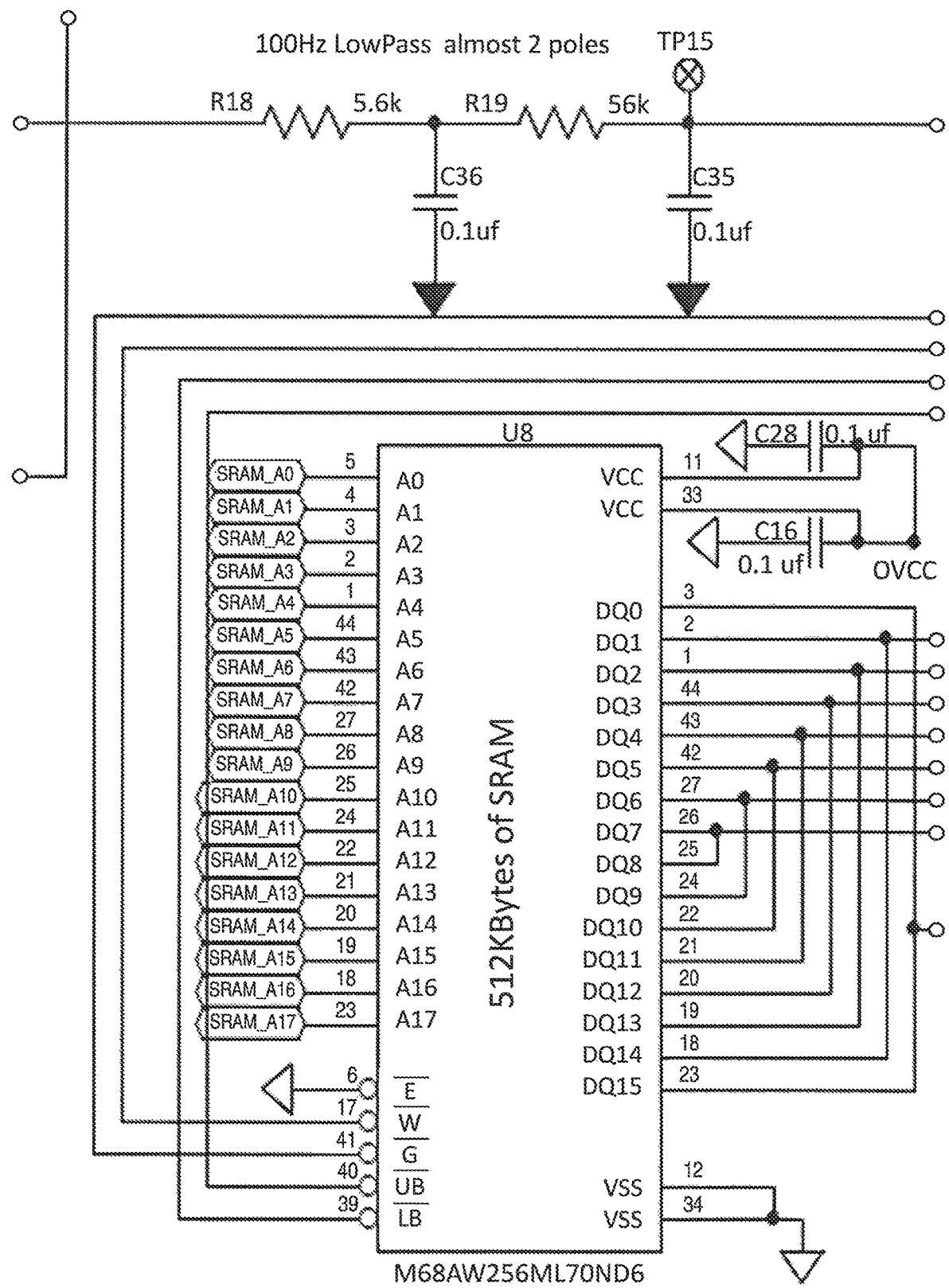
Figure 5E:
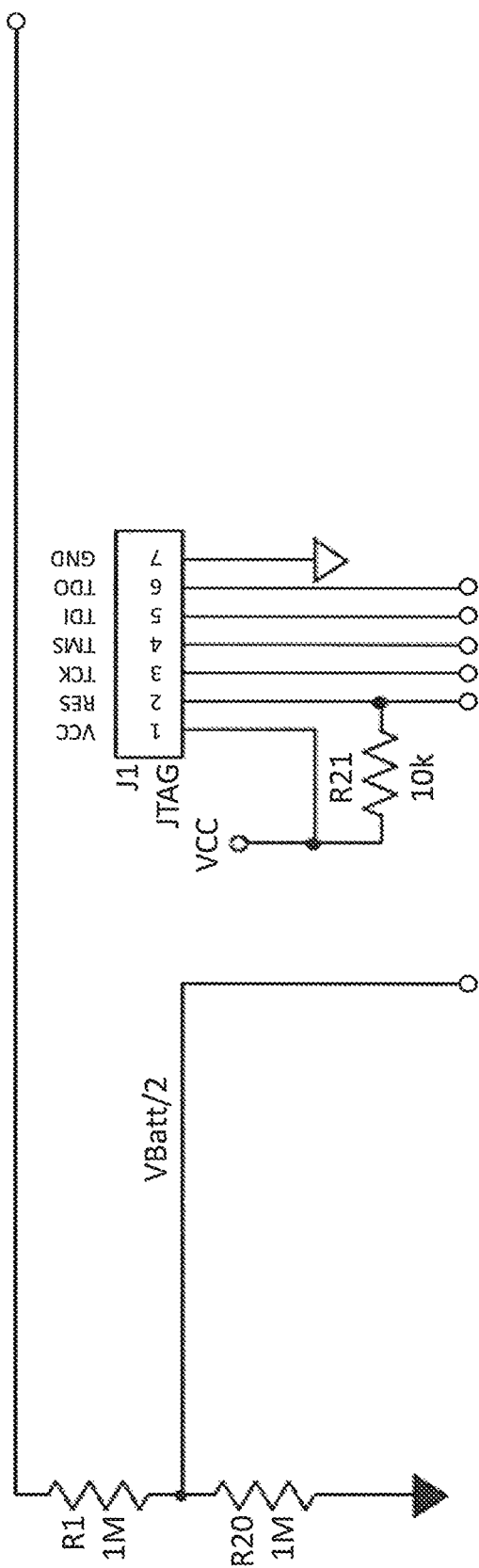
Figure 5F:
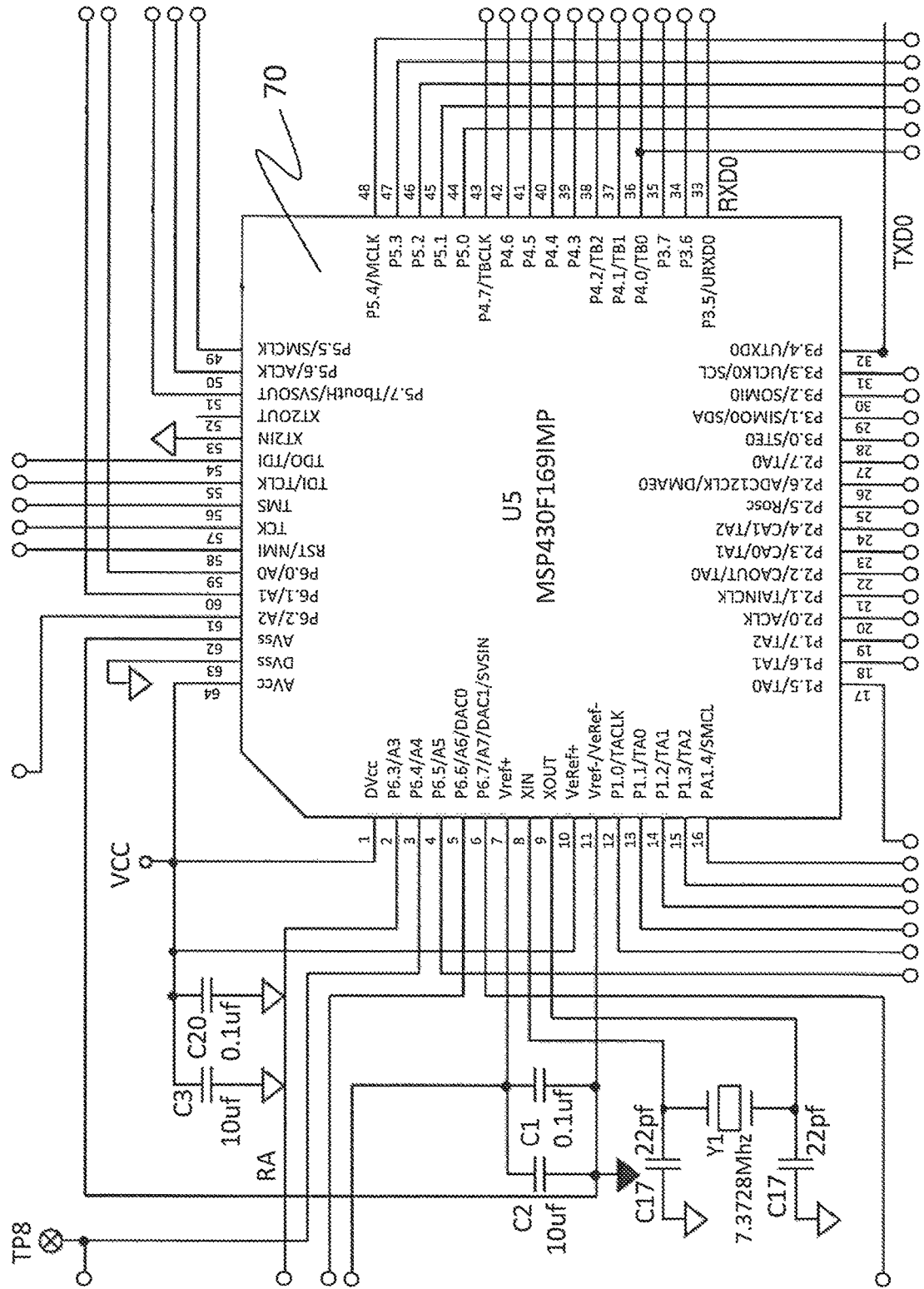
Figure 5G:
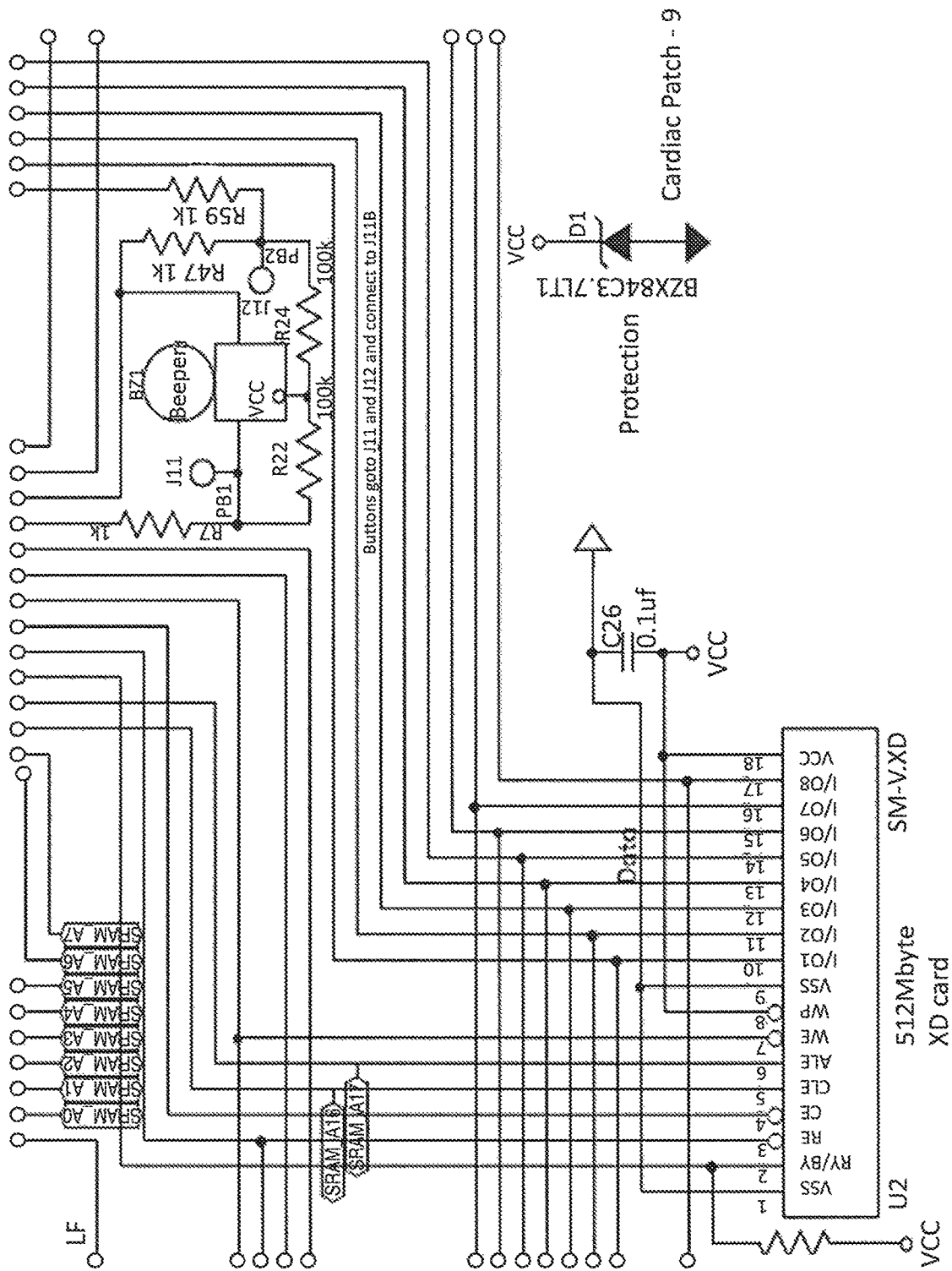
Figure 5H:
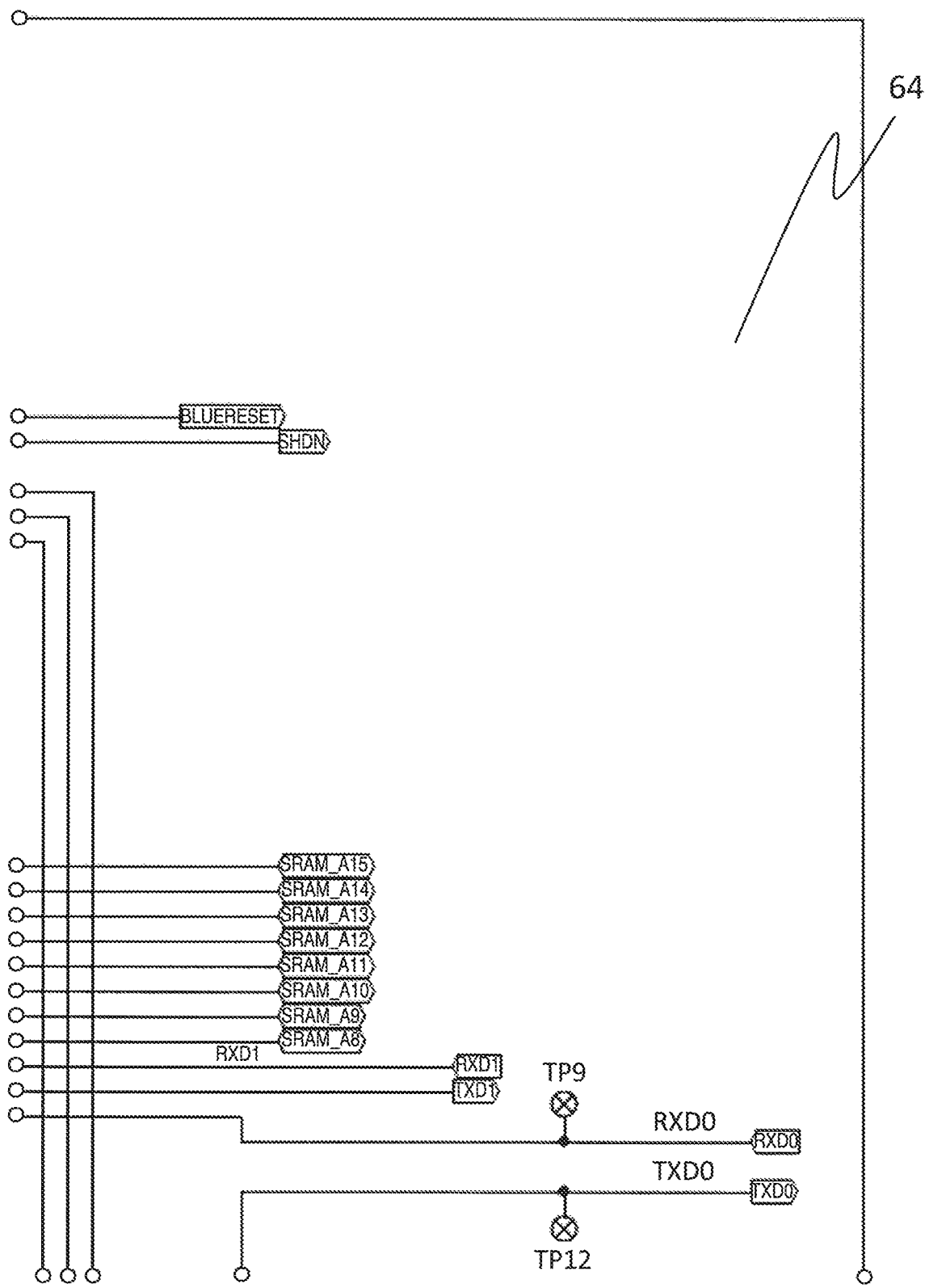
Figure 5I:
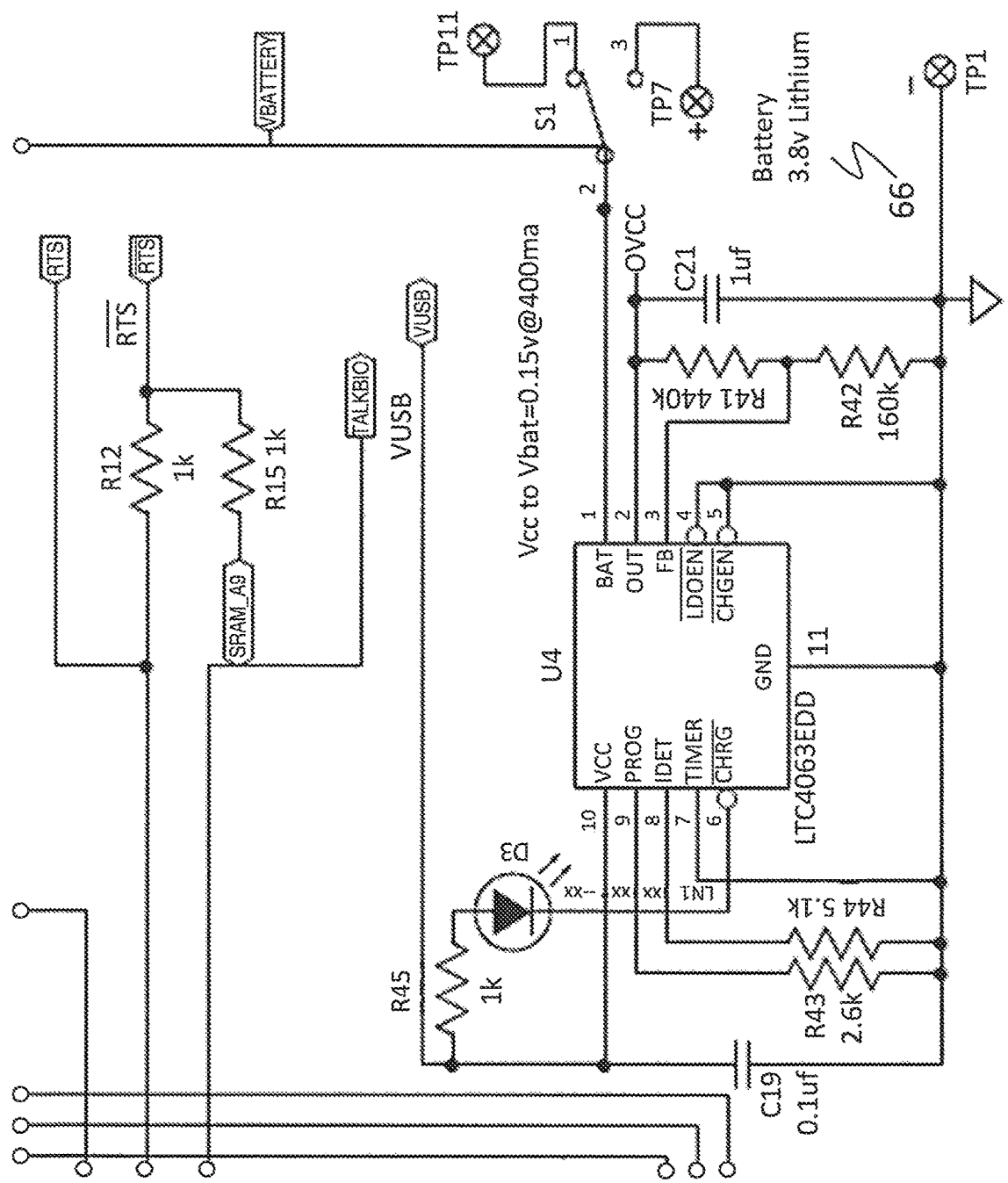

FIG. 5 is an electrical schematic diagram for one embodiment of the subject worn transceiver module 64. Exploded views of various sections of the electrical schematic diagram are shown in FIGS. 5*a*-5*i*. The transceiver module includes a blue tooth radio (EB100 A7 Engineering) to provide wireless communications with the subject PC, EMG amplifier and data acquisition circuitry, on board memory, a microprocessor 70, FIGS. 5 and 5*f*, (Analog Devices ADVC7020), and a battery power supply (lithium powered) 66, FIG. 5*i* that supplies power to both the transceiver module 64, FIG. 5*h*, and one or more external sensor modules 50. The transceiver module also includes a USB port to provide battery recharging and serial communications with the subject PC. The transceiver module also includes a push button input. The transceiver module also includes a limo connector to attached EMG electrode leads to the module.

Figure 6:
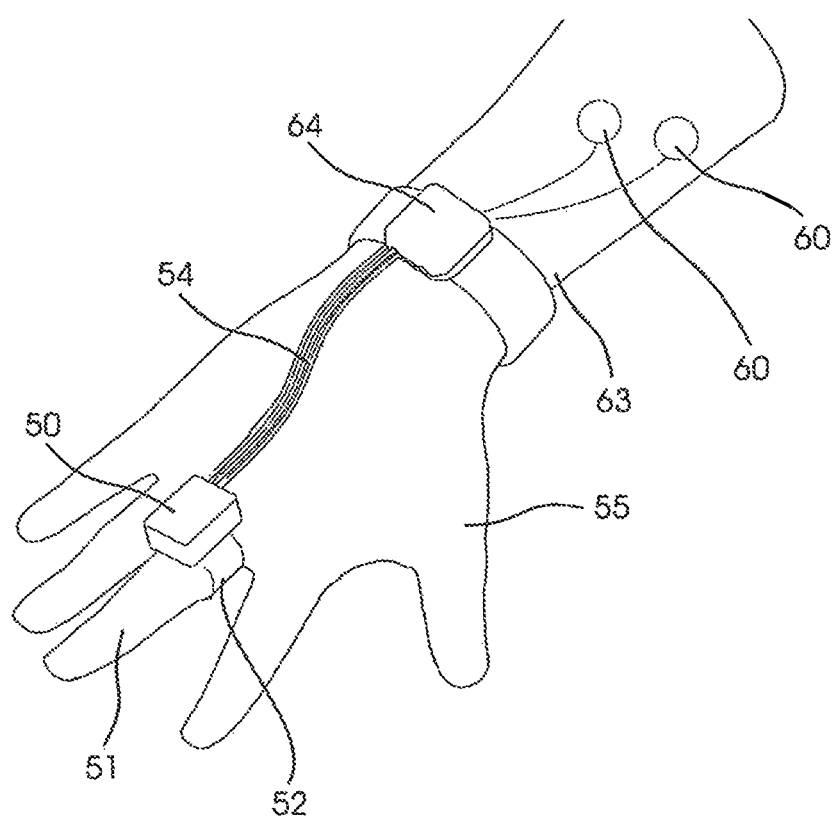
FIG. 6. Schematic showing placement of various components of the movement disorder device with an external sensor module for the hand and EMG electrodes.

FIG. 6 illustrates one possible embodiment of the subject 55 worn components of the system combining the sensor board 50 and the transceiver module 64. The sensor board 50 is worn on the subject's 55 finger 51 and the transceiver module 64 is worn on the subject's 55 wrist 63. The transceiver module 64 and one or more external sensor modules 50 are connected by a thin multi-wire leads 54. The transceiver module 64 in this embodiment connects to one or more electrodes 60 used to measure EMG.

Figure 7:
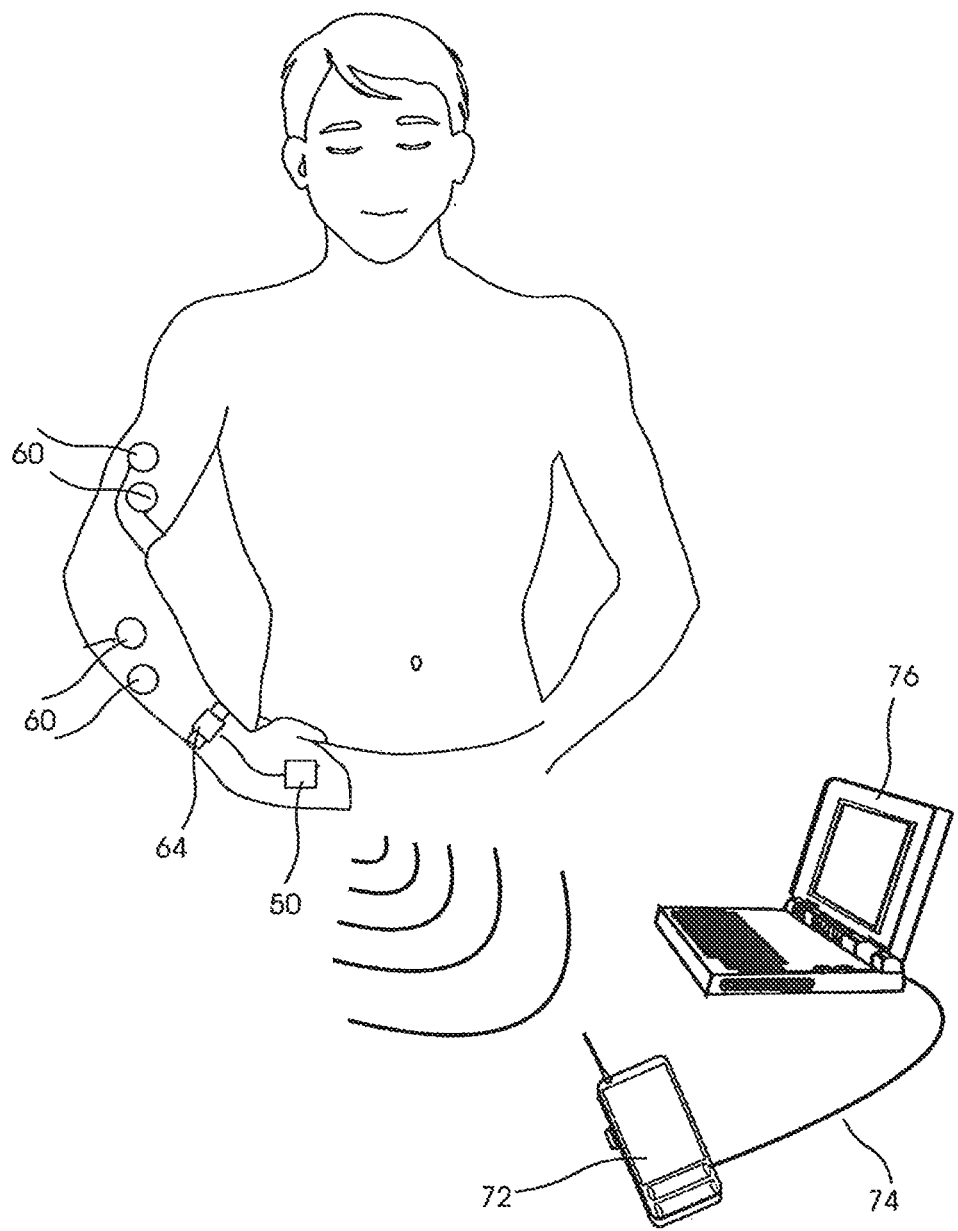
FIG. 7. Schematic showing various system components of the movement disorder device.

FIG. 7 illustrates one embodiment of the system components of the wireless movement disorder monitor. The external sensor module 50 in this embodiment contains three orthogonal accelerometers (not shown) and three orthogonal gyroscopes (not shown). This input to the external sensor module 50 consists of the kinetic forces applied by the user and measured by the accelerometers and gyroscopes. The output from the board is linear acceleration and angular velocity data in the form of output voltages. These output voltages are input to the transceiver module 64. These voltages undergo signal conditioning and filtering before sampling by an analog to digital converter. This digital data is then stored in on board memory and/or transmitted as a packet in RF transmission by a blue tooth transceiver. Additionally, EMG electrodes 60 worn by the subject may be input to the transceiver module. An amplifier on the transceiver module 64 amplifies the EMG signal(s) before signal conditioning, filtering, and sampling by the analog to digital converter. The EMG data is also stored in the on board memory and/or contained in the packet for RF transmission. A microprocessor (not shown) in the transceiver module 64 controls the entire process. Kinetic and EMG data packets may be sent by RF transmission to a nearby computer transceiver 72 which receives the data using an embedded blue tooth radio to a computer 76. Kinetic and EMG data may also be stored on the on board memory and downloaded to a computer 76 at a later time. The computer 76 then processes, analyzes, and stores the data. The kinetic sensor board 50 measures accelerations along and angular velocities about each of three orthogonal axes. The signals from the accelerometers and gyroscopes of the kinetic sensor board 50 are preferably input into a processor for signal conditioning and filtering. Preferably, three Analog Devices gyroscopes (ADXRS300) were utilized on the kinetic sensor board with an input range up to 1200 degrees/second. The Analog Devices parts were selected after an analysis of cost, size and power consumption. The ball grid array type of component was selected to minimize size. Additionally, a MEMS technology dual axis accelerometer, from Analog Devices (ADXL210), was employed to record accelerations along the x and y-axes. The sensors provide 80 dB dynamic range, low noise (1 mg/sqrt (Hz)), and low power (<2 mA per axis) in a surface mount package. Other combinations of accelerometers and gyroscopes known to those skilled in the art could also be used. A lightweight plastic housing was then used to house the sensor for measuring the subject's external body motion. The external body motion sensor(s) can be worn on the subject's finger, hand, wrist, fore arm, upper arm, head, chest, back, legs, feet and/or toes.

Various embodiments of the present invention may include a sensor(s) for measuring the subject's electrical muscle activity through techniques such as electromyography (EMG) or the like. FIG. 7 shows the EMG electrodes 60 which are connected to an amplifier 62. With an EMG sensor, a voltage difference or difference in electrical potential is measured between at least two recording electrodes. The electrodes used can be any type known to those skilled in the art including both indwelling (needle), surface and dry electrodes. Typical EMG electrodes connections may have an impedance in the range of from 5 to 10 K ohms. It is in general desirable to reduce such impedance levels to below 2 K ohms. Therefore a conductive paste or gel may be applied to the electrode to create a connection with an impedance below 2 K ohms. Alternatively, the subject(s) skin may be mechanically abraded, the electrode may be amplified or a dry electrode may be used. Dry physiological recording electrodes of the type described in U.S. patent application Ser. No. 09/949,055 are herein incorporated by reference. Dry electrodes provide the advantage that there is no gel to dry out and no skin to abrade or clean. Additionally if electrodes are used as the sensor(s), preferably at least three electrodes are used—two signal electrodes and one reference electrode.

Preferably, the transceiver module 64 contains one or more electronic components such as the microprocessor 70 for detecting both the signals from the gyroscopes 51 and accelerometers 52, and for detecting the signal from EMG electrode 60. Preferably, the one or more electronic components also filter (and possibly amplify) the detected EMG signals and kinetic motion signals, and more preferably convert these signals, which are in an analog form into a digital signal for transmission to the remote receiving unit. The one or more electronic components are attached to the subject as part of device or system. Further preferably, the one or more electronic components can receive a signal from the remote receiving unit or other remote transmitters. The one or more electronic components may include circuitry for but are not limited to for example electrode amplifiers, signal filters, analog to digital converter, blue tooth radio, a DC power source and combinations thereof. The one or more electronic components may comprise one processing chip, multiple chips, single function components or combinations thereof, which can perform all of the necessary functions of detecting a kinetic or physiological signal from the electrode, storing that data to memory, uploading data to a computer through a serial link, transmitting a signal corresponding to a kinetic or physiological signal to a receiving unit and optionally receiving a signal from a remote transmitter. These one or more electronic components can be assembled on a printed circuit board or by any other means known to those skilled in the art. Preferably, the one or more electronic components can be assembled on a printed circuit board or by other means so its imprint covers an area less than 4 in$^2$, more preferably less than 2 in$^2$, even more preferably less than 1 in$^2$, still even more preferably less than 0.5 in$^2$, and most preferably less than 0.25 in$^2$.

Preferably, the circuitry of the one or more electronic components is appropriately modified so as to function with any suitable miniature DC power source. More preferably, the DC power source is a battery. The most preferred battery of the present invention is lithium powered batteries. Lithium ion batteries offer high specific energy (the number of given hours for a specific weight), which is preferable. Additionally, these commercially available batteries are readily available and inexpensive. Other types of batteries include but are not limited to primary and secondary batteries. Primary batteries are not rechargeable since the chemical reaction that produces the electricity is not reversible. Primary batteries include lithium primary batteries (e.g., lithium/thionyl chloride, lithium/manganese dioxide, lithium/carbon monofluoride, lithium/copper oxide, lithium/iodine, lithium/silver vanadium oxide and others), alkaline primary batteries, zinc-carbon, zinc chloride, magnesium/manganese dioxide, alkaline-manganese dioxide, mercuric oxide, silver oxide as well as zinc/air and others. Rechargeable (secondary) batteries include nickel-cadmium, nickel-zinc, nickel-metal hydride, rechargeable zinc/alkaline/manganese dioxide, lithium/polymer, lithium-ion and others.

In some preferred embodiments, the system is capable of inductive charging whereby an electromagnetic field is used to transfer energy from a charging mat or pad to the device. Preferably in such embodiments, the charging mat or pad comprises and induction coil that is used to create an alternating electromagnetic field. When the device, also comprising an induction coil, is placed on the charging mat or pad, the devices induction coil draws power from the electromagnetic field created by the charging mat's or pad's induction coil. The device's then converts this drawn power from electromagnet field energy into electrical current and uses this electrical current to charge the device's battery.

Preferably, the circuitry of the one or more electronic components comprises data acquisition circuitry further including an amplifier that amplifies the EMG, (The gyroscope and accelerometer signals will not need to be amplified.). The data acquisition circuitry is designed with the goal of reducing size, lowering (or filtering) the noise, increasing the DC offset rejection and reducing the system's offset voltages. The data acquisition circuitry may be constrained by the requirements for extremely high input impedance, very low noise and rejection of very large DC offset and common-mode voltages, while measuring a very small signal of interest. Additional constraints arise from the need for a "brick-wall" style input protection against ESD and EMI. The exact parameters of the design, such as input impedance, gain and passband, can be adjusted at the time of manufacture to suit a specific application via a table of component values to achieve a specific full-scale range and passband.

More preferably, a low-noise, lower power instrumentation amplifier is used. The inputs for this circuitry is guarded with preferably, external ESD/EMI protection, and very high-impedance passive filters to reject DC common-mode and normal-mode voltages. Still preferably, the instrumentation amplifier gain can be adjusted from unity to approximately 100 to suit the requirements of a specific application. If additional gain is required, it preferably is provided in a second-order anti-bias filter, whose cutoff frequency can be adjusted to suit a specific application, with due regard to the sampling rate. Still preferably, the reference input of the instrumentation amplifier is tightly controlled by a DC cancellation integrator servo that uses closed-loop control to cancel all DC offsets in the components in the analog signal chain to within a few analog-to digital converter (ADC) counts of perfection, to ensure long term stability of the zero reference.

Preferably, the signals are converted to a digital form. This can be achieved with an electronic component or processing chip through the use of an ADC. More preferably, the ADC restricts resolution to 16-bits due to the ambient noise environment in such chips. Despite this constraint, the ADC remains the preferable method of choice for size-constrained applications such as with the present invention unless a custom data acquisition chip is used because the integration reduces the total chip count and significantly reduces the number of interconnects required on the printed circuit board.

Preferably, the circuitry of the sensor board comprises a digital section. More preferably, the heart of the digital section of the sensor board is the Texas Instruments MSP430-169 microcontroller. The Texas Instruments MSP430-169 microcontroller contains sufficient data and program memory, as well as peripherals which allow the entire digital section to be neatly bundled into a single carefully programmed processing chip. Still preferably, the onboard counter/timer sections are used to produce the data acquisition timer.

Preferably, the circuitry of the transceiver module comprises a digital section. More preferably, the heart of the digital section of the sensor board is the Analog Devices ADVC7020 microcontroller. The Analog Devices ADVC7020 microcontroller contains sufficient data and program memory, as well as peripherals which allow the entire digital section to be neatly bundled into a single carefully programmed processing chip. Still preferably, the onboard counter/timer sections are used to produce the data acquisition timer.

Preferably, the circuitry for the one or more electronic components is designed to provide for communication with external quality control test equipment prior to sale, and more preferably with automated final test equipment. In order to supply such capability without impacting the final size of the finished unit, one embodiment is to design a communications interface on a separate PCB using the SPI bus with an external UART and level-conversion circuitry to implement a standard serial interface for connection to a personal computer or some other form of test equipment. The physical connection to such a device requires significant PCB area, so preferably the physical connection is designed to keep the PCB at minimal imprint area. More preferably, the physical connection is designed with a break-off tab with fingers that mate with an edge connector. This allows all required final testing and calibration, including the programming of the processing chip memory, can be carried out through this connector, with test signals being applied to the analog inputs through the normal connections which remain accessible in the final unit. By using an edge fingers on the production unit, and an edge connector in the production testing and calibration adapter, the system can be tested and calibrated without leaving any unnecessary electronic components or too large an PCB imprint area on the final unit.

Preferably, the circuitry for the one or more electronic components comprises nonvolatile, rewriteable memory. Alternatively, if the circuitry for the one or more electronic components doesn't comprise nonvolatile, rewriteable memory then an approach should be used to allow for reprogramming of the final parameters such as radio channelization and data acquisition and scaling. Without nonvolatile, rewriteable memory, the program memory can be programmed only once. Therefore one embodiment of the present invention involves selective programming of a specific area of the program memory without programming the entire memory in one operation. Preferably, this is accomplished by setting aside a specific area of program memory large enough to store several copies of the required parameters. Procedurally, this is accomplished by initially programming the circuitry for the one or more electronic components with default parameters appropriate for the testing and calibration. When the final parameters have been determined, the next area is programmed with these parameters. If the final testing and calibration reveals problems, or some other need arises to change the values, additional variations of the parameters may be programmed. The firmware of various embodiments of the present invention scans for the first blank configuration block and then uses the value from the preceding block as the operational parameters. This arrangement allows for reprogramming of the parameters up to several dozen times, with no size penalty for external EEPROM or other nonvolatile RAM. The circuitry for the one or more electronic components has provisions for in-circuit programming and verification of the program memory, and this is supported by the breakoff test connector. The operational parameters can thus be changed up until the time at which the test connector is broken off just before shipping the final unit. Thus the manufacturability and size of the circuitry for the one or more electronic components is optimized.

Preferably the circuitry of the one or more electronic components includes an RF transmitter. Still preferably includes a blue tooth radio system utilizing the EB100 component from A7 engineering. Another feature of the circuitry of the one or more electronic components preferably is an antenna. The antenna, preferably, is integrated in the rest of the circuitry. The antenna can be configured in a number of ways, for example as a single loop, dipole, dipole with termination impedance, logarithmic-periodic, dielectric, strip conduction or reflector antenna. The antenna is designed to include but not be limited to the best combination of usable range, production efficiency and end-system usability. Preferably, the antenna consists of one or more conductive wires or strips, which are arranged in a pattern to maximize surface area. The large surface area will allow for lower transmission outputs for the data transmission. The large surface area will also be helpful in receiving high frequency energy from an external power source for storage. Optionally, the radio transmissions of the present invention may use frequency-selective antennas for separating the transmission and receiving bands, if a RF transmitter and receiver are used on the electrode patch, and polarization-sensitive antennas in connection with directional transmission. Polarization-sensitive antennas consist of, for example, thin metal strips arranged in parallel on an insulating carrier material. Such a structure is insensitive to or permeable to electromagnetic waves with vertical polarization; waves with parallel polarization are reflected or absorbed depending on the design. It is possible to obtain in this way, for example good cross polarization decoupling in connection with linear polarization. It is further possible to integrate the antenna into the frame of a processing chip or into one or more of the other electronic components, whereby the antenna is preferably realized by means of thin film technology. The antenna can serve to just transfer data or for both transferring data to and for receiving control data received from a remote communication station which can include but is not limited to a wireless relay, a computer or a processor system. Optionally, the antenna can also serve to receive high-frequency energy (for energy supply or supplement). In any scenario, only one antenna is required for transmitting data, receiving data and optionally receiving energy. Optionally, directional couples can be arranged on the transmitter outputs of the electrode patch and/or the remote communication station. The couplers being used to measure the radiated or reflected radio wave transmission output. Any damage to the antenna (or also any faulty adaptation) thus can be registered, because it is expressed by increased reflection values.

An additional feature of the present invention is an optional identification unit. By allocating identification codes—a subject code, the remote communication station is capable of receiving and transmitting data to several subjects, and for evaluating the data if the remote communication station is capable of doing so. This is realized in a way such that the identification unit has control logic, as well as a memory for storing the identification codes. The identification unit is preferably programmed by radio transmission of the control characters and of the respective identification code from the programming unit of the remote communication station to the subject worn unit. More preferably, the unit comprises switches as programming lockouts, particularly for preventing unintentional reprogramming.

In any RF link, errors are an unfortunate and unavoidable problem. Analog systems can often tolerate a certain level of error. Digital systems, however, while being inherently much more resistant to errors, also suffer a much greater impact when errors occur. Thus the present invention when used as a digital system, preferably includes an error control sub architecture. Preferably, the RF link of the present invention is digital. RF links can be one-way or two-way. One-way links are used to just transmit data. Two-way links are used for both sending and receiving data.

If the RF link is one-way error control, then this is preferably accomplished at two distinct levels, above and beyond the effort to establish a reliable radio link to minimize errors from the beginning. At the first level, there is the redundancy in the transmitted data. This redundancy is performed by adding extra data that can be used at the remote communication station or at some station to detect and correct any errors that occurred during transit across the airwaves. This mechanism known as Forward Error Correction (FEC) because the errors are corrected actively as the signal continues forward through the chain, rather than by going back to the transmitter and asking for retransmission. FEC systems include but are not limited to Hamming Code, Reed-Solomon and Golay codes. Preferably, a Hamming Code scheme is used. While the Hamming Code scheme is sometimes maligned as being outdated and underpowered, the implementation in certain embodiments of the present invention provides considerable robustness and extremely low computation and power burden for the error correction mechanism. FEC alone is sufficient to ensure that the vast majority of the data is transferred correctly across the radio link. Certain parts of the packet must be received correctly for the receiver to even begin accepting the packet, and the error correction mechanism in the remote communication station reports various signal quality parameters including the number of bit errors which are being corrected, so suspicious data packets can be readily identified and removed from the data stream.

Preferably, at a second, optional level, an additional line of defense is provided by residual error detection through the use of a cyclic redundancy check (CRC). The algorithm for this error detection is similar to that used for many years in disk drives, tape drives, and even deep-space communications, and is implemented by highly optimized firmware within the electrode patch processing circuitry. During transmission, the CRC is first applied to a data packet, and then the FEC data is added covering the data packet and CRC as well. During reception, the FEC data is first used to apply corrections to the data and/or CRC as needed, and the CRC is checked against the message. If no errors occurred, or the FEC mechanism was able to properly correct such errors as did occur, the CRC will check correctly against the message and the data will be accepted. If the data contains residual errors (which can only occur if the FEC mechanism was overwhelmed by the number of errors), the CRC will not match the packet and the data will be rejected. Because the radio link in this implementation is strictly one-way, rejected data is simply lost and there is no possibility of retransmission.

More preferably, the RF link utilizes a two-way (bi-directional) data transmission. By using a two-way data transmission the data safety is significantly increased. By transmitting redundant information in the data emitted by the electrodes, the remote communication station is capable of recognizing errors and request a renewed transmission of the data. In the presence of excessive transmission problems such as, for example transmission over excessively great distances, or due to obstacles absorbing the signals, the remote communication station is capable of controlling the data transmission, or to manipulate on its own the data. With control of data transmission it is also possible to control or re-set the parameters of the system, e.g., changing the transmission channel. This would be applicable for example if the signal transmitted is superimposed by other sources of interference then by changing the channel the remote communication station could secure a flawless and interference free transmission. Another example would be if the signal transmitted is too weak, the remote communication station can transmit a command to increase its transmitting power. Still another example would be the remote communication station to change the data format for the transmission, e.g., in order to increase the redundant information in the data flow. Increased redundancy allows transmission errors to be detected and corrected more easily. In this way, safe data transmissions are possible even with the poorest transmission qualities. This technique opens in a simple way the possibility of reducing the transmission power requirements. This also reduces the energy requirements, thereby providing longer battery life. Another advantage of a two-way, bi-directional digital data transmission lies in the possibility of transmitting test codes in order to filter out external interferences such as, for example, refraction or scatter from the transmission current. In this way, it is possible to reconstruct falsely transmitted data.

The remote communication station of various embodiments of the present invention can be any device known to receive RF transmissions used by those skilled in the art to receive transmissions of data. The remote communication station by way of example but not limitation can include a communications device for relaying the transmission, a communications device for re-processing the transmission, a communications device for re-processing the transmission then relaying it to another remote communication station, a computer with wireless capabilities, a PDA with wireless capabilities, a processor, a processor with display capabilities, and combinations of these devices. Optionally, the remote communication station can further transmit data both to another device and/or back. Further optionally, two different remote communication stations can be used, one for receiving transmitted data and another for sending data. For example, with the wireless movement disorder monitoring system of the present invention, the remote communication system of the present invention can be a wireless router, which establishes a broadband Internet connection and transmits the physiological signal to a remote Internet site for analysis, preferably by the subject's physician. Another example is where the remote communication system is a PDA, computer or cell phone, which receives the physiological data transmission, optionally re-processes the information, and re-transmits the information via cell towers, land phone lines or cable to a remote site for analysis. Another example is where the remote communication system is a computer or processor, which receives the data transmission and displays the data or records it on some recording medium, which can be displayed or transferred for analysis at a later time.

In many embodiments, information from the subject-worn device is preferably uploaded or otherwise made available to clinicians, researchers, or other end users by means of wired or wireless communication methods substantially instantly. Raw data, symptom quantification information, and any other data may be made immediately available to the end user for further analysis, review, or storage. The information may be instantly uploaded to a remote communication station, may be packaged and delivered directly to a specific end user or group of end users (for example by email), or, more preferably, may be instantly uploaded to a secure cloud-based server for storage. When the data is stored in a cloud-based server, the information is readily and immediately available to be accessed by verified end users who are authorized to gain access to the information while being securely stored and hidden from unauthorized users. This cloud-based system is particularly useful for clinical trials and other such studies. Using traditional movement disorder symptom analysis systems, as discussed throughout, subject data requires timely analysis and review, and then separate storing and collaboration of the information. For clinical trials, this timely process is multiplied by the number of subjects and the number of tests/sessions each subject performs. The present system instead provides automated symptom quantification information, and then immediately makes that information available to the end user. There is no lengthy period of time required for clinician analysis and scoring of the raw data, no need for numerous iterations of tests due to clinician and subject variability, and no need for manual entry of data. Instead, the present invention provides more accurate symptom quantification information and immediately makes that data available to the end user. Thus, the present invention can substantially decrease the number of subjects required to accurately and sufficiently provide required information for clinical trials. Additionally, the information or data may be immediately made available to a clinician who can diagnose or notice side effects that just took place, as opposed to later in time, and can ensure immediate compliance with the testing protocols. Still further, one clinician or end user may be able to more accurately and efficiently monitor numerous subjects without the need for intensive and unreliable subjective analysis of movement data. This last aspect has the added benefit of decreasing the amount and cost of travel for the subjects and clinicians, thus reducing the cost of care and/or clinical studies even further. Preferably, information is made available in real-time. By real-time, it is meant that preferably information is uploaded and made available in less than 30 minutes after completion of a test and calculation of symptom quantification. More preferably, information is uploaded and made available in less than 20 minutes after completion of a test and calculation of symptom quantification. Still more preferably, information is uploaded and made available in less than 15 minutes after completion of a test and calculation of symptom quantification. Yet more preferably, information is uploaded and made available in less than 10 minutes after completion of a test and calculation of symptom quantification. Even more preferably, information is uploaded and made available in less than 5 minutes after completion of a test and calculation of symptom quantification. Still yet more preferably, information is uploaded and made available in less than 1 minute after completion of a test and calculation of symptom quantification. Even yet more preferably, information is uploaded and made available in less than 45 seconds after completion of a test and calculation of symptom quantification. Yet still more preferably, information is uploaded and made available in less than 30 seconds after completion of a test and calculation of symptom quantification. Even still more preferably, information is uploaded and made available in less than 15 seconds after completion of a test and calculation of symptom quantification. Yet even more preferably, information is uploaded and made available in less than 10 seconds after completion of a test and calculation of symptom quantification. Still even more preferably, information is uploaded and made available in less than 5 seconds after completion of a test and calculation of symptom quantification. Still even yet more preferably, information is uploaded and made available in less than 1 second after completion of a test and calculation of symptom quantification. Yet even still more preferably, information is uploaded and made available in less than 0.5 second after completion of a test and calculation of symptom quantification. Most preferably, information is uploaded and made available substantially simultaneously with completion of a test and calculation of symptom quantification. Thus, the system may utilize a separate communication station to synchronize and communicate information with a remote communication station, but more preferably contains communication circuitry which can automatically, or semi-automatically send the information upon completion of a test. It is also important to note that the system preferably communicates data in a format which can be adapted or integrated into existing data structure systems such that no proprietary program, algorithm, or data structure is required to collect, analyze, and/or utilize the information. The data and information generated by the subject-worn device, and communicated to a cloud-based server or directly to an end user is compatible with, readily adapted to or integrated with currently existing data structures, or those later developed.

The digitized kinetic or physiological signal is then transmitted wirelessly to a remote communication station (FIG. 7). This remote communication station allows the subject wide movement. Preferably, the remote communication station can pick up and transmit signals from distances of greater than about 5 feet from the subject, more preferably greater than about 10 feet from the subject, even more preferably greater than about 20 feet from the subject, still even more preferably greater than about 50 feet from the subject, still even more preferably greater than about 200 feet from the subject, and most preferably greater than about 500 feet from the subject. The remote communication station is used to re-transmit the signal based in part from the physiological signal from the remote communication station wirelessly or via the internet to another monitor, computer or processor system. This allows the physician or monitoring service to review the subjects physiological signals and if necessary to make a determination, which could include modifying the subject's treatment protocols.

Optionally, the system of the present invention includes some form of instruction, which can be in written form on paper or on a computer monitor, or on a video. Preferably, a video is used which instructs the subjects to perform a series of tasks during which their kinetic motion and/or EMG can be measured. Since the system of the present invention is preferably used in the subject's home, a video giving directions and/or describing various tasks to be performed by the subject is included with the system. The video may be accessed or viewed for example but not by way of limitation through use of video tape, DVD, as part of computer software provided, through the internet, or the like. The directions could include but are not limited to instructions on how to don the device, how to turn the device on, and the like. The description of various tasks could include but is not limited to exercises which are typically used by a technician, clinician or physician to evaluate a subject with a movement disorder including but not limited to hand grasps, finger tapping exercises, other movements and the like. One embodiment of a video includes the technician, clinician or physician looking into the camera, as they would a subject, and instructing them on device setup, instructing the subjects through each of the tasks to be performed, providing verbal encouragement via video after a task, and asking subject's to repeat a task if it was not completed. Preferably, these video clips are edited and converted to a MPEG files using a Pinnacle Studios digital video system that includes a fire-wire card and editing software. For movement disorders such as Parkinson's disease preferably the technician, clinician or physician instructs the user through multiple tasks as per the UPDRS guidelines including but not limited to rest tremor, postural tremor, action tremor, all bradykinesia tasks (including but not limited to finger taps, hand grasps, and pronation/supination tasks), and/or rigidity tasks. More preferably, if the video is linked to the user interface software, the software will automatically detect if a subject has performed the requested task and provide feedback through the video to either repeat the task or continue to the next task.

Existing systems largely use interactive, observation-based methods in which clinicians or other trained individuals, as well as the subjects themselves, observe and report on the subject's symptoms and provide a subjective score relating to a quantification of the symptom severity. One such system that is widely accepted and known in the art is the Unified Parkinson's Disease Rating Scale (UPDRS) as mentioned above. The UPDRS comprises several sections, each relating to a different grouping of tests which relate to a particular group of symptoms of Parkinson's Disease. The several sections of the UPDRS include: Part 1—evaluation of mentation, behavior and mood; Part II—self-evaluation of the activities of daily life; Part III—evaluation of motor function (typically clinician-scored); Part IV—evaluation of complications of therapy; Part V—Hoehn and Yahr scale staging of the severity of Parkinson's Disease; and Part VI—Schwab and England Activities of Daily Living scale. Each part either requires the clinician to observe the subject's symptoms, or for the subject to self-score the severity of symptoms and record his or perception of the symptoms for the clinician to later evaluate the information. Each part is comprised of a number of different tests or activities, and each test or activity receives a score. This score relates to the perceived or observed severity of the symptom being observed during a particular test or activity. The individual test or activity scores are then combined to provide an overall score for the particular section of the test, and a total UPDRS score is also provided combining the scores from each section. Each observation of a test or activity introduces several degrees of variability and subjectivity based on the evaluator's opinion of the information/data presented.

Many statistical metrics can be used to evaluate the reliability and repeatability of a scale such as the UPDRS. Several of the most commonly used and accepted metrics include standard error of measurement (SEM), minimal clinically important change or difference (MCIC/MCID), smallest detectable difference (SDD), fluctuation, intraclass correlation (ICC), and minimal detectable change (MDC). These metrics each provide a quantitative analysis of how statistically accurate a rating or scoring scale or system is, and thus provide measures of the reliability and accuracy of these scales and systems. The present invention aims to provide an automated system which is more accurate and reliable than currently known scales and systems.

Using any of these metrics to measure sensitivity, repeatability, or reliability of a system typically requires the repetition of at least one test, under circumstances that are as substantially similar as possible. Therefore, although in clinical practice tests may be repeated as infrequently as once a month (or sometimes longer), in order to measure the sensitivity, repeatability, or reliability of a system, it is often preferable to repeat the test(s) in a shorter period of time. For purposes of the present invention, this shorter time period specifically for measuring sensitivity, repeatability, or reliability of a system is referred to as real-time measurement, (e.g., real-time ICC, real-time MDC, and the like), and corresponds to any of the above or other metrics that may be used to assess the system. Preferably, for real-time system assessment, the test(s) are repeated within 4 hours. More preferably, for real-time system assessment, the test(s) are repeated within 3 hours. Still more preferably, for real-time system assessment, the test(s) are repeated within 2.5 hours. Yet more preferably, for real-time system assessment, the test(s) are repeated within 2 hours. Even more preferably, for real-time system assessment, the test(s) are repeated within 1.5 hours. Still yet more preferably, for real-time system assessment, the test(s) are repeated within 1 hour. Even yet more preferably, for real-time system assessment, the test(s) are repeated within 45 minutes. Yet still more preferably, for real-time system assessment, the test(s) are repeated within 30 minutes. Even still more preferably, for real-time system assessment, the test(s) are repeated within 20 minutes. Yet even more preferably, for real-time system assessment, the test(s) are repeated within 15 minutes. Still even more preferably for real-time system assessment, the test(s) are repeated within 10 minutes. Most preferably, for real-time system assessment, the test(s) are repeated substantially immediately upon completion of the previous test. The only significant limitation on how quickly the test(s) may be repeated in order to assess the system's sensitivity, repeatability, or reliability is the length of time it actually takes to perform a given test, and to repeat that test.

Standard error of measurement (SEM) estimates how repeated measurements by an instrument or clinician tend to be distributed and thus how the score varies from measurement to measurement. The formula for calculating SEM is presented in Equation 1:

$$SEM = SD \times \sqrt{1-r}. \qquad 1)$$

SD is the standard deviation of measurements, and r is the reliability coefficient, where the reliability coefficient represents the variability of the scores of the test and indicates the range of the scores that can be expected upon retesting.

Minimal clinically important change or minimal clinically important difference (MCIC/MCID) is described as the smallest difference that clinicians and/or subjects would care about or notice. This is a wholly subjective metric in that it is judged by the subject or by experts in the field, typically based on inputs from subjects. This metric focuses on the subject's perceived result from a given therapy or treatment and whether the result is significant enough to effect an actual discernible change in his or her function or life. The value for MCIC/MCID is typically determined based on the subject's input by way of questioning or observing the subject, or having the subject provide a report in some manner.

Intraclass correlation (ICC) is a statistical measure of the reliability of the rating or score scale or system in that it measures the agreement between groups of values, typically the values of the scores or ratings for a group of tests where each test in the group is a repeat of the first, and is conducted under the same or substantially identical circumstances—hence ICC is a measure of test-retest reliability. ICC can be used to assess test-retest reliability of a single observer (in the case of the present invention a single clinician or device for calculating symptom severity scores) or among several observers measuring the same quantity. The modern, and commonly accepted formula for calculation of ICC is presented in Equation 2:

$$r = \frac{K}{K-1} \times \frac{N^{-1} \cdot \sum_{n=1}^{N}(\bar{x}_n - \bar{x})^2}{s^2} - \frac{1}{K-1}. \qquad 2)$$

K is the number of data values per group compared, s is the standard deviation, and $\bar{x}_n$ is the sample mean of the $n^{th}$ group. Values for ICC (r) are typically positive value between 0 and 1 representing the ratio of total variance due to variation between groups. Thus, as the ICC value approaches 1, the system, test, metric, etc. is less variable and is more reliable and repeatable. For purposes of the present invention, the sample size for ICC measurements (i.e., number of iterations of the same movement disorder test, movement, activity or motion) is preferably at a minimum two, though is preferably higher. More preferably, at least three iterations of the movement disorder test are used to calculate the ICC for the given test. Still more preferably, at least four iterations of the movement disorder test are used to calculate the ICC for the given test. Yet more preferably, at least five iterations of the movement disorder test are used to calculate the ICC for the given test. Even more preferably, at least seven iterations of the movement disorder test are used to calculate the ICC for the given test.

Related to test-retest reliability is the minimal detectable change (MDC), the minimum amount of change on a rating scale or instrument that is not likely due to chance or variation in measurement. Score changes that are less than the MDC value are considered to be indistinguishable from measurement error, but score changes greater than the MDC can be attributed to the subject improvement rather than measurement error. Thus, if a subject's score change is greater than the MDC value, that subject is considered to noticeably benefit from the particular therapy or treatment which accounted for the change in score. MDC calculation is similar to that for SEM (see above), and formula for calculating MDC is presented in Equation 3:

$$MDC = z\text{-score}_{conf.level} \times SD_{baseline} \times \sqrt{2(1 - r_{test-retest})} \qquad 3)$$

The z-score is representative of the confidence interval from a normal distribution, SD is the standard deviation at baseline, and r is the test-retest reliability coefficient (sometimes ICC). Many in the art choose to use a confidence interval of 90%, while many others choose to use 95%. When a confidence interval of 95% is used, many of those skilled in the art define this increased precision MDC value as the smallest detectable change (SDD). The MDC (or SDD) values may be presented with varying units depending on the item, quantity, or value being measured. For example, if an overall section of the UPDRS (e.g., UPDRS-III, the motor section) is being scored and compared against other scores for the same section, then the MDS would have no units attached because the value being measured has no units—it is a raw score characterized by a positive integer. However, where a single test, event, quantity, etc. is being evaluated, for example a functional reach test (measured in centimeters) or ambulation tests (measured in distance (meters) or time (seconds)), the MDC value may have a unit attached representative of the units used to measure the results of the particular test. This stands to reason due to the nature of the MDC (or SDD) measurement which quantifies the minimal amount of change in those units that is detectable.

The above metrics may be used to measure a system's reliability and accuracy, particularly with regards to repeatability of results, and thus determine how sensitive a system is to variability in the underlying measurements. With respect to the present invention, it is preferable that the devices or methods meet certain thresholds for sensitivity to variability, and thus these metrics can be used to define acceptable levels of such sensitivity. In many embodiments, the present invention calculates a series of symptom quantification measures which can be calculated for any test or series of tests the subject performs. The symptom quantification metrics may be calculated for a single test (e.g., resting tremor, finger taps, hand movements, and the like), or across a series of tests (e.g. UPDRS-III as a whole, which combines the above individual tests with others). For the purpose of the present invention, a "test" is defines as any activity or action that the subject performs in order to gauge and measure the movement disorder symptoms present while performing said activity or action. Therefore, these symptom quantification measures may be used to measure the sensitivity of the system using the above metrics, and preferably the system meets a minimum threshold for sensitivity with respect to each metric. With respect to ICC, the present invention preferably provides symptom quantification measures for repeated tests with an ICC of at least about 0.50. More preferably, the present invention provides symptom quantification measures for repeated tests with an ICC of at least about 0.55. Still more preferably, the present invention provides symptom quantification measures for repeated tests with an ICC of at least about 0.60. Yet more preferably, the present invention provides symptom quantification measures for repeated tests with an ICC of at least about 0.63. Even more preferably, the present invention provides symptom quantification measures for repeated tests with an ICC of at least about 0.65. Still yet more preferably, the present invention provides symptom quantification measures for repeated tests with an ICC of at least about 0.67. Even still more preferably, the present invention provides symptom quantification measures for repeated tests with an ICC of at least about 0.70. Still even more preferably, the present invention provides symptom quantification measures for repeated tests with an ICC of at least about 0.73. Yet still more preferably, the present invention provides symptom quantification measures for repeated tests with an ICC of at least about 0.75. Even yet more preferably, the present invention provides symptom quantification measures for repeated tests with an ICC of at least about 0.77

With respect to MDC, the thresholds may vary widely depending on whether a single test, or a group of tests, is being performed and measured because the measurable units for each test may vary. Furthermore, the minimal detectable change value will be different for each individual test or set of tests. Some tests may have a scale of 0 to 4 while others may measure ranges from 1-100. Therefore, it may be preferable to measure the MDC of a given test based on the percentage of the overall scale for that particular test. Regardless of the test being performed, the present invention preferably provides symptom quantification measures for repeated tests with an MDC corresponding to about 35% or less of the total test score scale. More preferably, the present invention provides symptom quantification measures for repeated tests with an MDC corresponding to about 30% or less of the total test score scale. Yet more preferably, the present invention provides symptom quantification measures for repeated tests with an MDC corresponding to about 27% or less of the total test score scale. Still more preferably, the present invention provides symptom quantification measures for repeated tests with an MDC corresponding to about 25% or less of the total test score scale. Even more preferably, the present invention provides symptom quantification measures for repeated tests with an MDC corresponding to about 23% or less of the total test score scale. Still yet more preferably, the present invention provides symptom quantification measures for repeated tests with an MDC corresponding to about 20% or less of the total test score scale. Even yet more preferably, the present invention provides symptom quantification measures for repeated tests with an MDC corresponding to about 17% or less of the total test score scale.

The present invention includes various methods of measuring and scoring the severity of a subject's movement disorder. These methods include a number of steps which may include but are not limited to providing a device to a subject, the device comprising at least one sensor having a signal corresponding to a subject's external body motion associated with a movement disorder; measuring a subject's external body motion; transmitting a signal based in part on the subject's measured external body motion; receiving the transmitted signal; calculating substantially in real time with the processor a symptom quantification measure based at least in part on the signal from the at least one sensor; downloading data from memory; and scoring the severity of a subject's movement disorder based in part on the transmitted or downloaded signal. Optionally, an electromyogram of the subject's muscle activity may be obtained and used in part to score the severity of the subject's movement disorder.

The step of providing a device to a subject preferably refers to the various embodiments of a device as described herein. The device is preferably one used for measuring and quantifying the severity of a subject's movement disorder symptoms. This step may include providing instructions based on which the subject would be able to apply and remove the device so that it may be worn for testing and removed when not testing. In several embodiments, the device preferably has at least one sensor, though in many other embodiments the device preferably has at least two sensors, and in still other embodiments at least three sensors. In all embodiments, the sensors of the provided device have a signal wherein that signal corresponds to a perceived, measured or sensed movement of the subject's body. Preferably, the sensors correspond to external motion of the subject's body such that they perceive, measure or sense body movements that correspond to movement disorder symptoms.

Many embodiments further comprise a step of measuring the subject's external body motion with the device and the at least one, two, or three sensors of the device. For the purposes of the present invention, and specifically with regard to measuring the sensitivity of the device, the measurement of the subject's external body motion is preferably carried out while the subject is performing at least one test, activity, movement, or motion. Also preferably, the at least one test, activity, movement, or motion corresponds to a particular movement disorder test. By way of non-limiting example, Section III of the UPDRS proscribes various tests for the subject to perform in order for the clinician to score the severity of motor symptoms during those tasks, some of the tests include finger-tapping, heel tapping, standing up from a chair, and the like. Each of these tasks is considered a test and can be used to measure a different aspect, characteristic or symptom of the subject's potential movement disorder. Other scales and tests may be used for various movement disorders, or for different symptoms. Regardless of the test, activity, movement or motion performed, the device measures the subject's external body motion while it is being performed. Preferably, other surrounding factors and circumstances may be recorded as well, such as the time of day the test is performed, the time at which the last dose of medication was administered, and other environmental factors that would allow the test to be repeated under the most identical conditions possible at a later time. As the device, and more particularly the sensor(s) of the device measure the subject's external body motion, the sensor(s) transform the measurement into a signal which corresponds to the measured external body motion.

Many embodiments of the present invention further comprise a step of transmitting the signal from the sensor to a processor. The various methods and modalities by which the signal may be transmitted are described throughout, but the signal may be transmitted through hardwired communication, though is preferably transmitted wirelessly. The processor, as described in greater detail above, comprises various hardware and programs or algorithms for pre-processing and processing the signal(s) of the sensor(s). The signal(s) are transmitted from the sensor(s) to the processor so that the processor can carry out the required quantification steps described below.

Many embodiments of the present invention further include the step of quantifying the severity of the subject's movement disorder symptom. In many such embodiments, the quantification of a symptom is provided in the form of a symptom quantification measure or score. The scale of the symptom quantification measure or score depends on the particular type of sensor used, and the particular test, activity, movement or motion the subject is performing. Preferably calculation of the symptom quantification measure or score is performed by the processor substantially in real time. As disclosed herein, by real time, it is meant that the quantification measure or score is preferably calculated in less than about 30 minutes of the subject performing the test and the subject's external body motion being measured. More preferably, the quantification measure or score is preferably calculated in less than about 1 minute of the subject performing the test and the subject's external body motion being measured. Still more preferably, the quantification measure or score is preferably calculated in less than about 30 seconds of the subject performing the test and the subject's external body motion being measured. Yet more preferably, the quantification measure or score is preferably calculated in less than about 15 seconds of the subject performing the test and the subject's external body motion being measured. Even more preferably, the quantification measure or score is preferably calculated in less than about 10 seconds of the subject performing the test and the subject's external body motion being measured. Yet still more preferably, the quantification measure or score is preferably calculated in less than about 5 seconds of the subject performing the test and the subject's external body motion being measured. Even still more preferably, the quantification measure or score is preferably calculated in less than about 1 second of the subject performing the test and the subject's external body motion being measured. Still yet more preferably, the quantification measure or score is preferably calculated in less than about 0.1 seconds of the subject performing the test and the subject's external body motion being measured. Even yet more preferably, the quantification measure or score is preferably calculated in less than about 0.01 seconds of the subject performing the test and the subject's external body motion being measured. In all such embodiments, the processor calculates the symptom quantification measure or score based at least in part on the signal(s) received from the sensor(s) where said signal(s) correspond to the measured external body motion of the subject.

Many embodiments of the present invention, particularly those pertaining to the sensitivity and accuracy of the device and/or measurements, may require a further step(s) wherein at least one of the above steps are repeated as described. Some embodiments may utilize a single additional repetition of at least one of the above steps, though other embodiments may use multiple iterations. Most notably, the steps of measuring the subject's external body motion with the device comprising a sensor(s) while the subject performs a movement disorder test, activity, movement or motion, transmitting a signal from the sensor(s) to the processor, and calculating with the processor a symptom quantification measure or score are the steps most likely to be repeated at least once for the purposes of checking or determining the sensitivity of the device and/or methods. In such embodiments, the subject's external body motion is measured during the first movement disorder test, and the sensor(s) transmit a first signal to the processor which calculates a first symptom quantification measure or score based at least in part on the signal(s) received during or after the first test. Subsequently, the steps are repeated where the subject's external body motion is measured during a second movement disorder test, and the sensor(s) transmit a second signal to the processor which calculates a second symptom quantification measure or score based at least in part on the signal(s) received during or after the second test. It is possible to carry out this process in further iterations as well. When repeating a movement disorder test for the purpose of checking or determining the system's sensitivity, the second test is preferably performed under substantially identical circumstances as the first movement disorder test. For example, the subject should perform the exact same test or tests the second time that were performed the first time. Additionally, the second test is preferably performed as near to the same time of day as the first test, and at the same point in the subject's medication cycle (if the subject is on medication) as possible. That is, if the subject typically takes movement disorder-related medication upon awaking in the morning, and did so on the day of the first test, that habit or process should be repeated on the day of the second test. In other words, the circumstances surrounding the first and second tests should be as near to identical as possible in order to eliminate extra variables that may affect the results of the test in the form of symptom severity. The same holds true for any subsequent iterations of the testing procedure as well. The end result is that the two tests provide a basis on which the sensitivity of the system may be measured in order to determine how accurate, consistent, and repeatable measurement results are with the given device and methods. As discussed herein, sensitivity may be measured by various metrics including intraclass correlation (ICC), minimum detectable change (MDC), smallest detectable difference (SDD—often interchangeable with and MDC measurement with a 95% confidence interval), and the like.

Figure 8:
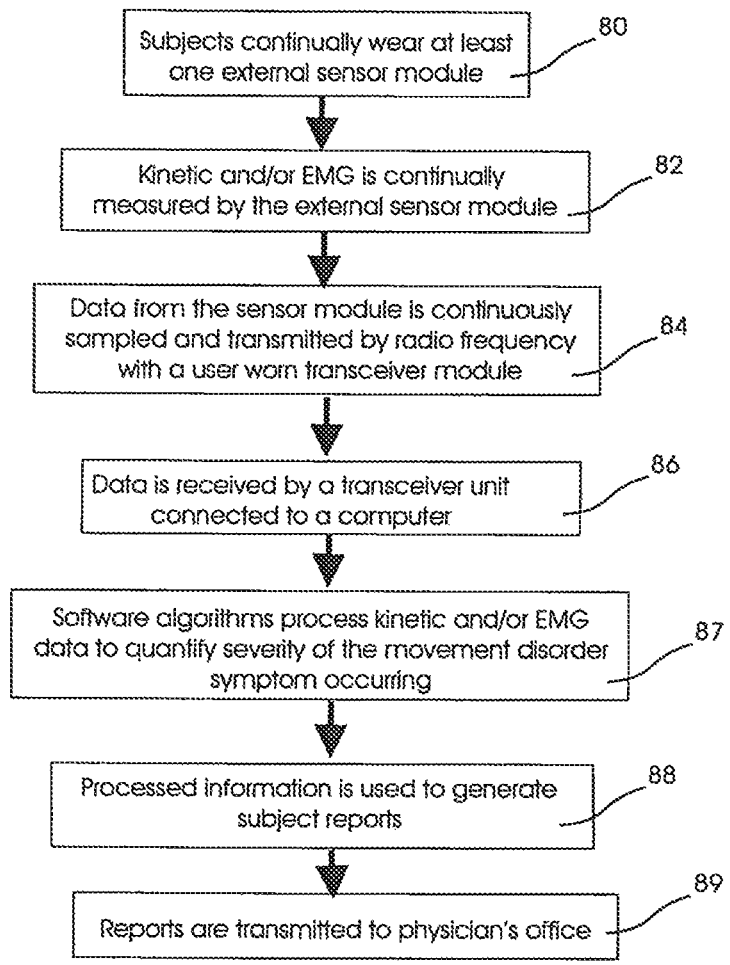
FIG. 8. Flow diagram of system in continuous operating mode.
Figure 9:
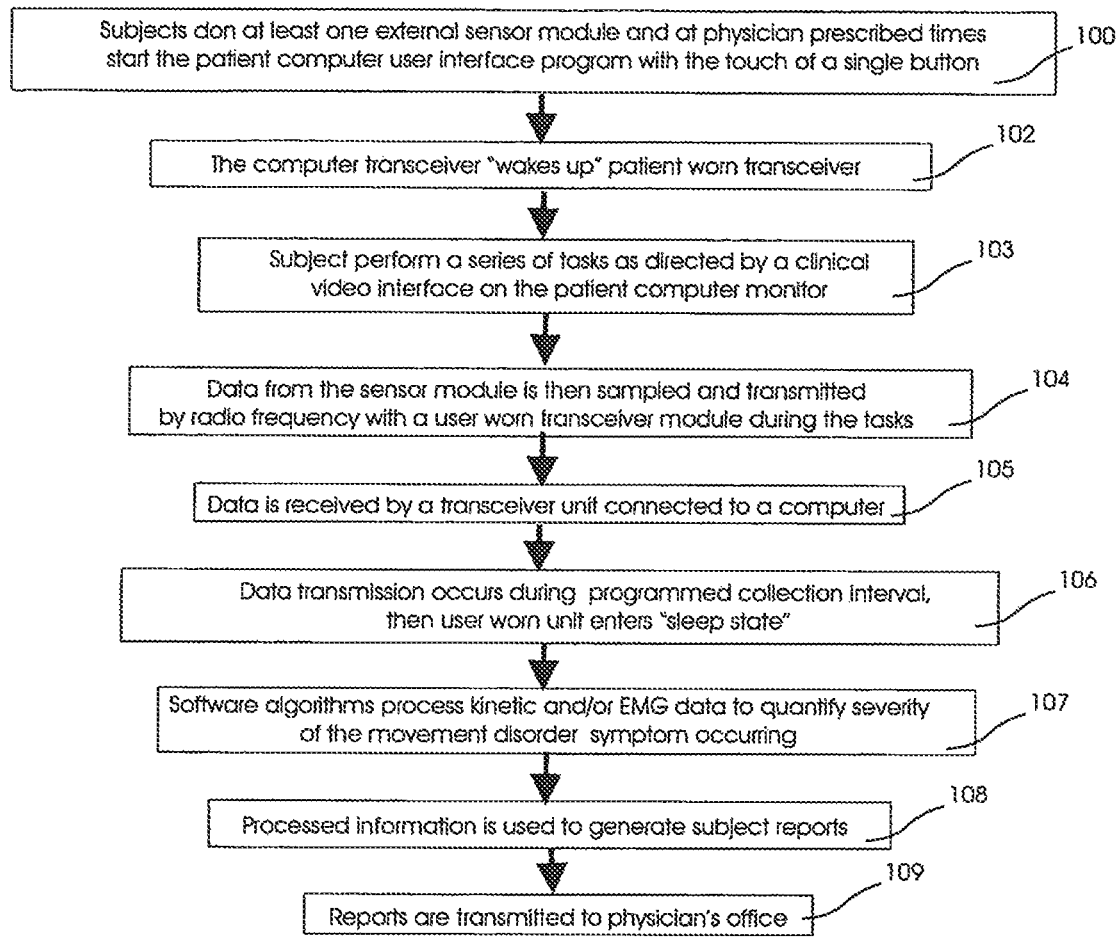
FIG. 9. Flow diagram of system in task operating mode.
Figure 10:
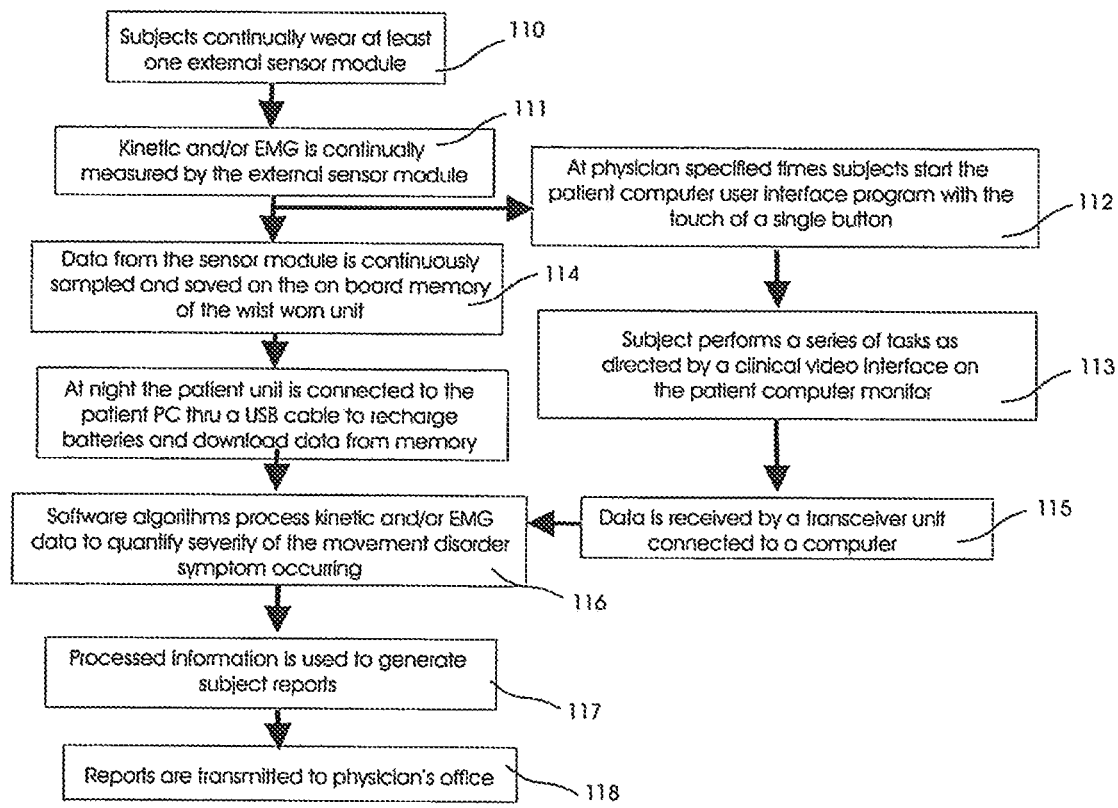
FIG. 10. Flow diagram of system in a combination operating mode.

FIGS. 8-10 show flow diagrams for various operating modes of the system of the present invention. These operating modes should be viewed as examples but not limitations to the present invention and understood that these are but a few of the methods of using the system of the present invention. FIG. 8 is a flow diagram for a continuous operating mode or method for the system of the present invention. In this embodiment, the subjects continually wear at least one external sensor module 80. The external sensor module, which can measure kinetic motion and/or EMG is continually measured by the external sensor module 82. Data from the external sensor module is continuously sampled and stored to memory within a subject worn transceiver module 84. During battery recharging of the device when the subject is not wearing the subject components, the subject components are connected through a hardwire USB link to the subject PC. The stored data is then either transmitted via an RF link to a transceiver unit connected to a computer 86 or transferred through the USB port to the computer. Software algorithms in the computer process kinetic and/or EMG data to quantify the severity of the movement disorder symptom occurring 87. The processed information is then used to generate subject reports or data 88, and the reports or data are transmitted to technician, clinician or physician for review 89.

FIG. 9 is a flow diagram for a task operating mode or method for the system of the present invention. In this mode the subjects intermittently wear at least one external sensor module at technician, clinician or physician prescribed times 100. The subjects may start the subject computer user interface program, preferably with the touch of a single button. The computer transceiver "wakes up" the subject worn transceiver module 102 or the clinical video on the subject computer instructs the subject to press a button on the transceiver module to manually "wake up" the unit. The subject performs a series of tasks as directed by a clinical video, which preferably is viewed on the subject's computer monitor 103. The data from the external sensor module is then sampled and transmitted by radio frequency with the subject worn transceiver module during the tasks 104. The data is received by a transceiver unit connected to the computer 105. The data transmission lasts approximately or only as long as the same time as a programmed collection interval, the subject worn transceiver unit then enters into a "sleep state" 106. Software algorithms in a computer connected to the computer transceiver unit process the kinetic motion and/or EMG data to quantify severity of the movement disorder symptom occurring 107. The processed information is then used to generate subject reports or data 108, and the reports or data are transmitted to technician, clinician or physician for review 109.

FIG. 10 is a flow diagram for a combination operating mode or method for the system of the present invention. In this mode, the subject continually wears at least one external sensor module 110. The external sensor module, which can measure kinetic motion and/or EMG is continually measured by the external sensor module 111. Data from the external sensor module is continuously sampled and stored to memory on the subject worn transceiver module 114. This data is then downloaded to the subject computer at a later time. Software algorithms in the computer process kinetic and/or EMG data to quantify the severity of the movement disorder symptom occurring 116. The processed information is then used to generate subject reports or data 117, and the reports or data are transmitted to technician, clinician or physician for review 118. This method, however, varies from the method described in FIG. 8 in that at technician, clinician, physician or computer at randomly specified times alerts the subject start or has computer starts a video 112, and alerts the subject to perform a series of tasks as directed by the clinical video, which is preferably on the subject's computer monitor 113. During these tasks, data is transmitted by the user worn receiver module and is received by a transceiver unit connected to a computer 115. Software algorithms in the computer process kinetic and/or EMG data to quantify the severity of the movement disorder symptom occurring 116. The processed information is then used to generate subject reports or data 117, and the reports or data are transmitted to technician, clinician or physician for review 118.

The portable movement disorder device of the present invention for measuring the severity of a subject's movement disorder can be worn in any way likely to provide good data on a subject's movement disorder. Examples would include but are not limited to the use of the device on the subject's hand and/or arm; legs, and/or head. Preferably, the movement disorder device is on the arm and/or hand of the subject. FIGS. 6 and 7 and show a schematic of a movement disorder device on a subject's lower arm and hand. In this embodiment, the subject's kinetic motion is measured by a kinetic sensor board (also known as external sensor module) 50. The external sensor module 50 is held firmly to the subject's finger 51 by a hood and loop strap 52. The external sensor module 50 is connected to a subject worn transceiver module 64 via electrical pathways or wires 54. Optionally, the device may also have at least one EMG electrodes (not shown).

Preferably, the subject worn transceiver module in this embodiment is reasonably small size. Achieving the wrist mount design of this embodiment require the size of the radio used for the device be greatly reduced. Preferably, a commercially available chip (blue tooth technology) is used that can transmit up to 200 ft. Not only will this greatly reduce the size of the device, but the transceiver capability will allow two-way communications between the subject worn unit and the computer unit.

The two-way capability in this particular embodiment will provide multiple benefits. First, by having two-way communications, the unit will be capable of utilizing a protocol where data packets can be resent if corrupted during transmission. Another benefit is that several subject worn units could potentially communicate with a single base station clinician PC. In this scenario, the subject units occupy dedicated time slots to transmit their information. Several subject worn units could operate with a single computer base station in a hospital or home setting. Additionally, multiple units may be worn on a subject to monitor tremor in both hands at the same time. A final benefit of the two-way protocol is that configuration information can be sent to the subject unit over the radio link including power level, frequency, and shut down modes. Shut down modes could be of great benefit for this type of system where the clinical PC can command the subject units to power down between tests thus conserving battery life in the subject unit. Essentially, the technician, clinician, or physician will be able to program the system for continuous recording or to record at certain times for specified intervals.

Preferably, the radio design of this specific embodiment is implemented using a highly integrated radio chip (Bluetooth® technology) which requires very few external components, consumes less power than a discrete radio design, and requires less physical area than a discrete design. More preferably, the radio chip takes incoming clock and data and produces a Frequency Modulated carrier when configured as a transmitter, and performs the opposite function when configured as a receiver. This high level of integration makes the only component required to interface to the radio section a unit microcontroller.

With few components and high level of integration, the radio section should be easy to manufacture, have low component cost, and have high field reliability. Preferably, the IC or microprocessor has a controllable RF power output levels and by using the two-way protocol described above, the radio link can operate at a level high enough to ensure reliable data transfer while conserving unit power. Finally, the most preferably, the IC or microprocessor can operate anywhere from 300 MHz to 2.4 GHz providing great flexibility when the system is developed to ensure optimum operation. The 2.4 GHz band is the preferable operating band.

Figure 11:
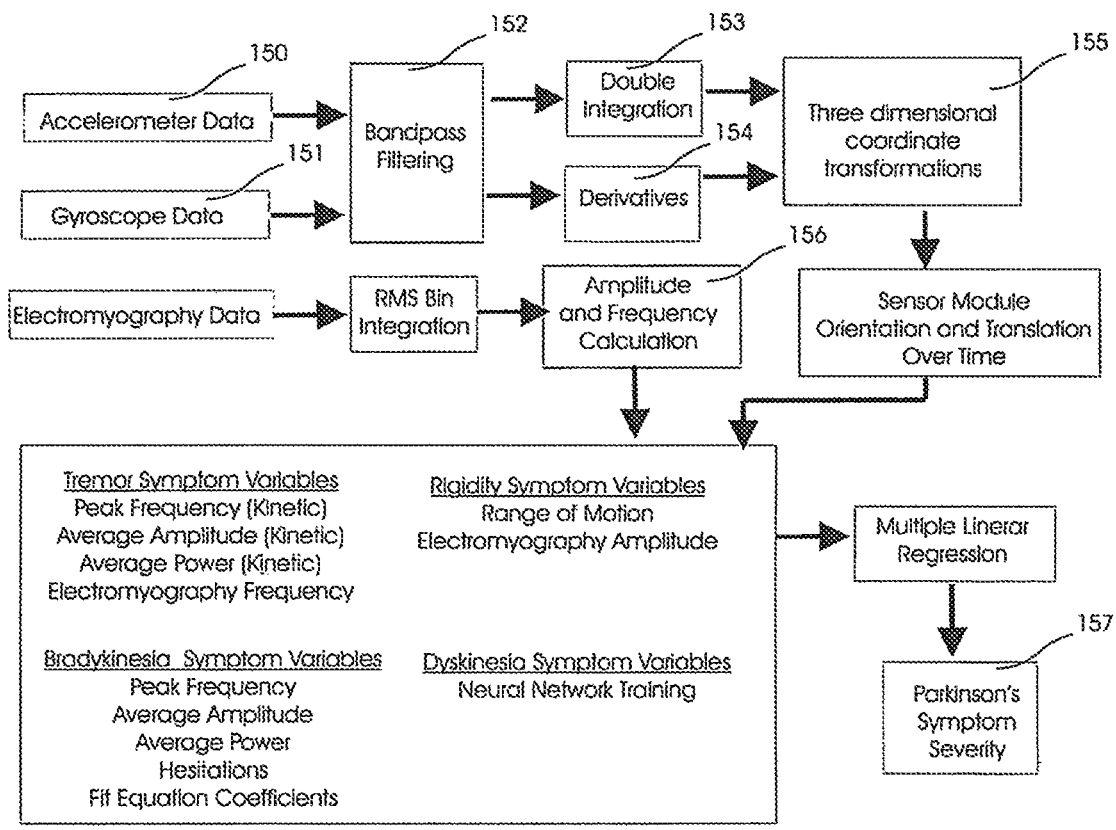
FIG. 11. Flow diagram for one embodiment of the software used in the present invention.

FIG. 11 is a flow diagram for one embodiment of the software used in the present invention. Analog outputs 151, 152 from the accelerometer and gyroscope are converted to linear acceleration and angular velocity with a scaling factor. The linear accelerations and angular velocity inputs are then bandpass filtered 153 to prevent biasing and remove DC drift. The linear acceleration is double integrated to yield linear position. The derivative 154 of the angular velocity is calculated to determine angle. The three dimensional translation and rotation 155 of the module is computed from the information from the three orthogonal accelerometers and three orthogonal gyroscopes. The root mean square (RMS) value of the continuous time EMG signal is calculated over discrete time windows. The amplitude and frequency 156 of the processed EMG signal is calculated. Specific variables are then computed for each Parkinson's symptom based on the processed kinetic and EMG data. Tremor symptom variables may include but are not limited to the peak frequency of the kinetic sensors, the average amplitude of the kinetic sensors, the average power of the kinetic sensors, and the frequency of the EMG signals. Bradykinesia symptom variables may include but are not limited to the peak frequency of EMG or kinetic data, the average amplitude of the kinetic sensors, the average power of the EMG or kinetic sensors, the number of hesitations that occur in a subjects movement, or the linear or exponential fit coefficients used to fit a model to the amplitude of a subject's movement over time. Rigidity symptom variables may include but are not limited to range of motion and EMG amplitude. Dyskinesia symptom variables may include but are not limited to the output of a neural network trained to recognize dyskinesia from other movements using the kinetic sensor data as inputs. The value of each symptom variable for a particular symptom is used in an algorithm that may include but are not limited to multiple linear regression models or neural networks to fit the symptom variables to the qualitative clinicians Unified Parkinson's Disease Rating Scale scores for that symptom 157.

The present invention further includes a drug delivery system. The drug delivery system utilizes in part the input from the external sensors or the scoring of the severity of the subject's movement disorder or the movement disorder symptoms as input into a closed loop control system to deliver medication to lessen or relieve the symptoms of the disorder, or to appropriately treat the disorder in a non-symptomatic way. The drug delivery system comprises the at least one external sensor having a signal for measuring a subject's external body motion or a physiological signal associated with a movement disorder. The drug delivery system comprises at least one external sensor being described earlier in the application. The drug delivery system further comprises a reservoir for some form of medication, preferably liquid, that can either be delivered to the subject internally or transcutaneously. The system further comprises an actuator which when activated and deactivated allows the medication to be delivered from the reservoir to the subject. Finally, the system further comprises a closed-loop control system which activates and deactivates the actuator based in part on a signal from the at least one external sensor.

Figure 12:
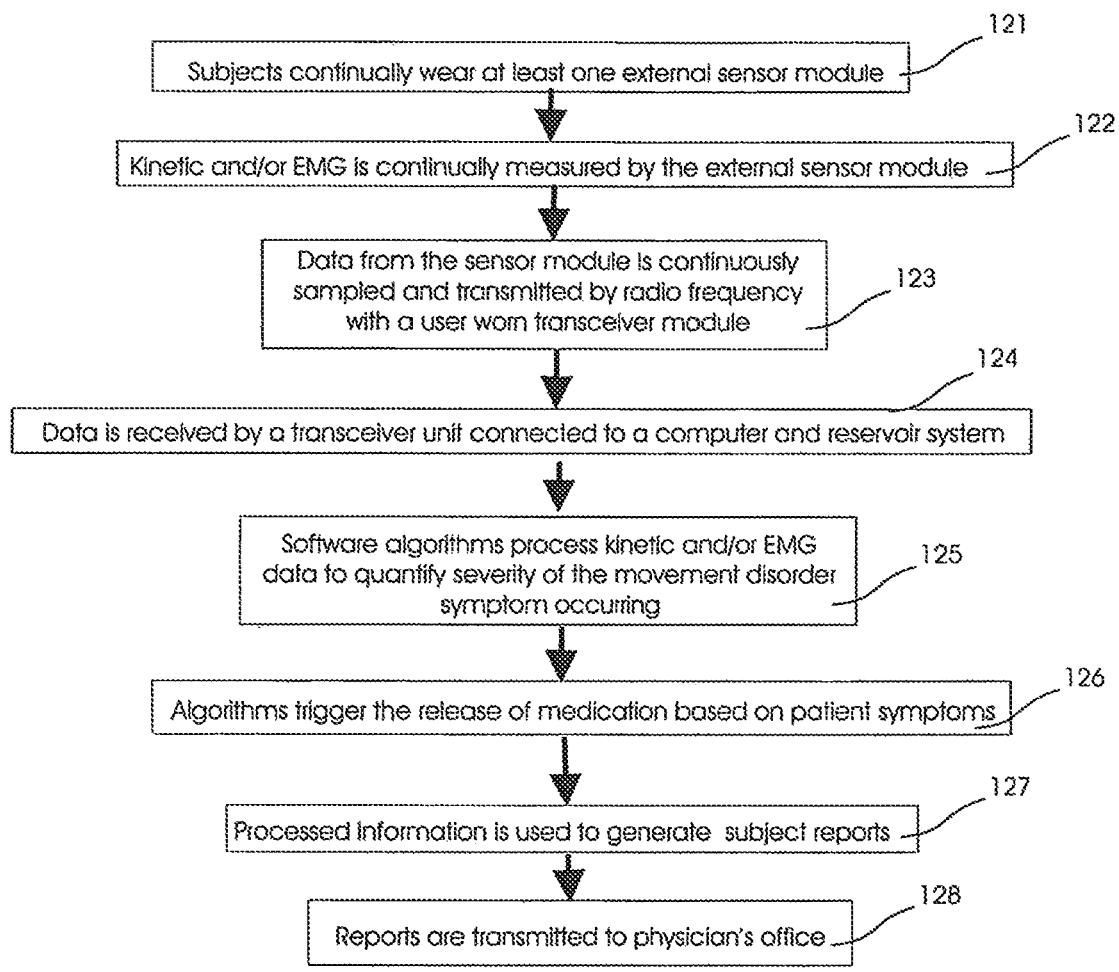
FIG. 12. Flow diagram for one embodiment of a closed-loop drug delivery system of the present invention.

FIG. 12 is a flow diagram for one embodiment of a closed-loop drug delivery system of the present invention. In this embodiment, the subjects continually wear at least one external sensor module 121. Kinetic motion and/or EMG is continually measured by the external sensor module 122. Data from the external sensor module is continuously sampled and transmitted by radio frequency with a subject worn transceiver module 123. The transmitted data is received by a transceiver unit connected to a reservoir system 124 with embedded processing. Software algorithms process kinetic and/or EMG data to quantify the severity of the movement disorder symptom occurring 124. The software algorithms trigger the release of medication based on the subject's symptoms 126, or the overall severity of the movement disorder 125. The processed information is then used to generate subject reports or data 127, and the reports or data are transmitted to technician, clinician or physician for review 128.

Figure 13:
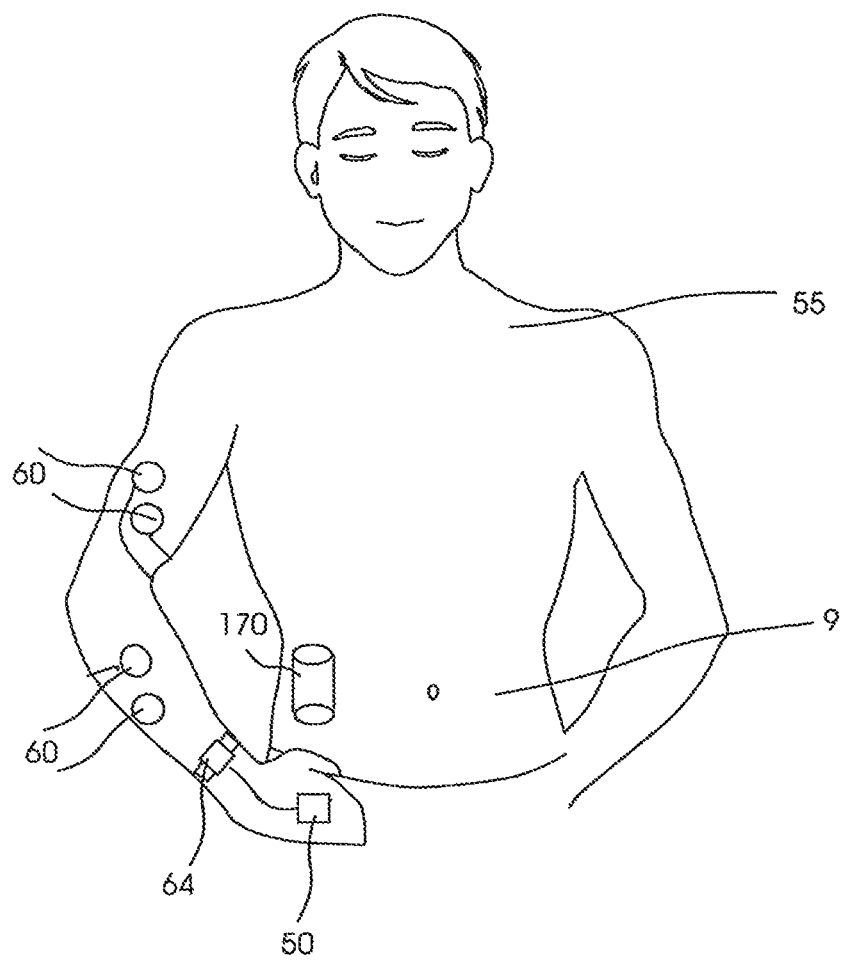
FIG. 13. Schematic showing placement of various components of closed loop drug delivery system with an implantable reservoir.

FIG. 13 is a schematic diagram showing placement of various components of closed loop drug delivery system with an implantable reservoir. In FIG. 13, the subject 55 is wearing a closed loop drug delivery system. The closed loop drug may have an external sensor module 50, a subject worn transceiver module 64, EMG electrodes 60, a reservoir 170 for holding medication with an embedded transceiver and processor and actuator for allowing delivery (not shown), and a controller for activating and deactivating the actuator based in part on the signal from the at least one of the sensor modules 50. In this example a reservoir 170 being implanted into the abdomen 9 of the subject. The reservoir 170 containing medication, which is released into the subject's body through activation of an actuator. The respective transceiver module 64 being connected to the EMG electrodes 60 and external sensor modules 50 via electrical pathways or wires (not shown). The transceiver module 64 being further being connected either wirelessly or via electrical pathways or wires (not shown) to a controller (not shown), which activates and deactivates an actuator (not shown) to release medication from the implantable reservoir 170.

Figure 14:
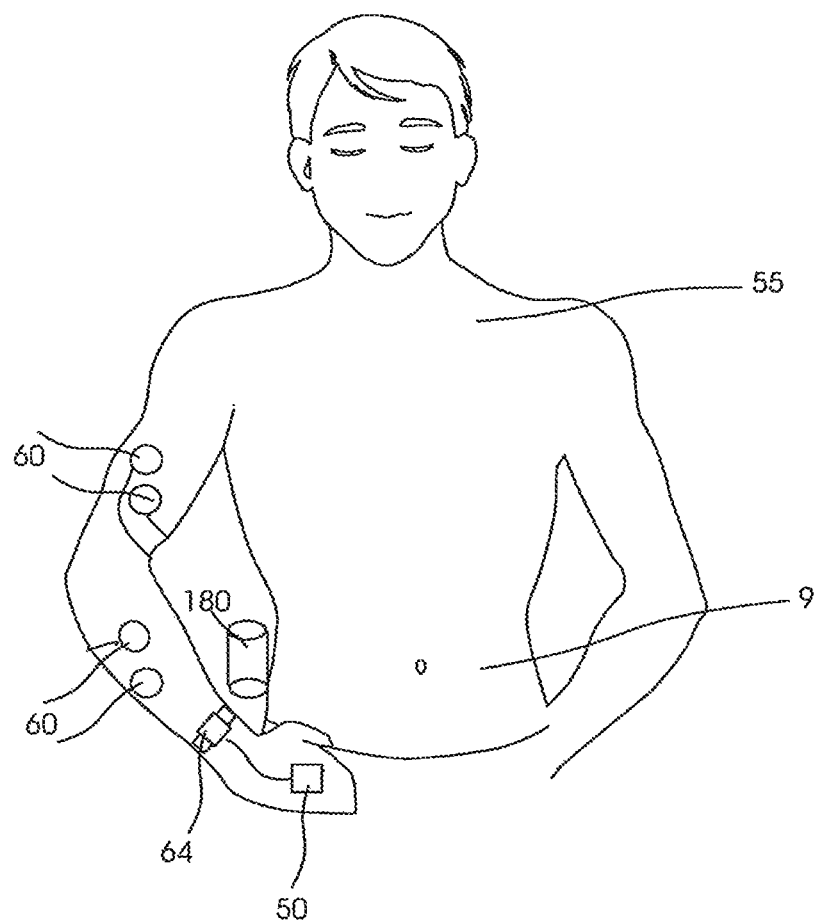
FIG. 14. Schematic showing placement of various components of closed loop drug delivery system with an external reservoir to transcutaneous delivery.

FIG. 14 is a schematic diagram showing placement of various components of a closed loop drug delivery system with an external reservoir to transcutaneous delivery. In FIG. 14, the subject 55 is wearing a closed loop drug delivery system. The closed loop drug delivery system may have an external sensor module 50, a subject worn transceiver module 64, EMG electrodes 60, a reservoir 180 for holding medication with an embedded transceiver and processor and actuator for allowing delivery (not shown), and a controller for activating and deactivating the actuator based in part on the signal from the at least one of the sensor modules 50. In this example a reservoir 180 is attached externally to the abdomen 9 of the subject. The reservoir 180 containing medication, which is released into the subject's body through activation of an actuator. The respective transceiver module 64 being connected to the EMG electrodes 60 and external sensor module 50 via electrical pathways or wires (not shown). The transceiver module 64 being further being connected either wirelessly or via electrical pathways or wires (not shown) to a controller (not shown), which activates and deactivates an actuator (not shown) to release medication from the implantable reservoir 180.

Figure 15:
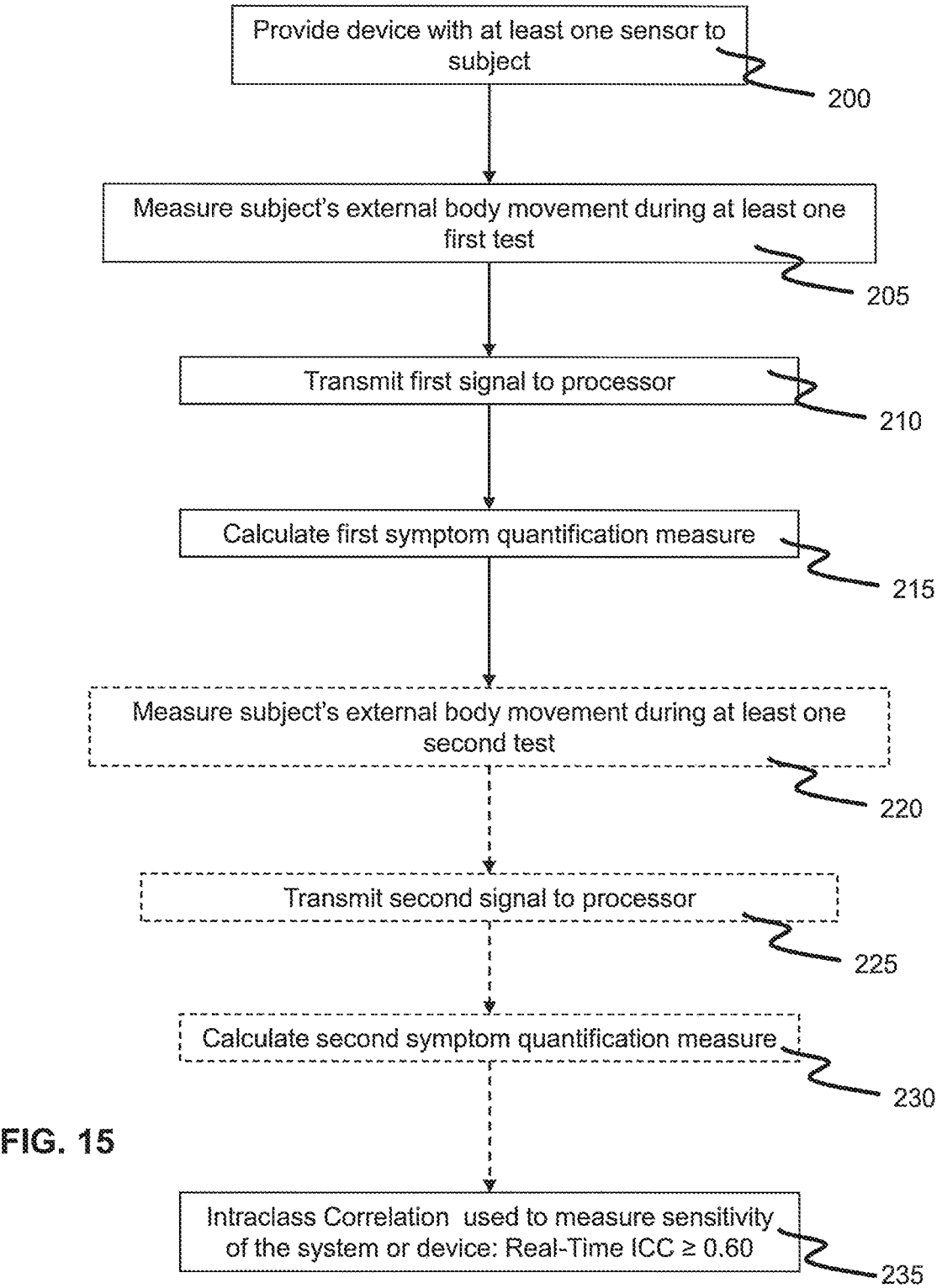
FIG. 15. Flow diagram of a sensitive method for quantifying movement disorder symptom severity comprising a set of at least one test that is repeated, where sensitivity is measured by intraclass correlation (ICC) of repeated tests.

FIG. 15 is a flow chart depicting the methods of several embodiments of the present invention for quantifying a subject's movement disorder symptoms where sensitivity is measured using intraclass correlation (ICC). First, a device comprising at least one sensor having a signal corresponding to a subject's external body motion associated with a movement disorder is provided 200 to the subject. The at least one sensor may be of any variety described herein, including, but not limited to accelerometers, gyroscopes, pressure sensors, force sensors, and the like. The step of providing 200 the device to the subject may further comprise steps of giving instructions for the subject to properly don or apply the device. Once the device has been provided 200 to the subject, the next step is to measure the subject's external body motion 205 while the subject performs at least one first movement disorder test, activity, movement or motion. The test, activity, movement or motion preferably corresponds to at least one symptom of a movement disorder in such a way that the test, activity, movement or motion is likely to exhibit at least one symptom of a movement disorder. When the subject performs the test, activity, movement or motion the at least one sensor of the device measures the external body motion of the subject, including any movement disorder symptom motions that are present. Either after the test is complete, or during testing, a signal from the at least one sensor is transmitted to a processor 210. The processor then calculates a symptom quantification measure or score 215 from the first at least one test performed. This first symptom quantification measure or score is based at least in part on the signal received from the at least one sensor of the device corresponding to the subject's external body motion during the first test, activity, movement or motion, and is preferably stored for later comparison, analysis, evaluation, recollection, or other uses. The symptom quantification measure or score is preferably calculated 215 substantially in real time corresponding to the performance and/or completion of the first movement disorder test.

Subsequently, a second movement disorder test is performed. Similar to during the first test, the device measures the subject's external body motion while the subject is performing the second test 220. This second test may be performed either immediately following the first test, or, more preferably, at a later time (e.g., up to 30 days later), but is performed under substantially similar circumstances as the first test. Similarly, the second test is preferably the same test, activity, movement or motion (or set thereof) as the first movement disorder test. Again, the second signal from the at least one sensor is transmitted to a processor 225 for comparison, analysis, evaluation, recollection, or the like. The processor similarly uses this second signal to calculate a second symptom quantification measure or score 230. This process may be repeated any number of times, each time conducting the same movement disorder test(s) comprising the same tests, activities, movements or motions under substantially similar circumstances. The separate symptom quantification measures or scores can then be compared in order to calculate various sensitivity metrics corresponding to the repeatability, accuracy, consistency and the like of the device, method and/or system. In many embodiments, the separate symptom quantification measures or scores are used to measure sensitivity by calculating the intraclass correlation (ICC) 235 of the symptom quantification measures, and preferably the ICC is at least about 0.60.

Figure 16:
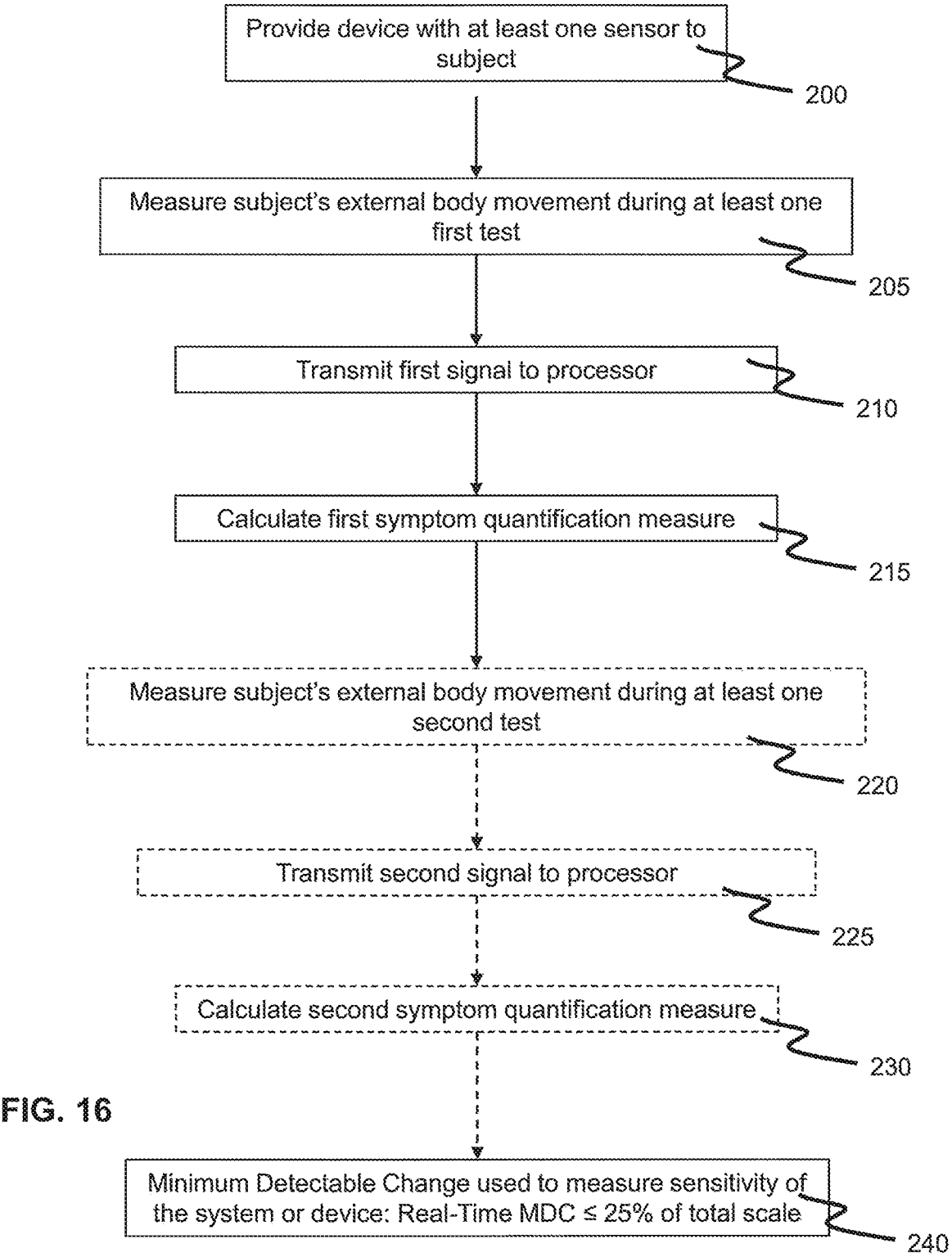
FIG. 16. Flow diagram of a sensitive method for quantifying movement disorder symptom severity comprising a set of at least one test that is repeated, where sensitivity is measured by minimal detectable change (MDC).

FIG. 16 is a flow chart depicting the methods of several embodiments of the present invention for quantifying a subject's movement disorder symptoms where sensitivity is measured using minimum detectable change (MDC). First, a device comprising at least one sensor having a signal corresponding to a subject's external body motion associated with a movement disorder is provided 200 to the subject. The at least one sensor may be of any variety described herein, including, but not limited to accelerometers, gyroscopes, pressure sensors, force sensors, and the like. The step of providing 200 the device to the subject may further comprise steps of giving instructions for the subject to properly don or apply the device. Once the device has been provided 200 to the subject, the next step is to measure the subject's external body motion 205 while the subject performs at least one first movement disorder test, activity, movement or motion. The test, activity, movement or motion preferably corresponds to at least one symptom of a movement disorder in such a way that the test, activity, movement or motion is likely to exhibit at least one symptom of a movement disorder. When the subject performs the test, activity, movement or motion the at least one sensor of the device measures the external body motion of the subject, including any movement disorder symptom motions that are present. Either after the test is complete, or during testing, a signal from the at least one sensor is transmitted to a processor 210. The processor then calculates a symptom quantification measure or score 215 from the first test performed. This first symptom quantification measure or score is based at least in part on the signal received from the at least one sensor of the device corresponding to the subject's external body motion during the first test, activity, movement or motion, and is preferably stored for later comparison, analysis, evaluation, recollection, or other uses. The symptom quantification measure or score is preferably calculated 215 substantially in real time corresponding to the performance and/or completion of the first movement disorder test.

Subsequently, a second movement disorder test is performed. Similar to the first test, the device measures the subject's external body motion while the subject is performing the second test 220. This second test may be performed either immediately following the first test, or, more preferably, at a later time (e.g., up to 30 days later), but is performed under substantially similar circumstances as the first test, and with the subject in a substantially similar disease state (e.g., a second or subsequent test would not be conducted if the subject had broken his or her leg since the first test because the circumstances and disease state would not be substantially similar). Similarly, the at least one second test is preferably the same test, activity, movement or motion (or set thereof) as the first movement disorder test. Again, the second signal from the at least one sensor is transmitted to a processor 225 for comparison, analysis, evaluation, recollection, or the like. The processor similarly uses this second signal to calculate a second symptom quantification measure or score 230. This process may be repeated any number of times, each time conducting the same movement disorder tests comprising the same tests, activities, movements or motions under substantially similar circumstances. The separate symptom quantification measures or scores can then be compared in order to calculate various sensitivity metrics corresponding to the repeatability, accuracy, consistency and the like of the device, method and/or system. In many embodiments, the separate symptom quantification measures or scores are used to measure sensitivity by calculating the minimum detectable change (MDC) 240 of the symptom quantification measures, and preferably the MDC represents at a change of about 25% or less of the total scale of the particular test(s). As noted herein, the scale and measurement units of each individual test will vary (e.g., a gait test or test for standing up from a seated position may be measured in time with a total maximum allowable time to set the scale, whereas other tests may be measured in unitless scores or different units such as frequency, each with a different scale for maximum allowable measurements).

Various embodiments of the present invention may include a step whereby the subject fills out a diary or log. Preferably, the diary or log specifically relates to the subject's disease state at the time it is filled out. Entries into the diary or log may be performed on a periodic basis determined by a clinician or study administrator. When the subject makes an entry into the diary or log, such entry may be a personal account of the subject's condition and disease state, though more preferably is a simplified input system whereby the subject merely the presence of one disease state, such as by checking a box or clicking a button. Exemplary disease states typically used in movement disorder studies include "ON," "OFF," "ON with dyskinesias," and "On with non-troublesome dyskinesias," or variants thereof. The disease state "ON" relates to time when the subject has taken medication, and that medication is providing a perceived benefit in improving the subject's mobility, such as by reducing stiffness and/or improving speed of movement. The disease state "OFF" relates to time when medication has worn off and is no longer providing a benefit to the subject with regard to mobility and movement. The disease state "ON with dyskinesias" relates to time when the subject has taken medication that is still in effect (i.e., has not worn off), but is still experiencing dyskinesias that interrupt the subject's mobility, function or movement, such as involuntary twisting or turning movements. Typically, in this disease state, the dyskinesias are perceived to be a side effect of the medication. The disease state of "ON with non-troublesome dyskinesias" relates to time when the subject has taken medication that is still in effect (i.e., has not worn off), but is still experiencing dyskinesias; however, the dyskinesias are not causing any meaningful discomfort to the subject and do not interfere with mobility, function or movement. An example of a condition that would qualify as "ON with non-troublesome dyskinesias" is a mild tremor. In other, more preferred embodiments, the device and system are able to automatically detect the presence of one of these disease states without requiring the subject to manually fill out a diary or log. These embodiments with automated disease state detection preferably include the disease state with other data that is recorded and stored and/or transmitted.

Figure 17:
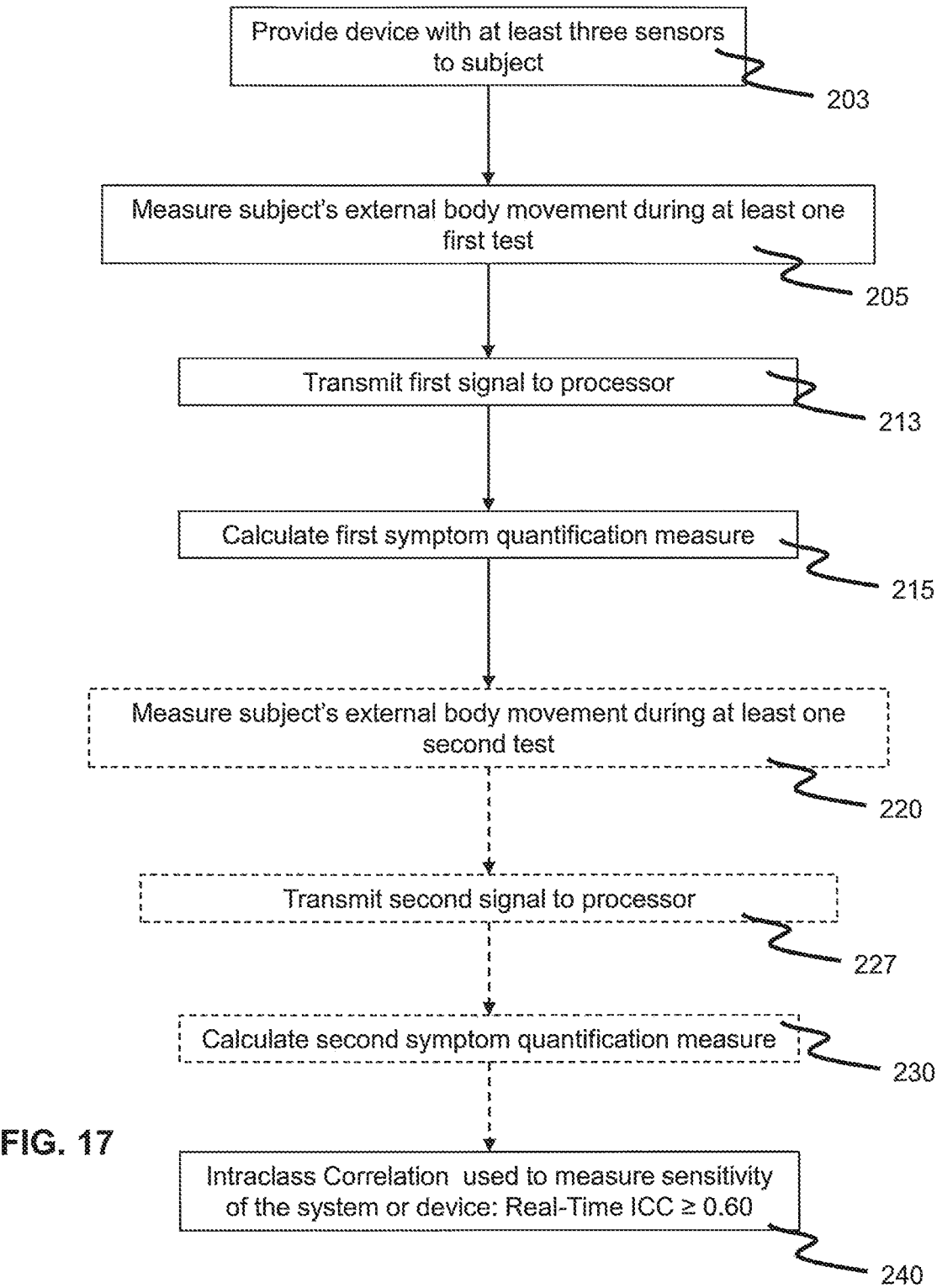
FIG. 17. Flow diagram of another embodiment of a sensitive method for to quantifying movement disorder symptom severity with a device comprising at least three sensors, the method comprising a set of at least one test that is repeated, and where sensitivity is measured by intraclass correlation (ICC) of repeated tests.

FIG. 17 is a flow chart depicting the methods of several embodiments of the present invention for quantifying a subject's movement disorder symptoms where sensitivity is measured using intraclass correlation (ICC). First, a device comprising at least three sensors, each having a signal corresponding to a subject's external body motion associated with a movement disorder, is provided 203 to the subject. These at least three sensors may be of any variety described herein, including, but not limited to accelerometers, gyroscopes, pressure sensors, force sensors, and the like. Preferably, at least one sensor is an accelerometer, and at least one sensor is a gyroscope. The step of providing 203 the device comprising at least three sensors to the subject may further comprise steps of giving instructions for the subject to properly don or apply the device. Once the device has been provided 203 to the subject, the next step is to measure the subject's external body motion 205 while the subject performs at least one first movement disorder test, activity, movement or motion. The test, activity, movement or motion preferably corresponds to at least one symptom of a movement disorder in such a way that the test, activity, movement or motion is likely to exhibit at least one symptom of a movement disorder. When the subject performs the test, activity, movement or motion the at least three sensors of the device measure the external body motion of the subject, including any movement disorder symptom motions that are present. Either after the test is complete, or during testing, a first signal is transmitted to a processor 213. The first signal may actually comprise at least three separate signals, one corresponding to each of the at least three sensors of the device. Alternatively, this first transmitted signal may be a composite signal representing a combination of signals from the at least three sensors of the device. In either format, the transmission from the device to the processor, whether a single composite signal or several individual sensor signals, constitutes a single signal representing the measured external body motions during the at least one first movement disorder test. The processor then calculates a symptom quantification measure or score 215 from the at least one first test performed. This first symptom quantification measure or score is based at least in part on the signal(s) received from the at least three sensors of the device corresponding to the subject's external body motion during the first test, activity, movement or motion, and is preferably stored for later comparison, analysis, evaluation, recollection, or other uses. The symptom quantification measure or score is preferably calculated 215 substantially in real time corresponding to the performance and/or completion of the first movement disorder test.

Subsequently, a second movement disorder test is performed. Similar to the first test, the device measures the subject's external body motion while the subject is performing the second test 220. This second test may be performed either immediately following the first test, or, more preferably, at a later time (e.g., up to 30 days later), but is performed under substantially similar circumstances as the first test. Similarly, the second test is preferably the same test, activity, movement or motion (or set thereof) as the first movement disorder test. Again, the second signal from the at least three sensors are transmitted to a processor 227 for comparison, analysis, evaluation, recollection, or the like. Much like the first transmission, the second signal may comprise a single composite signal or individual sensor signals. The processor similarly uses this second signal to calculate a second symptom quantification measure or score 230. This process may be repeated any number of times, each time conducting the same movement disorder tests comprising the same tests, activities, movements or motions under substantially similar circumstances. The separate symptom quantification measures or scores can then be compared in order to calculate various sensitivity metrics corresponding to the repeatability, accuracy, consistency and the like of the device, method and/or system. In many embodiments, the separate symptom quantification measures or scores are used to measure sensitivity by calculating the intraclass correlation (ICC) 235 of the symptom quantification measures, and preferably the ICC is at least about 0.60.

Figure 18:
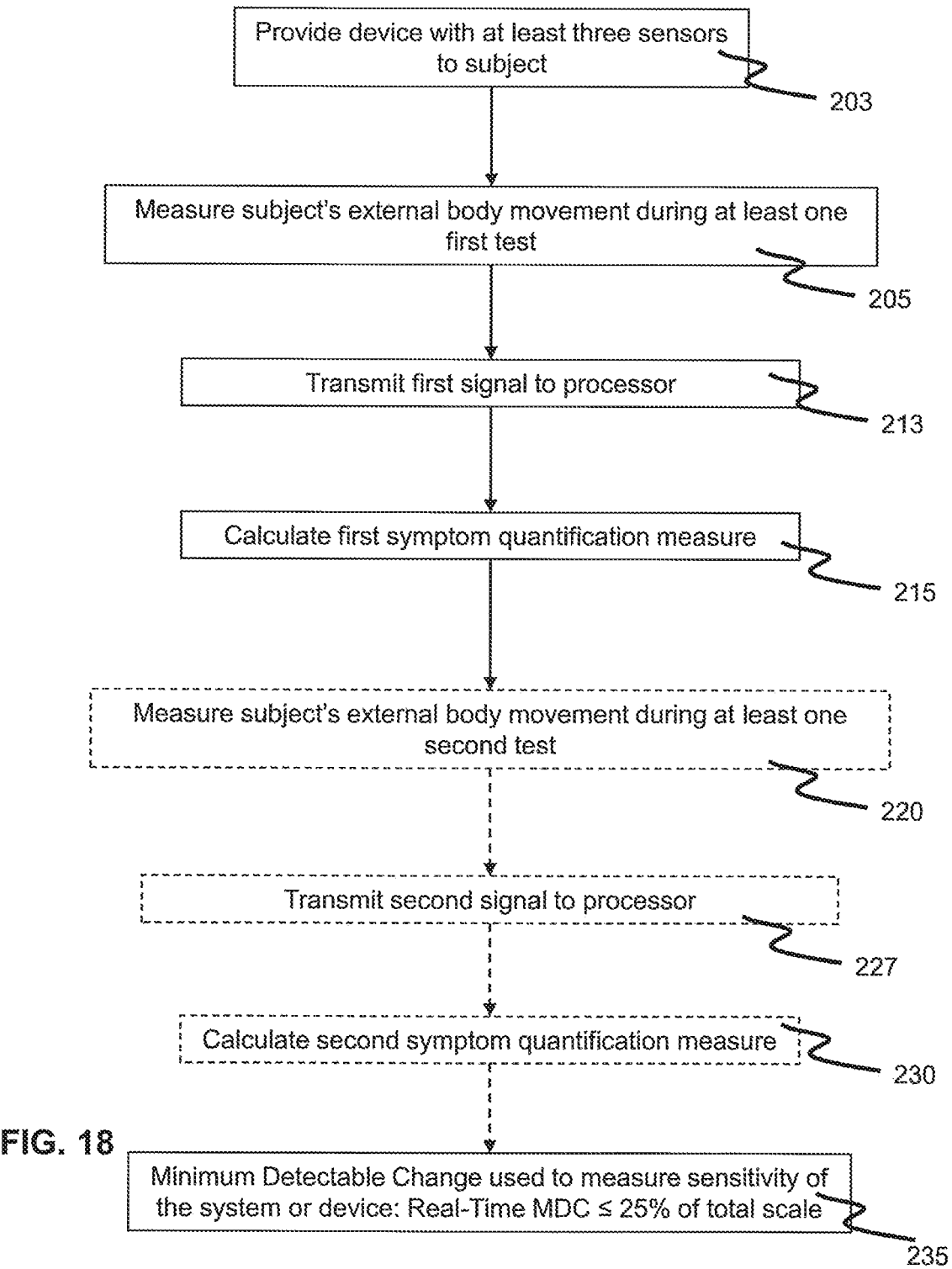
FIG. 18. Flow diagram of another embodiment of a sensitive method for quantifying movement disorder symptom severity with a device comprising at least three sensors, the method comprising a set of at least one test that is repeated, and where sensitivity is measured by minimum detectable change (MDC) of repeated tests.

FIG. 18 is a flow chart depicting the methods of several embodiments of the present invention for quantifying a subject's movement disorder symptoms where sensitivity is measured using minimum detectable change (MDC). First, a device comprising at least three sensors, each having a signal corresponding to a subject's external body motion associated with a movement disorder, is provided 203 to the subject. These at least three sensors may be of any variety described herein, including, but not limited to accelerometers, gyroscopes, pressure sensors, force sensors, and the like. Preferably, at least one sensor is an accelerometer, and at least one sensor is a gyroscope. The step of providing 203 the device comprising at least three sensors to the subject may further comprise steps of giving instructions for the subject to properly don or apply the device. Once the device has been provided 203 to the subject, the next step is to measure the subject's external body motion 205 while the subject performs at least one first movement disorder test, activity, movement or motion. The test, activity, movement or motion preferably corresponds to at least one symptom of a movement disorder in such a way that the test, activity, movement or motion is likely to exhibit at least one symptom of a movement disorder. When the subject performs the test, activity, movement or motion the at least three sensors of the device measure the external body motion of the subject, including any movement disorder symptom motions that are present. Either after the test is complete, or during testing, a first signal is transmitted to a processor 213. The first signal may actually comprise at least three separate signals, one corresponding to each of the at least three sensors of the device. Alternatively, this first transmitted signal may be a composite signal representing a combination of signals from the at least three sensors of the device. In either format, the transmission from the device to the processor, whether a single composite signal or several individual sensor signals, constitutes a single signal representing the measured external body motions during the at least one first movement disorder test. The processor then calculates a symptom quantification measure or score 215 from the at least one first test performed. This first symptom quantification measure or score is based at least in part on the signal(s) received from the at least three sensors of the device corresponding to the subject's external body motion during the first test, activity, movement or motion, and is preferably stored for later comparison, analysis, evaluation, recollection, or other uses. The symptom quantification measure or score is preferably calculated 215 substantially in real time corresponding to the performance and/or completion of the first movement disorder test.

Subsequently, a second movement disorder test is performed. Similar to the first test, the device measures the subject's external body motion while the subject is performing the second test 220. This second test may be performed either immediately following the first test, or, more preferably, at a later time (e.g., up to 30 days later), but is performed under substantially similar circumstances as the first test. Similarly, the second test is preferably the same test, activity, movement or motion (or set thereof) as the first movement disorder test. Again, the second signal from the at least three sensors are transmitted to a processor 227 for comparison, analysis, evaluation, recollection, or the like. Much like the first transmission, the second signal may comprise a single composite signal or individual sensor signals. The processor similarly uses this second signal to calculate a second symptom quantification measure or score 230. This process may be repeated any number of times, each time conducting the same movement disorder tests comprising the same tests, activities, movements or motions under substantially similar circumstances. The separate symptom quantification measures or scores can then be compared in order to calculate various sensitivity metrics corresponding to the repeatability, accuracy, consistency and the like of the device, method and/or system. In many embodiments, the separate symptom quantification measures or scores are used to measure sensitivity by calculating the minimum detectable change (MDC) 240 of the symptom quantification measures, and preferably the MDC represents at a change of about 25% or less of the total scale of the particular test(s). As noted herein, the scale and measurement units of each individual test will vary (e.g., a gait test or test for standing up from a seated position may be measured in time with a total maximum allowable time to set the scale, whereas other tests may be measured in unitless scores or different units such as frequency, each with a different scale for maximum allowable measurements).

Figure 19:
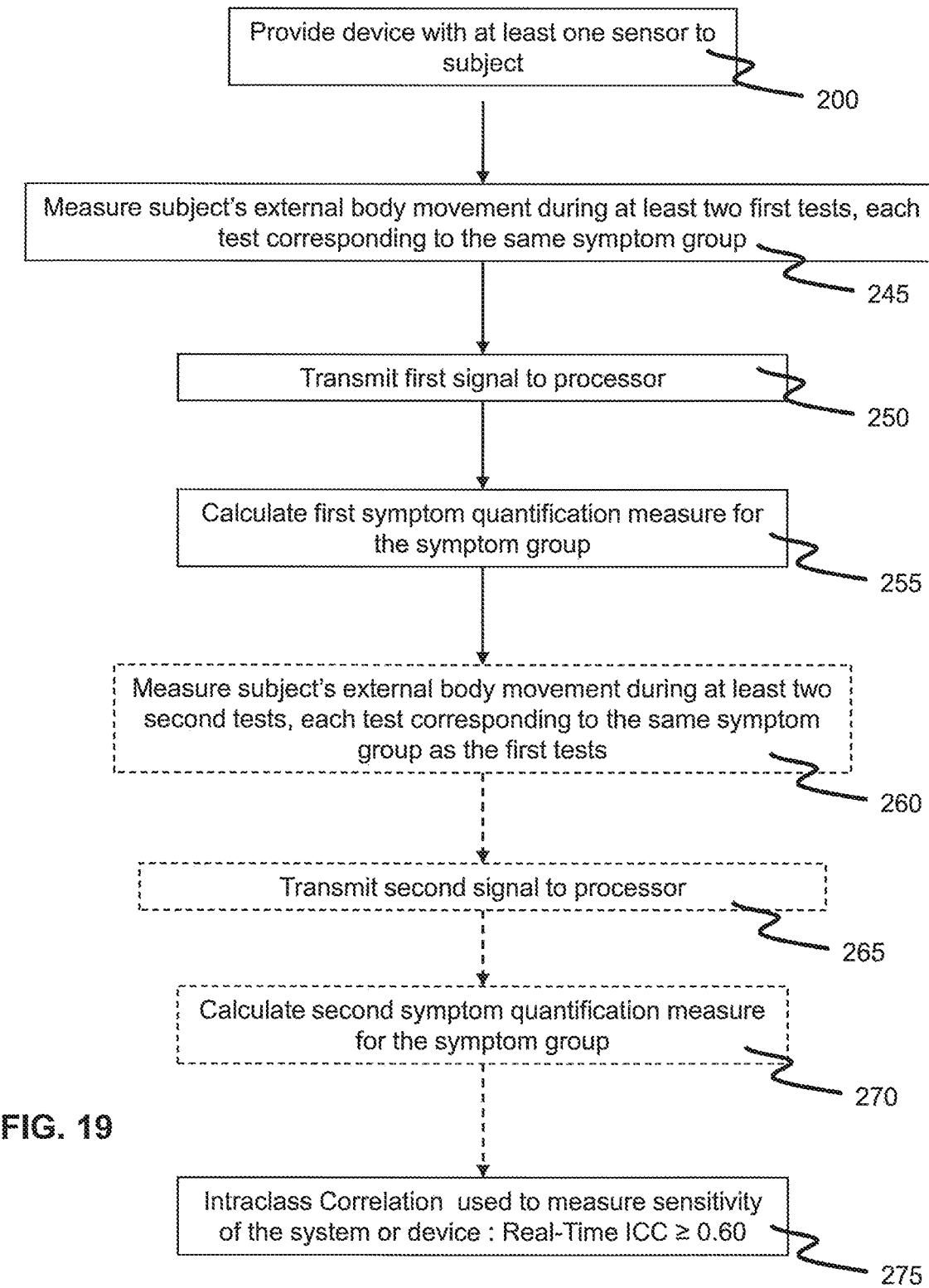
FIG. 19 Flow diagram of a sensitive method for quantifying movement disorder symptom severity comprising a set of at least two tests, both tests corresponding to the same grouping or classification of symptoms, wherein the set of at least two tests is repeated, and where sensitivity is measured by intraclass correlation (ICC) of repeated tests.

FIG. 19 is a flow chart depicting the methods of several embodiments of the present invention for quantifying a subject's movement disorder symptoms where sensitivity is measured using intraclass correlation (ICC). First, a device comprising at least one sensor, the at least one sensor having a signal corresponding to a subject's external body motion associated with a movement disorder, is provided 200 to the subject. The at least one sensor may be of any variety described herein, including, but not limited to accelerometers, gyroscopes, pressure sensors, force sensors, and the like. The step of providing 200 the device comprising at least three sensors to the subject may further comprise steps of giving instructions for the subject to properly don or apply the device. Once the device has been provided 200 to the subject, the next step is to measure the subject's external body motion 245 while the subject performs at least two first movement disorder tests, activity, movement or motion. Preferably, each of the at least two first tests belong or correspond to the same symptom group of classification. For example, if the tests are performed under the guidelines of the UPDRS, the each of the at least two test would correspond to the same grouping or section of the UPDRS, such as the Motor Examination section (UPDRS-III), or the like. Different testing methods or protocols may have different groupings or classifications of symptoms, and preferably each of the at least two tests performed correspond to the same grouping or classification in whichever method or protocol is used. The at least two tests, activities, movements or motions preferably correspond to at least one symptom of a movement disorder in such a way that the test, activity, movement or motion is likely to exhibit at least one symptom of a movement disorder. When the subject performs the at least two tests, activities, movements or motions the at least one sensor of the device measures 245 the external body motion of the subject, including any movement disorder symptom motions that are present. Either after the test is complete, or during testing, a signal from the at least one sensor is transmitted to a processor 250. The processor then calculates a symptom quantification measure or score 255 from the at least two first tests performed. This first symptom quantification measure or score is based at least in part on the signal received from the at least one sensor of the device corresponding to the subject's external body motion during the at least two first tests, activities, movements or motions, and is preferably stored for later comparison, analysis, evaluation, recollection, or other uses. The symptom quantification measure or score is preferably calculated 255 substantially in real time corresponding to the performance and/or completion of the first movement disorder test.

Subsequently, at least two second movement disorder tests are performed. Similar to the at least two first tests, the device measures the subject's external body motion while the subject is performing the at least two second tests 260. The at least two second tests may be performed either immediately following the first tests, or, more preferably, at a later time (e.g., up to 30 days later), but are performed under substantially similar circumstances as the first tests. Similarly, the second tests are preferably the same tests, activities, movements or motions as the first movement disorder tests. Again, the second signal from the at least one sensor is transmitted to a processor 265 for comparison, analysis, evaluation, recollection, or the like. The processor similarly uses this second signal to calculate a second symptom quantification measure or score 270. This process may be repeated any number of times, each time conducting the same movement disorder tests comprising the same tests, activities, movements or motions under substantially similar circumstances. The separate symptom quantification measures or scores can then be compared in order to calculate various sensitivity metrics corresponding to the repeatability, accuracy, consistency and the like of the device, method and/or system. In many embodiments, the separate symptom quantification measures or scores are used to measure sensitivity by calculating the intraclass correlation (ICC) 275 of the symptom quantification measures, and preferably the ICC is at least about 0.60.

Figure 20:
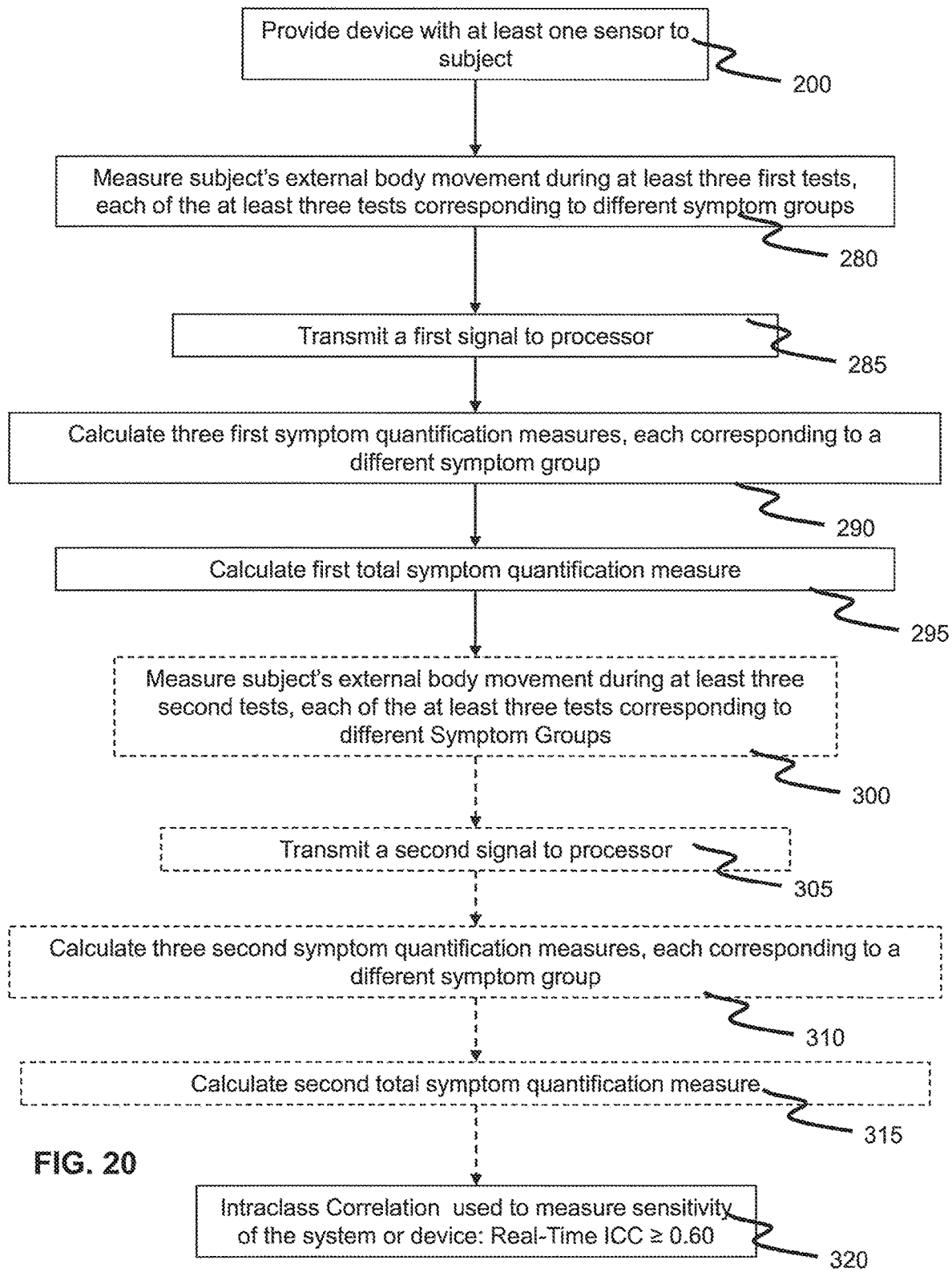
FIG. 20. Flow diagram of another embodiment of a sensitive method for quantifying movement disorder symptom severity comprising a set of at least three tests, each of the at least three tests corresponding to a different group or classification of symptoms, wherein the set of at least three tests are repeated, and where sensitivity is measured by intraclass correlation (ICC).

FIG. 20 is a flow chart depicting the methods of several embodiments of the present invention for quantifying a subject's movement disorder symptoms where sensitivity is measured using intraclass correlation (ICC). First, a device comprising at least one sensor, the at least one sensor having a signal corresponding to a subject's external body motion associated with a movement disorder, is provided 200 to the subject. The at least one sensor may be of any variety described herein, including, but not limited to accelerometers, gyroscopes, pressure sensors, force sensors, and the like. The step of providing 200 the device comprising at least one sensor to the subject may further comprise steps of giving instructions for the subject to properly don or apply the device. Once the device has been provided 200 to the subject, the next step is to measure the subject's external body motion 280 while the subject performs at least three first movement disorder tests, activities, movements or motions. Preferably, each of the at least three tests, activities, movements or motions corresponds to at least one symptom of a movement disorder in such a way that the test, activity, movement or motion is likely to exhibit at least one symptom of a movement disorder. Further, each of the at least three tests, activities, movements or motions preferably corresponds to a separate symptom grouping or classification. For example, if the tests are performed under the guidelines of the UPDRS, then each of the at least three tests would correspond to a different symptom grouping of the Motor Examination section (UPDRS-III), or the like. Different testing methods or protocols may have different groupings or classifications of symptoms, and preferably each of the at least three tests performed correspond to a different grouping or classification in whichever method or protocol is used. When the subject performs the at least three tests, activities, movements or motions the at least one sensor of the device measures the external body motion of the subject, including any movement disorder symptom motions that are present. Either after the test is complete, or during testing, a signal from the at least one sensor is transmitted to a processor 285. This first signal may comprise at least three separate signals from the at least one sensor where each signal corresponds to the measured external body motion of the at least three separate tests, activities, movements or motions, or alternatively, may be a composite signal representing all of the measured motions as a whole. In either embodiment, the first signal represents the motion measured during the at least three first tests. The processor then calculates a separate symptom quantification measure or score 290 from the first tests performed, at least one symptom quantification measure for each separate symptom grouping or classification. Each of the at least three separate first symptom quantification measures are based at least in part on the signal received from the at least one sensor of the device corresponding to the subject's external body motion during the at least three first tests, activities, movements or motions, and are preferably stored for later comparison, analysis, evaluation, recollection, or other uses. Next, the at least three separate symptom quantification measures or scores are combined to calculate a first total symptom quantification measure or score 295 that corresponds to the quantification of the overall severity of the subject's movement disorder symptoms as a whole across all tested groupings or categories of symptoms. Each of the separate first symptom quantification measures or scores, as well as the first total symptom quantification measure or score, is preferably calculated 290, 295 substantially in real time corresponding to the performance and/or completion of the first movement disorder test.

Subsequently, a second set of at least three movement disorder tests is performed. Similar to the at least three first tests, the device measures the subject's external body motion while the subject is performing the at least three second tests 300. These at least three second tests may be performed either immediately following the first tests, or, more preferably, at a later time (e.g., up to 30 days later), but are performed under substantially similar circumstances as the first tests. Similarly, the second tests are preferably the same tests, activities, movements or motions as the first movement disorder tests. Again, the second signal from the at least one sensor is transmitted to a processor 305 for comparison, analysis, evaluation, recollection, or the like. Much like the first signal, this second signal may comprise at least three separate signals from the at least one sensor where each signal corresponds to the measured external body motion of the at least three separate tests, activities, movements or motions, or alternatively, may be a composite signal representing all of the measured motions as a whole. In either embodiment, the second signal represents the motion measured during the at least three second tests. The processor similarly uses this second signal to calculate separate second symptom quantification measures or scores 310 from the second tests performed, at least one symptom quantification measure corresponding to each separate symptom grouping or classification. Each of the at least three separate second symptom quantification measures are based at least in part on the signal received from the at least one sensor of the device corresponding to the subject's external body motion during the at least three second tests, activities, movements or motions, and are preferably stored for later comparison, analysis, evaluation, recollection, or other uses. Next, the at least three separate second symptom quantification measures or scores are combined to calculate a second total symptom quantification measure or score 315 that corresponds to the quantification of the overall severity of the subject's movement disorder symptoms as a whole across all tested groupings or categories of symptoms. This process may be repeated any number of times, each time conducting the same movement disorder tests comprising the same tests, activities, movements or motions under substantially similar circumstances. The separate total symptom quantification measures or scores can then be compared in order to calculate various sensitivity metrics corresponding to the repeatability, accuracy, consistency and the like of the device, method and/or system. In many embodiments, the separate symptom quantification measures or scores are used to measure sensitivity by calculating the intraclass correlation (ICC) 320 of the symptom quantification measures, and preferably the ICC is at least about 0.60.

Figure 21:
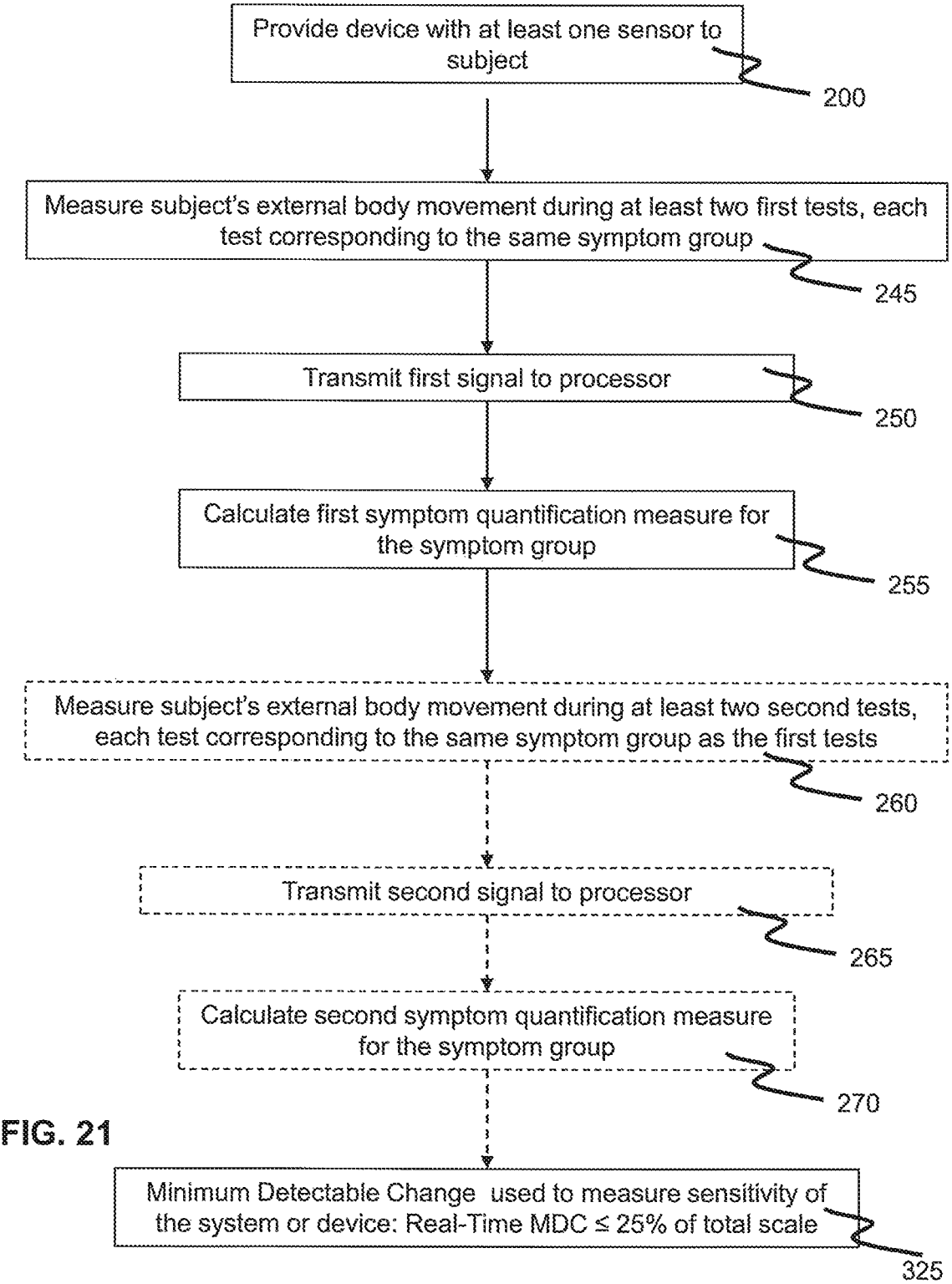
FIG. 21. Flow diagram of a sensitive method for quantifying movement disorder symptom severity comprising a set of at least two tests, both tests corresponding to the same grouping or classification of symptoms, wherein the set of at least two tests is repeated, and where sensitivity is measured by minimum detectable change (MDC) of repeated tests.

FIG. 21 is a flow chart depicting the methods of several embodiments of the present invention for quantifying a subject's movement disorder symptoms where sensitivity is measured using minimum detectable change (MDC). First, a device comprising at least one sensor, the at least one sensor having a signal corresponding to a subject's external body motion associated with a movement disorder, is provided 200 to the subject. The at least one sensor may be of any variety described herein, including, but not limited to accelerometers, gyroscopes, pressure sensors, force sensors, and the like. The step of providing 200 the device comprising at least three sensors to the subject may further comprise steps of giving instructions for the subject to properly don or apply the device. Once the device has been provided 200 to the subject, the next step is to measure the subject's external body motion 245 while the subject performs at least two first movement disorder tests, activity, movement or motion. Preferably, each of the at least two first tests belong or correspond to the same symptom group of classification. For example, if the tests are performed under the guidelines of the UPDRS, the each of the at least two test would correspond to the same grouping or section of the UPDRS, such as the Motor Examination section (UPDRS-III), or the like. Different testing methods or protocols may have different groupings or classifications of symptoms, and preferably each of the at least two tests performed correspond to the same grouping or classification in whichever method or protocol is used. The at least two tests, activities, movements or motions preferably corresponds to at least one symptom of a movement disorder in such a way that the test, activity, movement or motion is likely to exhibit at least one symptom of a movement disorder. When the subject performs the at least two tests, activities, movements or motions the at least one sensor of the device measures 245 the external body motion of the subject, including any movement disorder symptom motions that are present. Either after the test is complete, or during testing, a signal from the at least one sensor is transmitted to a processor 250. The processor then calculates a symptom quantification measure or score 255 from the at least two first tests performed. This first symptom quantification measure or score is based at least in part on the signal received from the at least one sensor of the device corresponding to the subject's external body motion during the at least two first tests, activities, movements or motions, and is preferably stored for later comparison, analysis, evaluation, recollection, or other uses. The symptom quantification measure or score is preferably calculated 255 substantially in real time corresponding to the performance and/or completion of the first movement disorder test.

Subsequently, at least two second movement disorder tests are performed. Similar to the at least two first tests, the device measures the subject's external body motion while the subject is performing the at least two second tests 260. The at least two second tests may be performed either immediately following the first tests, or, more preferably, at a later time (e.g., up to 30 days later), but are performed under substantially similar circumstances as the first tests. Similarly, the second tests are preferably the same tests, activities, movements or motions as the first movement disorder tests. Again, the second signal from the at least one sensor is transmitted to a processor 265 for comparison, analysis, evaluation, recollection, or the like. The processor similarly uses this second signal to calculate a second symptom quantification measure or score 270. This process may be repeated any number of times, each time conducting the same movement disorder tests comprising the same tests, activities, movements or motions under substantially similar circumstances. The separate symptom quantification measures or scores can then be compared in order to calculate various sensitivity metrics corresponding to the repeatability, accuracy, consistency and the like of the device, method and/or system. In many embodiments, the separate symptom quantification measures or scores are used to measure sensitivity by calculating the minimum detectable change (MDC) 325 of the symptom quantification measures, and preferably the MDC represents at a change of about 25% or less of the total scale of the particular test(s). As noted herein, the scale and measurement units of each individual test will vary (e.g., a gait test or test for standing up from a seated position may be measured in time with a total maximum allowable time to set the scale, whereas other tests may be measured in unitless scores or different units such as frequency, each with a different scale for maximum allowable measurements).

Figure 22:
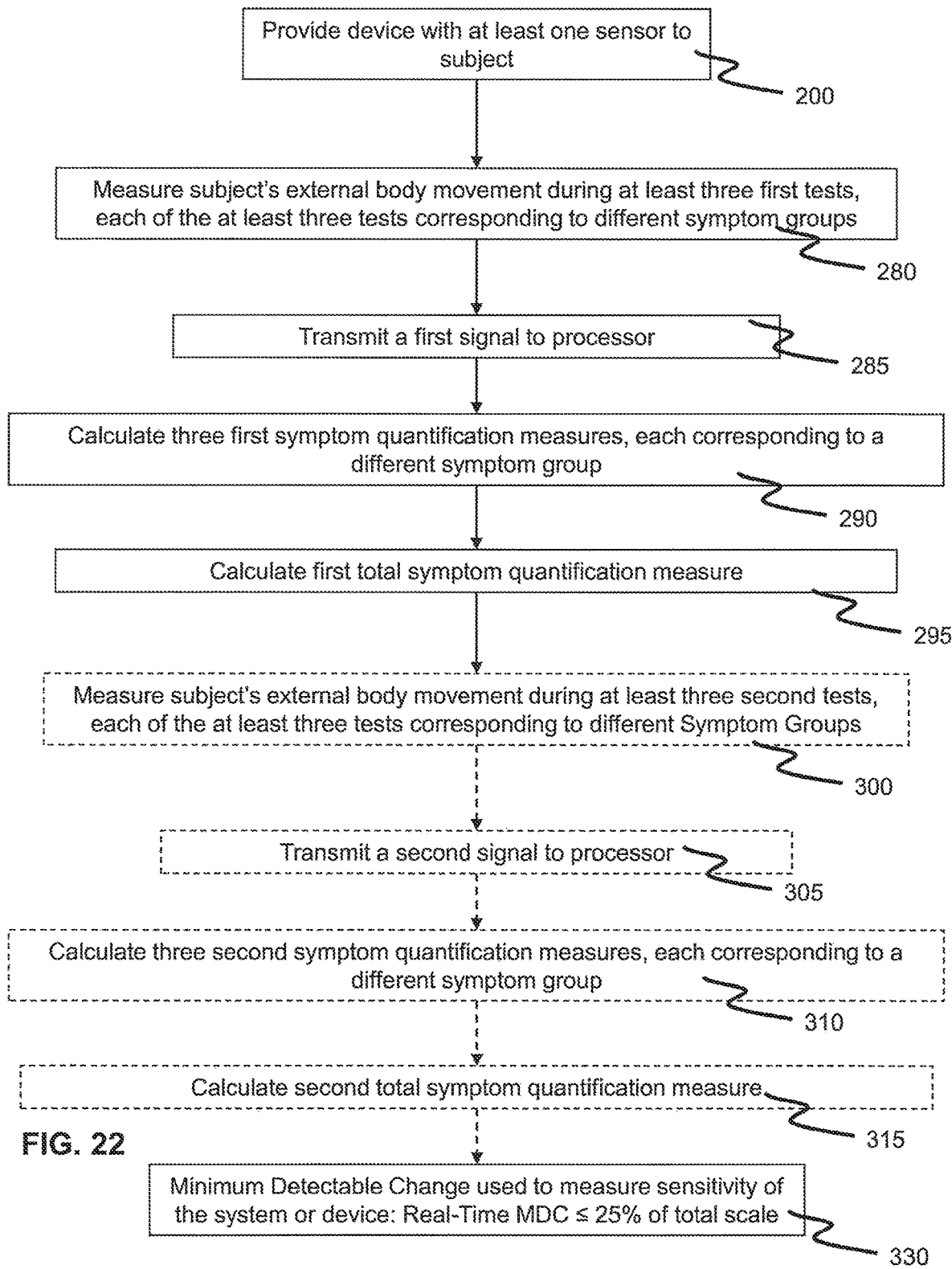
FIG. 22. Flow diagram of another embodiment of a sensitive method for quantifying movement disorder symptom severity comprising a set of at least three tests, each of the at least three tests corresponding to a different group or classification of symptoms, wherein the set of at least three tests are repeated, and where sensitivity is measured by minimum detectable change (MDC).

FIG. 22 is a flow chart depicting the methods of several embodiments of the present invention for quantifying a subject's movement disorder symptoms where sensitivity is measured using minimum detectable change (MDC). First, a device comprising at least one sensor, the at least one sensor having a signal corresponding to a subject's external body motion associated with a movement disorder, is provided 200 to the subject. The at least one sensor may be of any variety described herein, including, but not limited to accelerometers, gyroscopes, pressure sensors, force sensors, and the like. The step of providing 200 the device comprising at least one sensor to the subject may further comprise steps of giving instructions for the subject to properly don or apply the device. Once the device has been provided 200 to the subject, the next step is to measure the subject's external body motion 280 while the subject performs at least three first movement disorder tests, activities, movements or motions. Preferably, each of the at least three tests, activities, movements or motions corresponds to at least one symptom of a movement disorder in such a way that the test, activity, movement or motion is likely to exhibit at least one symptom of a movement disorder. Further, each of the at least three tests, activities, movements or motions preferably corresponds to a separate symptom grouping or classification. For example, if the tests are performed under the guidelines of the UPDRS, then each of the at least three tests would correspond to a different grouping or section of the UPDRS, such different symptoms under the Motor Examination section (UPDRS-III), or the like. Different testing methods or protocols may have different groupings or classifications of symptoms, and preferably each of the at least three tests performed correspond to a different grouping or classification in whichever method or protocol is used. When the subject performs the at least three tests, activities, movements or motions the at least one sensor of the device measures the external body motion of the subject, including any movement disorder symptom motions that are present. Either after the test is complete, or during testing, a signal from the at least one sensor is transmitted to a processor 285. This first signal may comprise at least three separate signals from the at least one sensor where each signal corresponds to the measured external body motion of the at least three separate tests, activities, movements or motions, or alternatively, may be a composite signal representing all of the measured motions as a whole. In either embodiment, the first signal represents the motion measured during the at least three first tests. The processor then calculates a separate symptom quantification measure or score 290 from the first tests performed, at least one symptom quantification measure for each separate symptom grouping or classification. Each of the at least three separate first symptom quantification measures are based at least in part on the signal received from the at least one sensor of the device corresponding to the subject's external body motion during the at least three first tests, activities, movements or motions, and are preferably stored for later comparison, analysis, evaluation, recollection, or other uses. Next, the at least three separate symptom quantification measures or scores are combined to calculate a first total symptom quantification measure or score 295 that corresponds to the quantification of the overall severity of the subject's movement disorder symptoms as a whole across all tested groupings or categories of symptoms. Each of the separate first symptom quantification measures or scores, as well as the first total symptom quantification measure or score, is preferably calculated 290, 295 substantially in real time corresponding to the performance and/or completion of the first movement disorder test.

Subsequently, a second set of at least three movement disorder tests is performed. Similar to the at least three first tests, the device measures the subject's external body motion while the subject is performing the at least three second tests 300. These at least three second tests may be performed either immediately following the first tests, or, more preferably, at a later time (e.g., up to 30 days later), but are performed under substantially similar circumstances as the first tests. Similarly, the second tests are preferably the same tests, activities, movements or motions as the first movement disorder tests. Again, the second signal from the at least one sensor is transmitted to a processor 305 for comparison, analysis, evaluation, recollection, or the like. Much like the first signal, this second signal may comprise at least three separate signals from the at least one sensor where each signal corresponds to the measured external body motion of the at least three separate tests, activities, movements or motions, or alternatively, may be a composite signal representing all of the measured motions as a whole. In either embodiment, the second signal represents the motion measured during the at least three second tests. The processor similarly uses this second signal to calculate separate second symptom quantification measures or scores 310 from the second tests performed, at least one symptom quantification measure corresponding to each separate symptom grouping or classification. Each of the at least three separate second symptom quantification measures are based at least in part on the signal received from the at least one sensor of the device corresponding to the subject's external body motion during the at least three second tests, activities, movements or motions, and are preferably stored for later comparison, analysis, evaluation, recollection, or other uses. Next, the at least three separate second symptom quantification measures or scores are combined to calculate a second total symptom quantification measure or score 315 that corresponds to the quantification of the overall severity of the subject's movement disorder symptoms as a whole across all tested groupings or categories of symptoms. This process may be repeated any number of times, each time conducting the same movement disorder tests comprising the same tests, activities, movements or motions under substantially similar circumstances. The separate total symptom quantification measures or scores can then be compared in order to calculate various sensitivity metrics corresponding to the repeatability, accuracy, consistency and the like of the device, method and/or system. In many embodiments, the separate symptom quantification measures or scores are used to measure sensitivity by calculating the minimum detectable change (MDC) 330 of the symptom quantification measures, and preferably the MDC represents at a change of about 25% or less of the total scale of the particular test(s). As noted herein, the scale and measurement units of each individual test will vary (e.g., a gait test or test for standing up from a seated position may be measured in time with a total maximum allowable time to set the scale, whereas other tests may be measured in unitless scores or different units such as frequency, each with a different scale for maximum allowable measurements).

Figure 23:
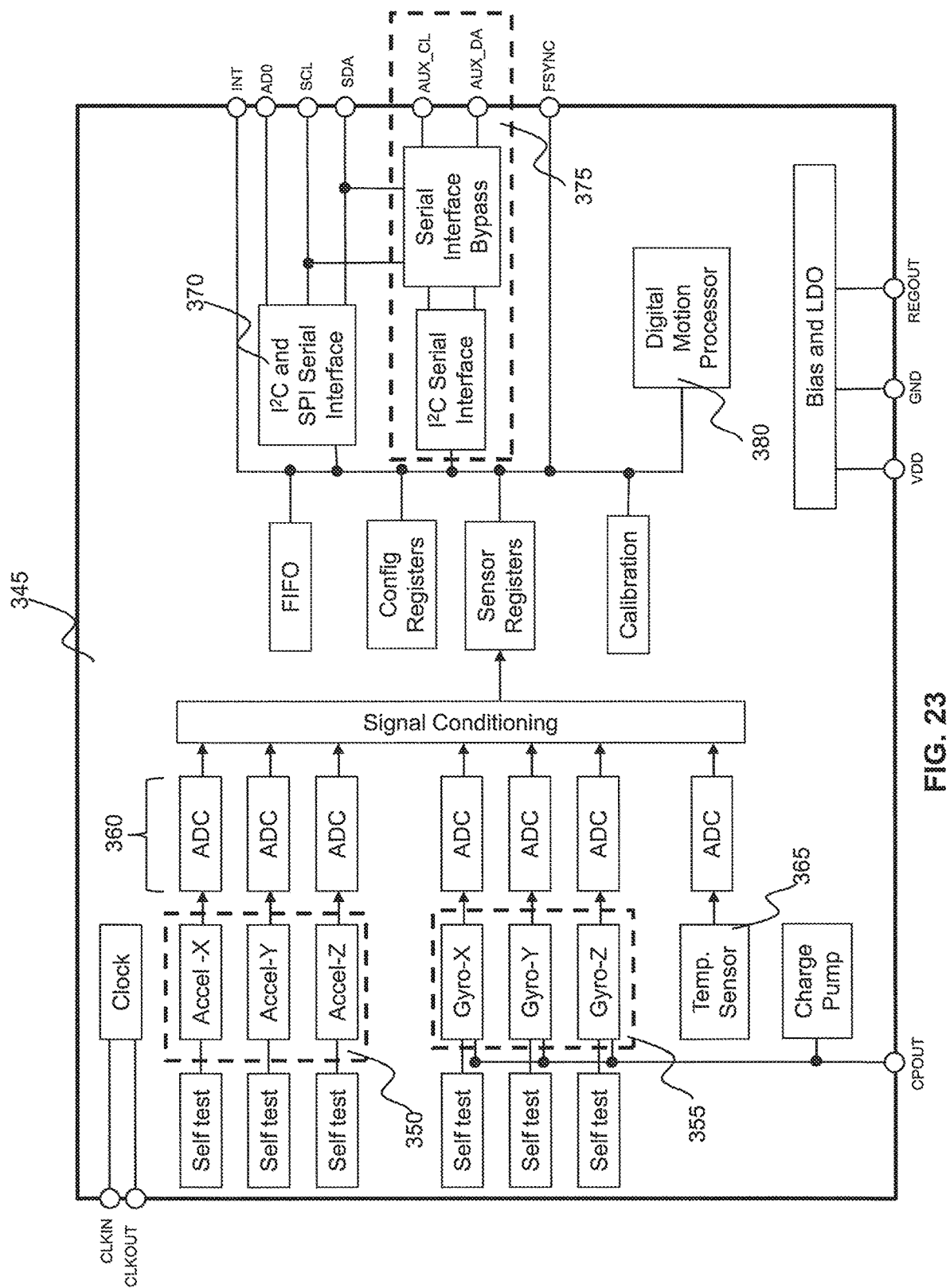
FIG. 23. Electrical schematic/block diagram of alternative sensor unit comprising a 3-axis accelerometer and a 3-axis gyroscope.

FIG. 23 depicts an electrical schematic block diagram of an alternative sensor unit 345 embodiment. In this embodiment, rather than using a separate accelerometer and a separate gyroscope to measure the various external body movements of the subject, a single sensor unit 345 comprising at least an accelerometer and a gyroscope may be used. The sensor unit 345 preferably not only comprises at least an accelerometer 350 (denoted by the dashed box) and a gyroscope 355 (denoted by the dashed box), but also allows for integration of other sensors external to the sensor unit 345. Preferably, the accelerometer 350 and gyroscope 355 are each three-axis sensors capable of measuring their respective movements (acceleration and orientation) in each of the three dimensions of movement (X, y and Z). Each of the accelerometer and gyroscope may output a separate signal for their respective measurements in each axis, and these signals are all converted from analog to digital by a bank of analog-to-digital converters (ADC) 360. The separate ADCs for each axis of the accelerometer and gyroscope allows for simultaneous sampling of each sensor and eliminates the need for an external multiplexer. Preferably the sensor unit 345 as a whole, and the accelerometer and gyroscope in particular are capable of operation with low power consumption. Preferably, the accelerometer and gyroscope are user-programmable such that the user may define an operating range in which the sensors will work (e.g., the accelerometer may be programmed to operate from as low as ±2 g to as high as ±16 g, and the gyroscope from as low as ±250 degrees/second to as high as ±2000 degrees/second). Some embodiments may include other sensors integrated into the sensor unit 345 as well, for example, a temperature sensor 365 which may be used to monitor the temperature of the sensor unit 345 and ensure it is operating properly and under safe conditions.

The sensor unit 345 further comprises a digital motion processor (DMP) 380 which may perform some preprocessing or processing of the sensor signals using motion-related algorithms. The digital motion processor 380 at least preprocesses and/or processes the accelerometer and gyroscope signals to begin the analysis of the signals and to decrease the processing load on the external processor (not shown). Many embodiments may include external or additional sensors (not shown) that are not housed within the sensor unit 345, but whose signals are transmitted to the sensor unit 345 for integration with the accelerometer and gyroscope signals for further transmission to external components (not shown) such as a processor. Such external or additional sensors may include, but are not limited to, force sensors, magnetometers, pressure sensors, bend sensors, combinations thereof, and the like). These external or additional sensors communicate with the sensor unit 345 by means of an auxiliary communications interface 375. The digital motion processor can integrate the signal(s) from these external or additional sensors along with the accelerometer and gyroscope signals and perform preprocessing or processing of all of the signals together, thus further streamlining the data acquisition process and reducing the workload of the external processor (not shown).

Figure 24:
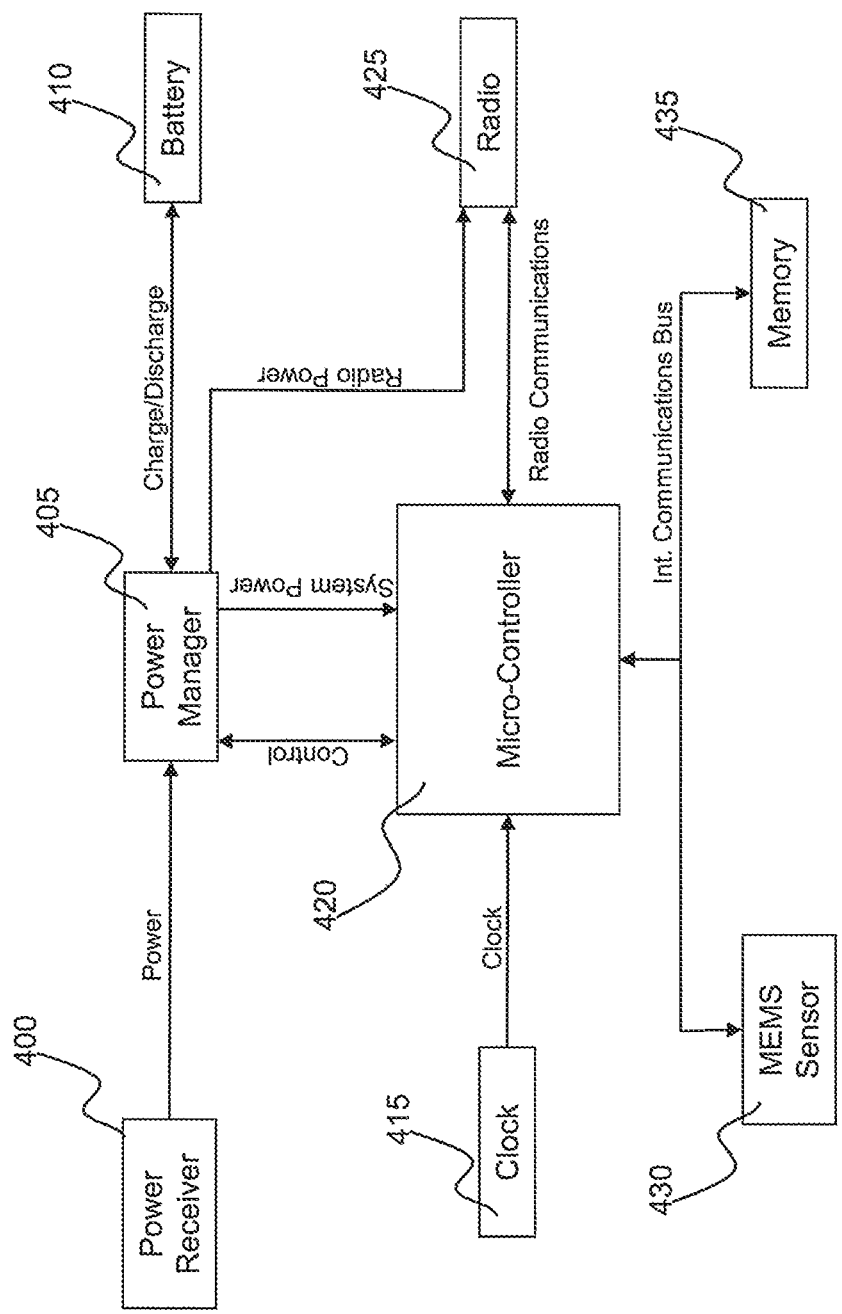
FIG. 24. Block diagram depicting electronic components of one embodiment of the present invention of a subject worn sensor unit for measuring the subject's external body movements and quantifying the severity of movement disorder symptoms.

FIG. 24 is a block diagram of the electronic components of one embodiment of the present invention. The power receiver 400 is the component which receives the electrical charge from the external power source (not shown). The external power source can be any device for supplying power to the subject-worn sensor unit. In some embodiments, the external power source may be a docking station to which the subject-worn sensor unit can be connected, attached, docked, or placed into whereby a physical connection is made between the docking station and the subject-worn unit thus allowing power to be transferred via the physical connection. In other embodiments, the external power source may merely involve plugging the subject-worn sensor unit into a traditional power outlet. In still other embodiments, the external power source may be an inductive charging mat or pad onto which the subject-worn sensor unit is placed and power may be inductively transferred between induction coils in the charging mat or pad and the inductive coils in the power receiver 400 of the subject-worn sensor unit, as described herein. As the power receiver, which may be wireless or wired depending on the embodiment, receives power, it transfers said power to a power manager 405 which controls and directs where the incoming power is delivered. If the subject-worn sensor unit is not being presently used to measure a subject's body movements and is instead being charged, then the power manager 405 directs the incoming power to the device's batter 410 for charging. It might be possible, though not necessarily preferred, for some embodiments to allow charging while the unit is being used to measure a subject's body motions, in which case the power manager 405 would direct the incoming power to either the battery 410 or to the micro-controller 420 for powering the devices operation for testing. However, it is more preferable for the device, during operation for testing, to be untethered and not in charging mode, and thus the battery 410 would provide power to the unit for usage and testing purposes.

The micro-controller 420 or microprocessor is the internal processing unit that directs the other components to function. Thus, the micro-controller 420 or microprocessor directs the power manager 405 on where to direct the power it is receiving from either the power receiver 400 or the battery 405. The electronic clock 415 operates as commonly known in the art to control synchronization and operation of the device to maximize efficiency of power usage. The radio 425 of the device controls and carries out communications between the device components, and between the subject-worn sensor unit and external devices (not shown). The radio 425 receives power directly from the power manager. As described herein, the radio may be a blue tooth communications device to provide wireless communications with external components such as computers or processors, EMG signal amplifiers, data acquisition circuitry, internet or cloud-based memory banks or databases, and the like, as well as internal components such as the internal subject-worn sensor unit memory 435, microprocessor 420, and the like. Both internal (between electrical components of the subject-worn sensor device) and external (between the subject-worn sensor device and external components or devices) communications may also be transmitted through wireless, wired, or a combination of both methods.

The subject-worn sensor device must, as described throughout, comprise at least one sensor 430. In the depicted embodiment, a MEMS sensor is included in the device. This sensor 430 may be of any of the varieties described herein or combinations thereof, though most preferably comprises at least an accelerometer and a gyroscope. The device further comprises internal memory 435 which is used to store system settings as well as subject and test data to be transmitted to external components. The micro-controller 420 comprises algorithms and protocols for coordinating the operation of at least these internal electrical components, and in some embodiments also for preprocessing or processing sensor data.

Figure 25:
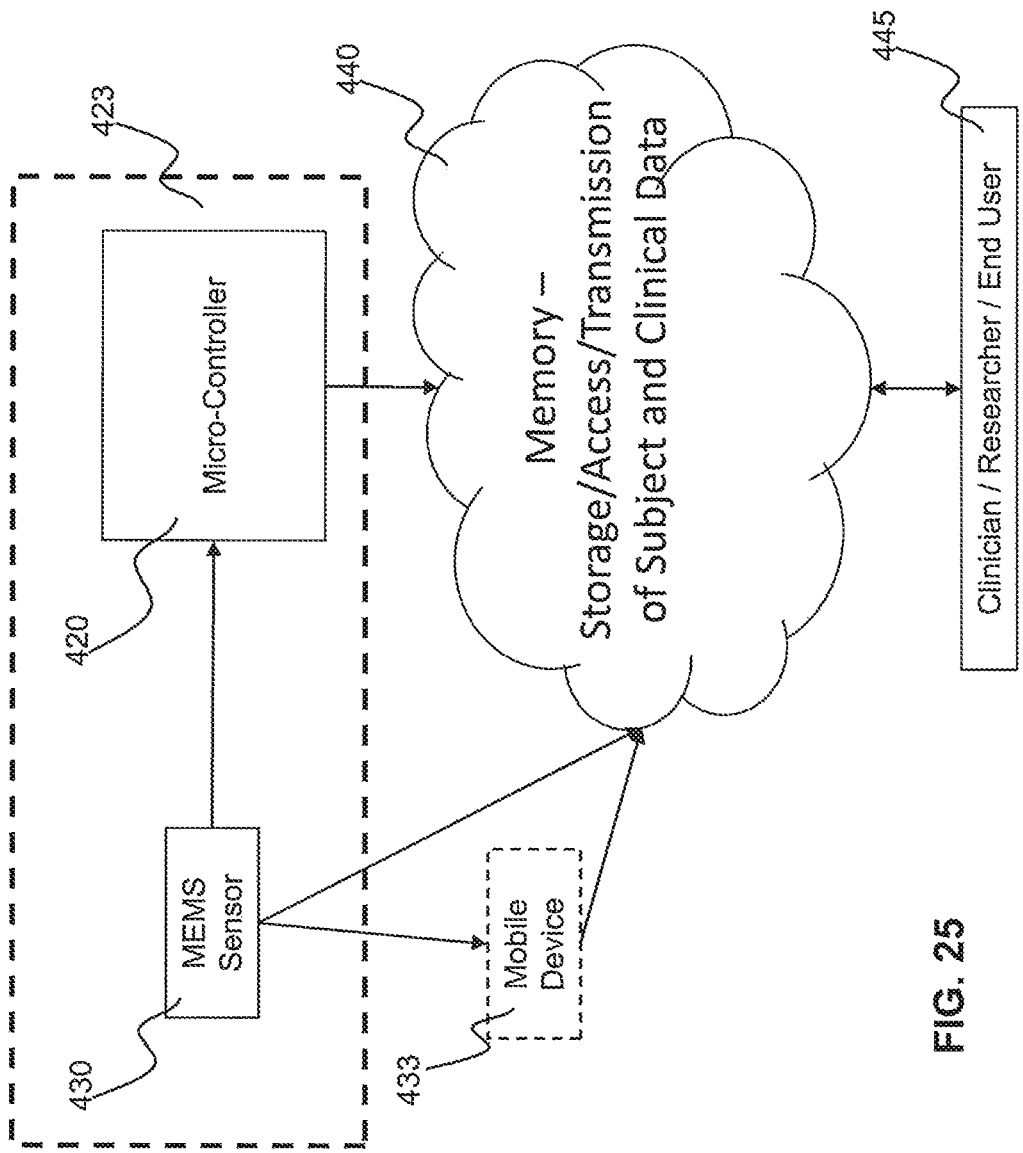
FIG. 25. Block diagram depicting data movement and availability between the device and end users.

FIG. 25 is a block diagram depicting the flow of data from the device measuring the subject's external body movements to the end user who views, analyzes and/or otherwise uses the data generated by the device. In all embodiments of the present invention, the various sensors 430 are used to measure the subject's external body motion as described herein. The sensors 430 then transmit a signal corresponding to the measured movements to a micro-controller or processor 420 which may perform some pre-processing or processing functions before transmitting the data to memory or storage 440. In many embodiments, the sensors 430 and micro-controller or processor 420 are contained in the same device 423 worn by the subject. Alternatively, in many embodiments, the sensors may transmit the data to a mobile device 433 which in turn may transmit the data to the memory or storage 440. In such embodiments, the mobile device 433 may be a tablet, PC, smartphone, or the like, and may merely make the data available to a user or may performs some processing functions on the data. Further alternatively, or in conjunction with the above step, the sensor(s) 430 may directly transmit data corresponding to the subject's external body movements to the memory or storage 440. The memory or storage unit 440 may be internal to the device, though in many embodiments is preferably an external memory or storage unit. In still further embodiments, the memory or storage unit 440 is still more preferably a cloud-based storage server. In most embodiments, the memory or storage 440 preferably makes the data available to an end user 445 very soon after the sensor(s) 430 record the subject's external body movements. The end user 445 may be a clinician who is using the data to diagnose, treat, or monitor a subject. Another potential end user may be a researcher or study administrator who is conducting a clinical trial and is collecting the data for research purposes, such as for testing the efficacy of a drug. Other potential end users are also envisioned as using the data, but the main goal is for the device to make the data available to any authorized end user as rapidly as possible after recording the subject's movement. Most preferably, the data is uploaded or transmitted to the memory or storage 440 substantially simultaneously with recording by the sensor(s) 430, or with pre-processing or processing by the micro-controller or processor 420, depending on the path and particular embodiment.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A movement disorder device or system for treating a subject's movement disorder through deep brain stimulation based on a calculated severity of symptoms of the subject's movement disorder, the device or system comprising:
a diagnostic component comprising a sensor unit component and a processor, the sensor unit component comprising at least one sensor having a signal associated with such external body motion;
the processor for receiving the signal and calculating a quantified severity of the subject's symptoms of movement disorder in real time; and
a treatment delivery component comprising at least one electronic component or actuator adapted for adjusting a device for a treatment of the subject's movement disorder or symptoms of a movement disorder through deep brain stimulation where an electrical output of the deep brain stimulation is adjusted based in part on the calculated quantified severity of the subject's symptoms of movement disorder in real time,
wherein the diagnostic component has a real-time average intraclass correlation (ICC) of at least about 0.60 for the quantified severity of the subject's particular symptoms of movement disorder.

2. The device or system in claim 1, wherein the symptoms include one or more of tremor, bradykinesia, gait disturbances, balance disturbances, dyskinesia, and rigidity.

3. The device or system in claim 2, wherein the quantification of severity of at least one symptom is based on one or more variables computed from the acquired movement data, the variables including peak frequency, average amplitude, average power, frequency, peak frequency, number of hesitations, linear or exponential fit coefficients used to fit a model to the amplitude of a subject's movement over time, or range of motion.

4. The device or system in claim 3, further comprising at least one electromyogram (EMG) sensor adapted to measure electrical muscle activity of the subject and the quantified severity of the subject's symptoms is calculated based at least in part on the measured electrical muscle activity.

5. The device or system in claim 4, wherein processor is further adapted to generate a subject report based at least in part on the signal from the at least one sensor and on the measured electrical muscle activity.

6. The device or system in claim 5, wherein the subject report is transmitted to a physician, clinician, or technician for review.

7. A movement disorder device or system for treating a subject's movement disorder with a pharmaceutical based on a calculated severity of symptoms of the subject's movement disorder, the device or system comprising:
a diagnostic component comprising a sensor unit component and a processor, the sensor unit component comprising at least one sensor having a signal associated with such external body motion;
the processor for receiving the signal and calculating a quantified severity of the subject's symptoms of movement disorder in real time; and
a treatment delivery component comprising at least one electronic component or actuator adapted for adjusting a device for a treatment of the subject's movement disorder or symptoms of movement disorder with a pharmaceutical where the pharmaceutical is adjusted based in part on the calculated quantified severity of the subject's symptoms of movement disorder in real time,
wherein the diagnostic component has a real-time average intraclass correlation (ICC) of at least about 0.60 for the quantified severity of the subject's particular symptoms of movement disorder.

8. The device or system in claim 7, wherein the treatment delivery component is a drug delivery device, and the recommended treatment protocol comprises one or more of a new drug to administer, a new drug dose, and dose timing.

9. The device or system in claim 7, wherein the symptoms include one or more of tremor, bradykinesia, gait disturbances, balance disturbances, dyskinesia, and rigidity.

10. The device or system in claim 9, wherein the quantification of severity of at least one symptom is based on one or more variables computed from the acquired movement data, the variables including peak frequency, average amplitude, average power, frequency, peak frequency, number of hesitations, linear or exponential fit coefficients used to fit a model to the amplitude of a subject's movement over time, or range of motion.

11. The device or system in claim 10, wherein treatment delivery component is a drug delivery device, and the recommended treatment protocol comprises one or more of a new drug to administer, a new drug dose, and dose timing.

12. The device or system in claim 11, further comprising at least one electromyogram (EMG) sensor adapted to measure electrical muscle activity of the subject and the quantified severity of the subject's symptoms is calculated based at least in part on the measured electrical muscle activity.

13. A movement disorder device or system for treating a subject's movement disorder with a pharmaceutical or through deep brain stimulation based on a calculated severity of symptoms, the device or system comprising:
a diagnostic component comprising a sensor unit component and a processor, the sensor unit component comprising at least one sensor having a signal associated with such external body motion;
the processor for receiving the signal and calculating a quantified severity of the subject's movement disorder symptoms in real time; and
a treatment delivery component comprising at least one electronic component or actuator adapted for adjusting a device for a treatment of the subject's movement disorder or symptoms of movement disorder with a pharmaceutical or through deep brain stimulation where the pharmaceutical or the electrical output of the deep brain stimulation is adjusted based in part on the calculated quantified severity of the subject's symptoms of Parkinson's in real time,
wherein the diagnostic component has a real-time average minimum detectable change (MDC) that represents a change of about 25% or less of a total scale of a particular rating scale of the symptom(s) when calibrated or adjusted.

14. The device or system in claim 13, wherein the treatment delivery component is a drug delivery device, and the recommended treatment protocol comprises one or more of a new drug to administer, a new drug dose, and dose timing.

15. The device or system in claim 13, wherein the symptoms include one or more of tremor, bradykinesia, gait disturbances, balance disturbances, dyskinesia, and rigidity.

16. The device or system in claim 15, wherein the quantification of severity of at least one symptom is based on one or more variables computed from the acquired movement data, the variables including peak frequency, average amplitude, average power, frequency, peak frequency, number of hesitations, linear or exponential fit coefficients used to fit a model to the amplitude of a subject's movement over time, or range of motion.

17. The device or system in claim 16, treatment delivery component is a drug delivery device, and the recommended treatment protocol comprises one or more of a new drug to administer, a new drug dose, and dose timing.

18. The device or system in claim 13, further comprising at least one electromyogram (EMG) sensor adapted to measure electrical muscle activity of the subject and the quantified severity of the subject's symptoms is calculated based at least in part on the measured electrical muscle activity.

19. The device or system in claim 18, wherein the processor is further adapted to generate a subject report based at least in part on the signal from the at least one sensor and on the measured electrical muscle activity.

20. The device or system in claim 19, wherein the subject report is transmitted to a physician, clinician, or technician for review.

* * * * *